United States Patent
Huang et al.

(10) Patent No.: US 12,383,269 B1
(45) Date of Patent: Aug. 12, 2025

(54) CONTINUOUS TRACK OF TISSUE GAP FOR CAMBERING ADJUSTMENT AND ACCURATE TISSUE MEASUREMENT

(71) Applicant: Cilag GmbH International, Zug (CH)

(72) Inventors: Zhifan Huang, Mason, OH (US); John Bruce, Morrow, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/634,417

(22) Filed: Apr. 12, 2024

(51) Int. Cl.
*A61B 17/072* (2006.01)
*A61B 17/29* (2006.01)

(52) U.S. Cl.
CPC ............ *A61B 17/07207* (2013.01); *A61B 2017/2939* (2013.01)

(58) Field of Classification Search
CPC ............ A61B 17/07207; A61B 17/068; A61B 17/1155; A61B 17/105
See application file for complete search history.

(56) References Cited

U.S. PATENT DOCUMENTS

| | | | |
|---|---|---|---|
| 8,210,411 B2 | 7/2012 | Yates et al. | |
| 9,186,142 B2 | 11/2015 | Fanelli et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 10,092,292 B2 | 10/2018 | Boudreaux et al. | |
| 10,182,813 B2 | 1/2019 | Leimbach et al. | |
| 11,304,697 B2 | 4/2022 | Fanelli et al. | |
| 11,317,912 B2 | 5/2022 | Jenkins et al. | |
| 11,439,391 B2 | 9/2022 | Bruns et al. | |
| 2019/0201091 A1* | 7/2019 | Yates | A61B 18/1233 |
| 2022/0104911 A1* | 4/2022 | Shelton, IV | G16H 40/60 |
| 2022/0331047 A1* | 10/2022 | Shelton, IV | G16H 20/40 |

* cited by examiner

*Primary Examiner* — Nathaniel C Chukwurah
(74) *Attorney, Agent, or Firm* — Lempia Summerfield Katz LLC

(57) ABSTRACT

A surgical stapling instrument includes first and second jaws, a sensor assembly, and a controller. The controller detects that the jaws have been actuated from closed position to open position and back to closed position, and derives, from a first signal from the sensor assembly, a current distance between the distal ends of the jaws. Upon determining firing immediately preceding actuation of the jaws, the controller adjusts a camber adjustment value based on the current distance. Upon determining no firing immediately preceding actuation of the jaws and closing of the jaws with tissue grasped, the controller adjusts the tissue thickness measurement based on the camber adjustment value and controls the next firing based thereon. Upon determining no firing immediately preceding actuation of the jaws and that closing of the jaws with no tissue grasped therein, the controller adjusts the camber adjustment value based on the current measurement of the distance.

26 Claims, 31 Drawing Sheets

CONTINUOUS TRACK OF TISSUE GAP FOR CAMBERING ADJUSTMENT AND ACCURATE TISSUE MEASUREMENT

BACKGROUND

In some settings, endoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion, which is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. In such instruments, a knife which performs the cutting is further coupled with, or otherwise drives/pushes, either directly or indirectly, a sled which deploys the staples such that the two move together to substantially simultaneously transect and staple the clamped tissue. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

In some procedures, it may be necessary to fire (i.e., cut and/or staple) along tissue where more than one firing is necessary to complete the procedure. In other words, it may be necessary to perform multiple sequential firings along a continuous path, known as "marching." With procedures that involve marching, a surgical stapler end effector may be placed at the surgical site, actuated to cut, and staple, removed from the surgical site for installation of a new staple cartridge, and then placed back at the surgical site again for the next firing along the same path. In some such procedures, the clinician may have a need to measure the tissue before cutting, e.g., to adjust firing parameters in order to enhance surgical performance. However, known surgical staplers have limited capabilities for providing information to enable such selections and adjustments.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
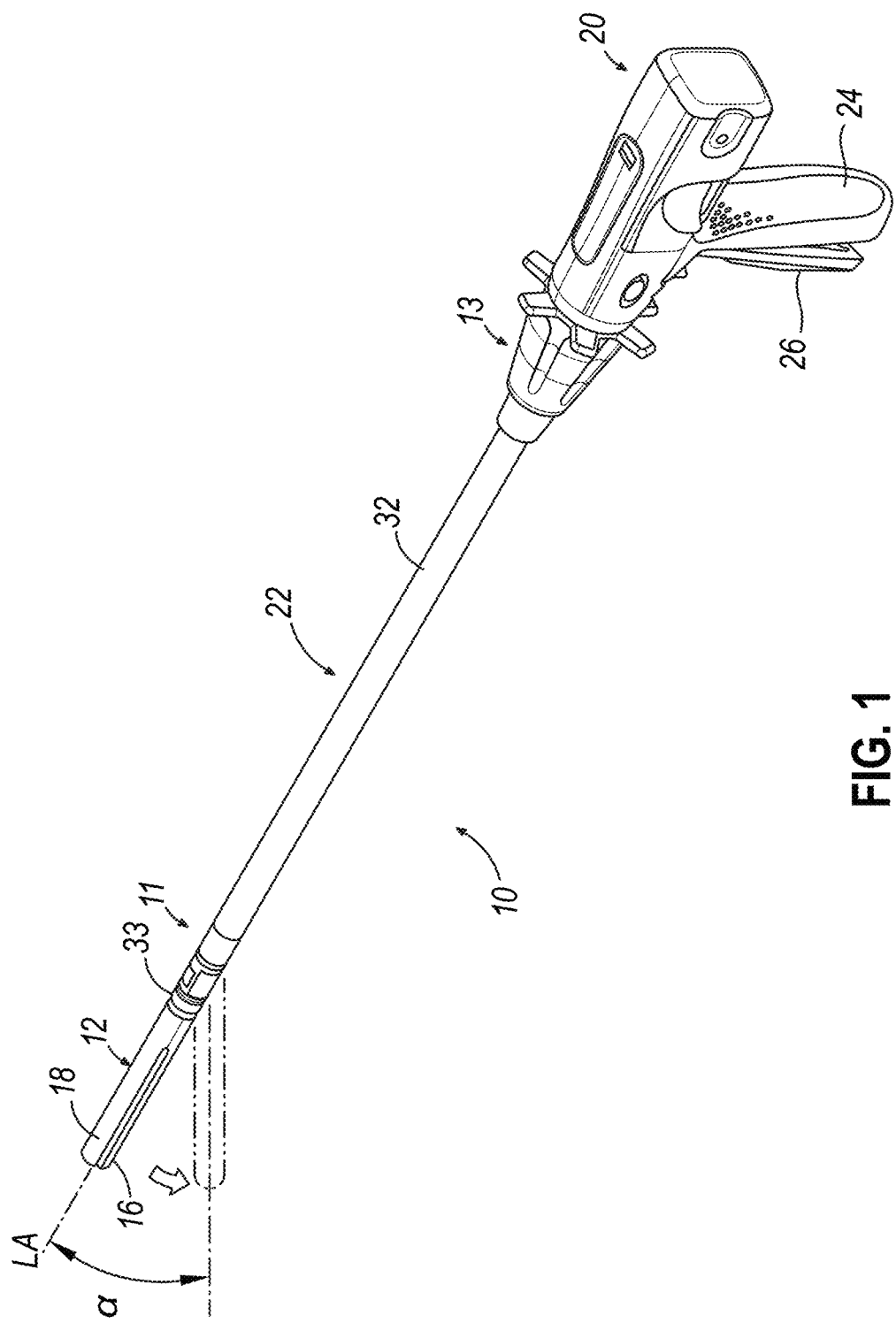
FIG. 1 depicts a perspective view of an example of an articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those having ordinary skill in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers to the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures.

As used herein in connection with various examples of end effector jaw tips, a tip described as "angled," "bent," or "curved" encompasses tip configurations in which a longitudinal path (e.g., linear, or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

I. Illustrative Surgical Stapler

FIGS. 1-7 depict an example of a surgical stapling and severing instrument 10 that is sized for insertion through a trocar cannula or an incision (e.g., thoracotomy, etc.) to a surgical site in a patient for performing a surgical procedure. Instrument 10 of the present example includes a handle portion 20 connected to a shaft 22, which distally terminates in an articulation joint 11, which is further coupled with an end effector 12. Once articulation joint 11 and end effector 12 are inserted through the cannula passageway of a trocar, articulation joint 11 may be remotely articulated, as depicted in phantom in FIG. 1, by an articulation control 13, such that end effector 12 may be deflected from the longitudinal axis (LA) of shaft 22 at a desired angle (a). End effector 12 of the present example includes a lower jaw 16 (also referred to herein as a cartridge jaw or second jaw) that includes a staple cartridge 37 (shown in FIG. 3), and an upper jaw 18 (also referred to herein as an upper jaw or first jaw) in the form of a pivotable anvil jaw.

Unless otherwise described, the term "pivot" (and variations thereof) as used herein encompasses but is not necessarily limited to pivotal movement about a fixed axis. For instance, in some versions, the anvil jaw 18 may pivot about an axis that is defined by a pin (or similar feature) that slidably translates along an elongate slot or channel as the anvil jaw 18 moves toward the lower jaw 16. Such translation may occur before, during, or after the pivotal motion. It should therefore be understood that such combinations of pivotal and translational movement are encompassed by the term "pivot" and variations thereof as used herein.

Handle portion 20 includes a pistol grip 24 and a closure trigger 26. Closure trigger 26 is pivotable toward pistol grip 24 to cause clamping, or closing, of the anvil jaw 18 toward lower jaw 16 of end effector 12. Such closing of the anvil jaw 18 is provided through a closure tube 32 and a closure ring 33, which both longitudinally translate relative to handle portion 20 in response to pivoting of closure trigger 26 relative to pistol grip 24. Closure tube 32 extends along the length of shaft 22; and closure ring 33 is positioned distal to articulation joint 11. Articulation joint 11 is operable to communicate/transmit longitudinal movement from closure tube 32 to closure ring 33.

Figure 2:
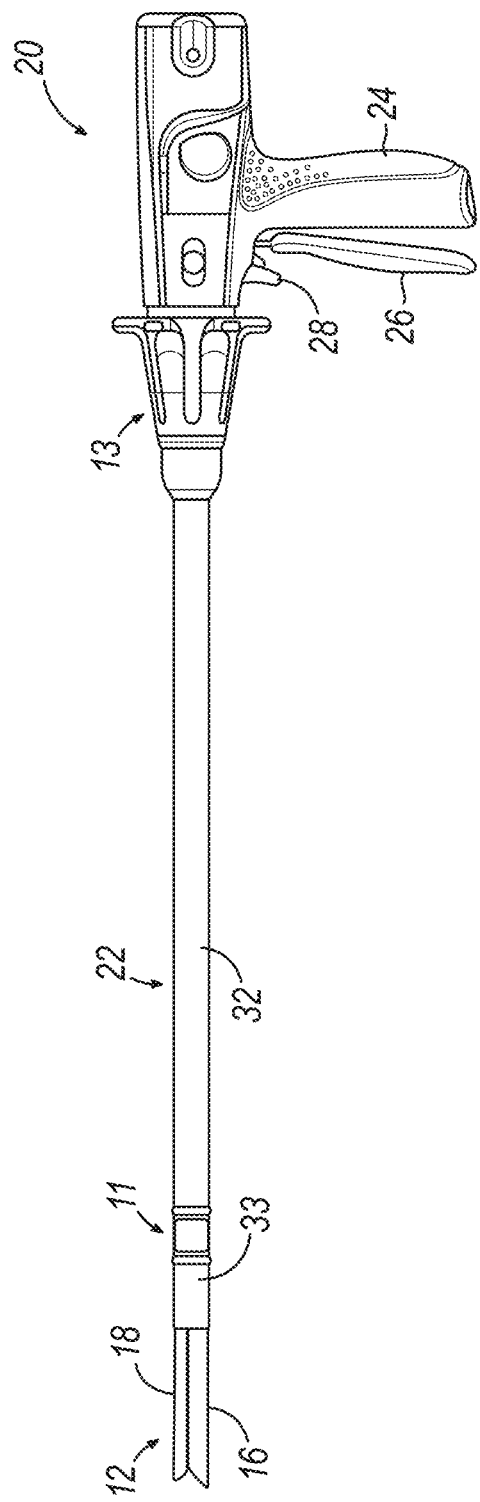
FIG. 2 depicts a side view of the instrument of FIG. 1.

As shown in FIG. 2, handle portion 20 also includes a firing trigger 28. An elongate member (not shown) longitudinally extends through shaft 22 and communicates a longitudinal firing motion from handle portion 20 to a firing beam 14 (shown in FIG. 3) in response to actuation of firing trigger 28. This distal translation of firing beam 14 causes the stapling and severing of clamped tissue in end effector 12, as will be described in greater detail below.

As shown in FIGS. 3-6, end effector 12 employs a firing beam 14 that includes a transversely oriented upper pin 38, a firing beam cap 44, a transversely oriented middle pin 46, and a distally presented knife/cutting edge 48. Upper pin 38 is positioned and translatable within a longitudinal anvil slot 42 of anvil jaw 18. Firing beam cap 44 slidably engages a lower surface of lower jaw 16 by having firing beam 14 extend through lower jaw slot 45 (shown in FIG. 4B) that is formed through lower jaw 16. Middle pin 46 slidingly engages a top surface of lower jaw 16, cooperating with firing beam cap 44. As the knife/cutting edge 48 advances through the cartridge slot 49, a lower portion of the cutting edge 48 engages, directly or indirectly, the sled 41 to push the sled 41 forward. As used herein, knife/cutting edge 48 refers to the entire cutting edge 48 assembly including the sharpened edge which moves through the cartridge slot 49 and actually engages/cuts the tissue, and the portions above and below which engage the slots 42, 45, in the upper and lower jaws 16, 18, which guide the cutting edge 48 as it advances distally and retracts proximally, as well as the portion which engages and pushes, directly or indirectly, the sled 41. In some embodiments, the cutting edge 48 directly engages/pushes the sled 41. In alternative embodiments, one or more intermediate driving components may be implemented between the sled 41 and the portion of the cutting edge 48 which engages and pushes the sled 41. In this implementation, the cutting edge 48 indirectly engages/pushes the sled 41, i.e., the cutting edge 48 engages/pushes the one or more intermediate driving components which in-turn engages/pushes the sled 41.

Figure 3:
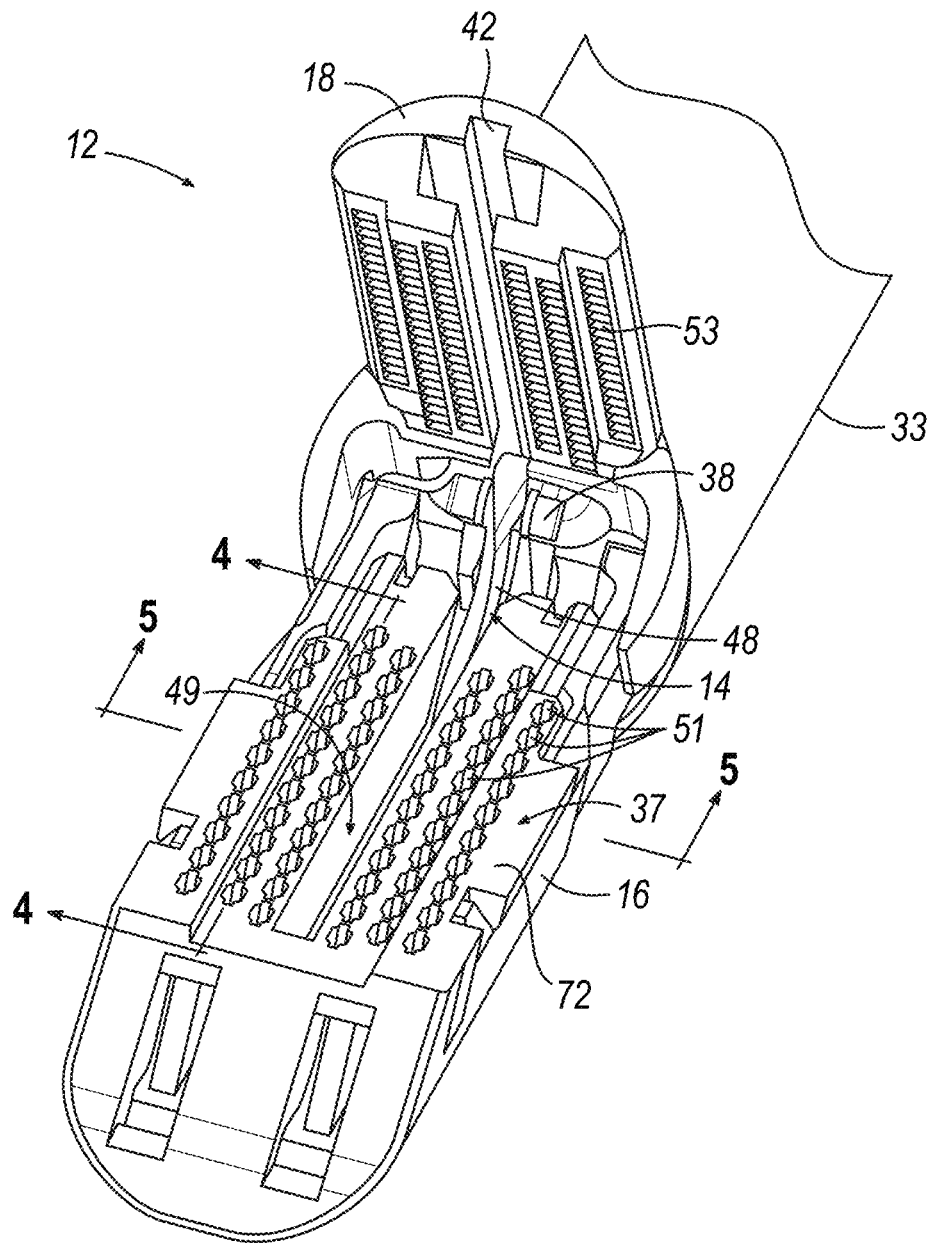
FIG. 3 depicts a perspective view of an opened end effector of the instrument of FIG. 1.
Figure 4A:
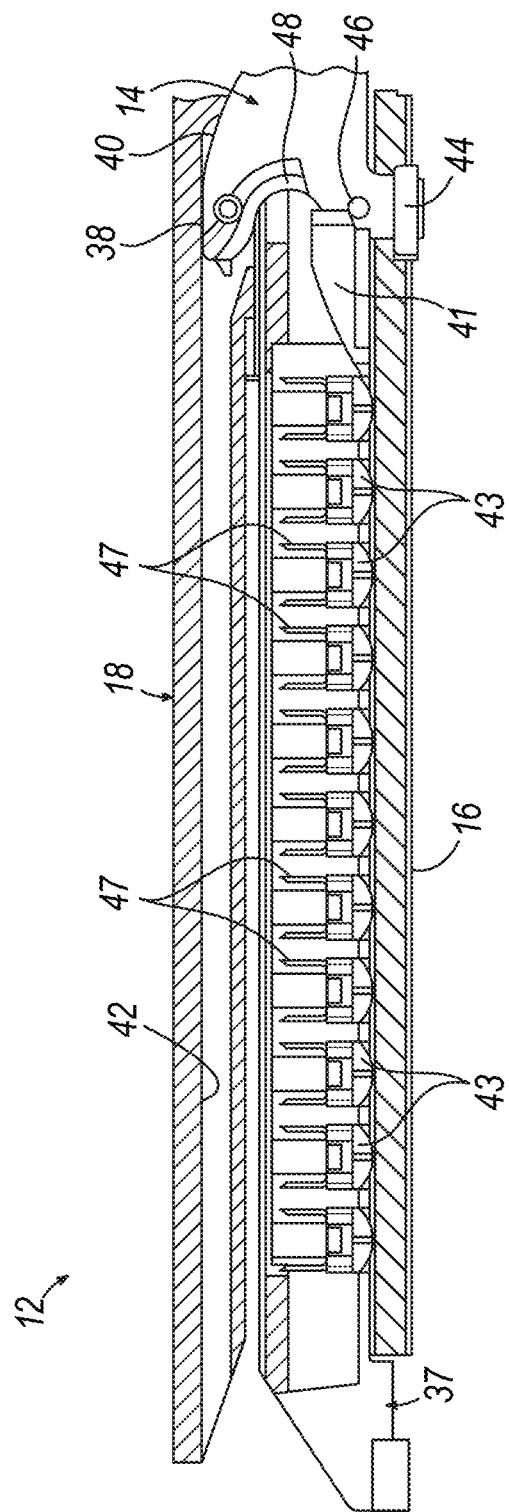
FIG. 4A depicts a side cross-sectional view of the end effector of FIG. 3, taken along line 4-4 of FIG. 3, with the firing beam in a proximal position.
Figure 4B:
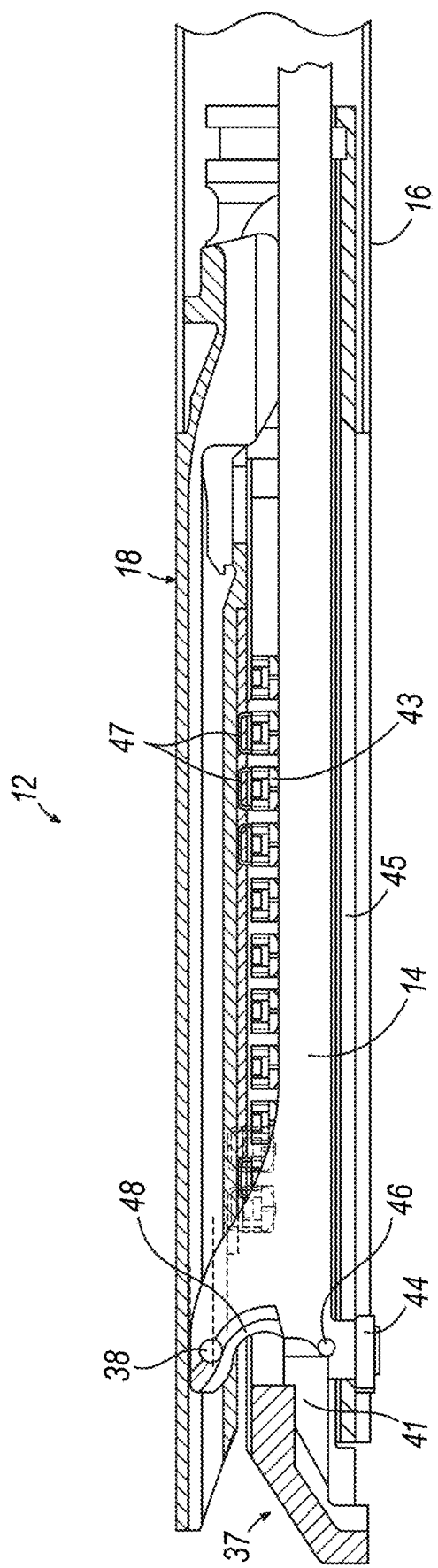
FIG. 4B depicts a side cross-sectional view of the end effector of FIG. 3, taken along line 4-4 of FIG. 3, with the firing beam in a distal position.
Figure 5:
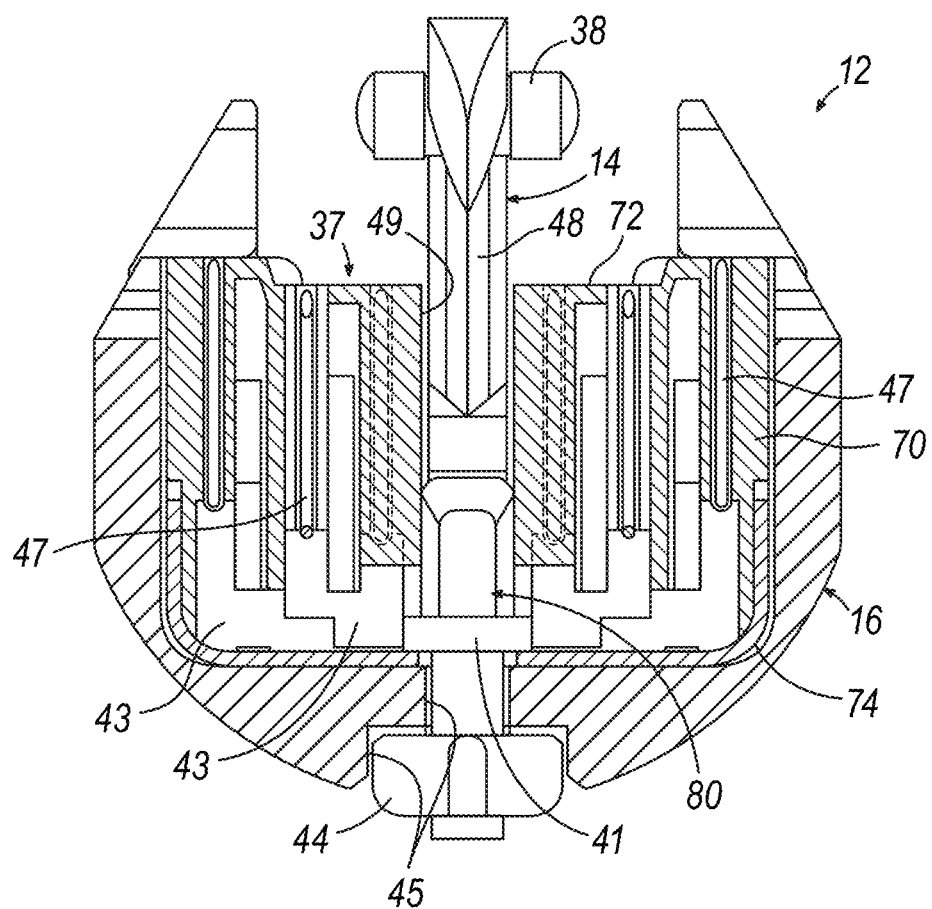
FIG. 5 depicts an end cross-sectional view of the end effector of FIG. 3, taken along line 5-5 of FIG. 3.
Figure 6:
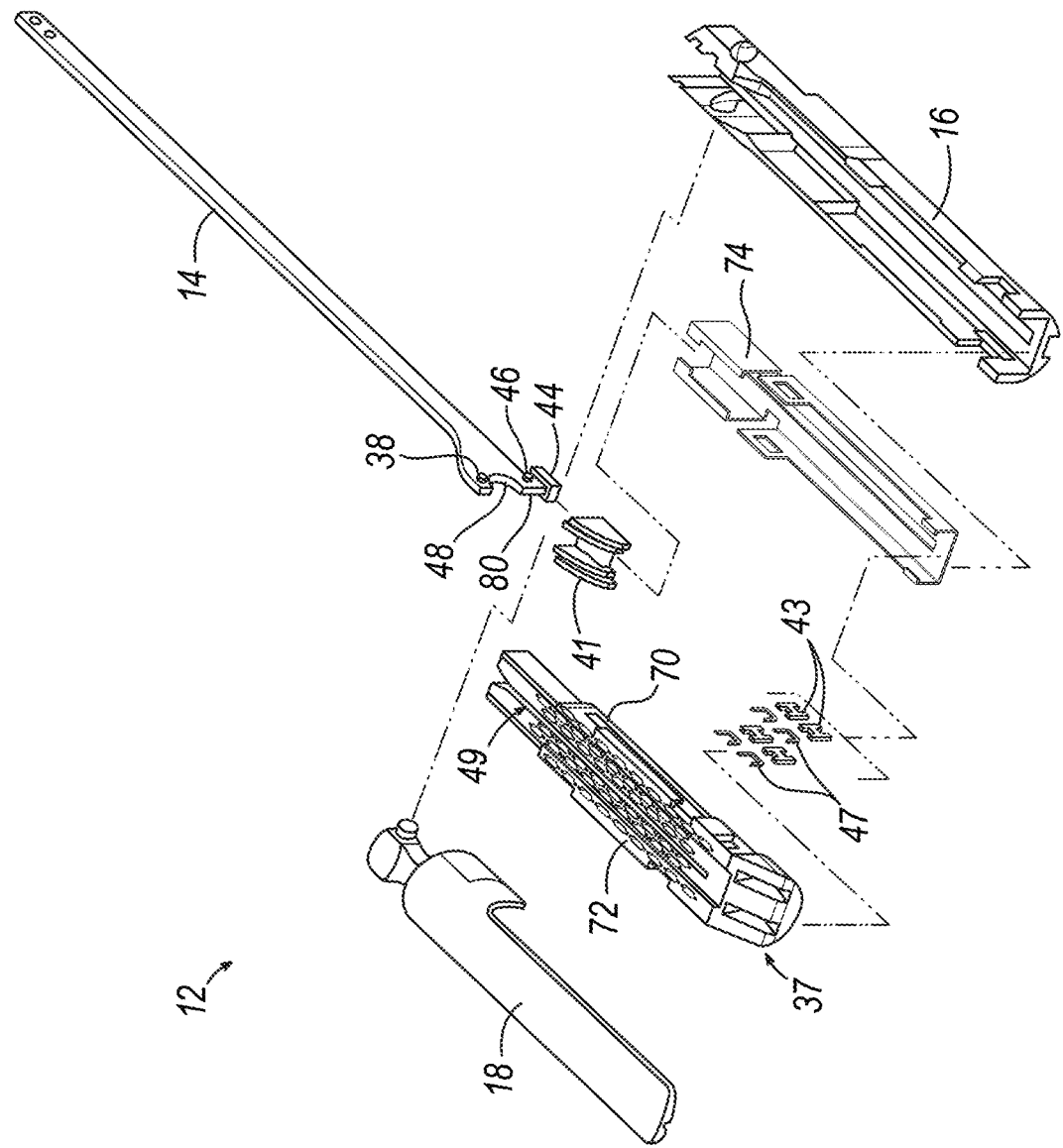
FIG. 6 depicts an exploded perspective view of the end effector of FIG. 3.

FIG. 3 shows firing beam 14 of the present example proximally positioned and anvil jaw 18 pivoted to an open configuration, allowing an unspent staple cartridge 37 to be removably installed into a channel of lower jaw 16. As best seen in FIGS. 5-6, staple cartridge 37 of the present example includes a cartridge body 70, which presents an upper deck 72 and is coupled with a lower cartridge tray 74. As best seen in FIG. 3, a vertical slot 49 extends longitudinally through a portion of staple cartridge body 70. As also best seen in FIG. 3, three rows of staple apertures 51 are formed through upper deck 72 on each lateral side of vertical slot 49. As shown in FIGS. 4A-6, a wedge sled 41 and a plurality of staple drivers 43 are captured between cartridge body 70 and tray 74, with wedge sled 41 being located proximal to staple drivers 43. Wedge sled 41 is movable longitudinally within staple cartridge 37; while staple drivers 43 are movable vertically within staple cartridge 37. Staples 47 are also positioned within cartridge body 70, above corresponding staple drivers 43. Each staple 47 is driven vertically within cartridge body 70 by a staple driver 43 to drive staple 47 out through an associated staple aperture 51. As best seen in FIGS. 4A-4B and 6, wedge sled 41 presents inclined cam surfaces that urge staple drivers 43 upwardly as wedge sled 41 is driven distally through staple cartridge 37.

With end effector 12 closed, as depicted in FIGS. 4A-4B by distally advancing closure tube 32 and closure ring 33, a firing member in the form of firing beam 14 is then advanced distally into engagement with anvil jaw 18 by having upper pin 38 enter longitudinal anvil slot 42. A pusher block 80 (shown in FIG. 5) located at distal end of firing beam 14 pushes wedge sled 41 distally as firing beam 14 is advanced distally through staple cartridge 37 when firing trigger 28 is actuated. During such firing, cutting edge 48 of firing beam 14 enters vertical slot 49 of staple cartridge 37, severing tissue clamped between staple cartridge 37 and anvil jaw 18. As shown in FIGS. 4A-4B, middle pin 46 and pusher block 80 together actuate staple cartridge 37 by entering into vertical slot 49 within staple cartridge 37, driving wedge sled 41 into upward camming contact with staple drivers 43, which in turn drives staples 47 out through staple apertures 51 and into forming contact with staple forming pockets 53 (shown in FIG. 3) on inner surface of anvil jaw 18. FIG. 4B depicts firing beam 14 fully distally translated after completing severing and stapling of tissue. Staple forming pockets 53 are intentionally omitted from the view in FIGS. 4A-4B but are shown in FIG. 3. Anvil jaw 18 is intentionally omitted from the view in FIG. 5.

Figure 7:
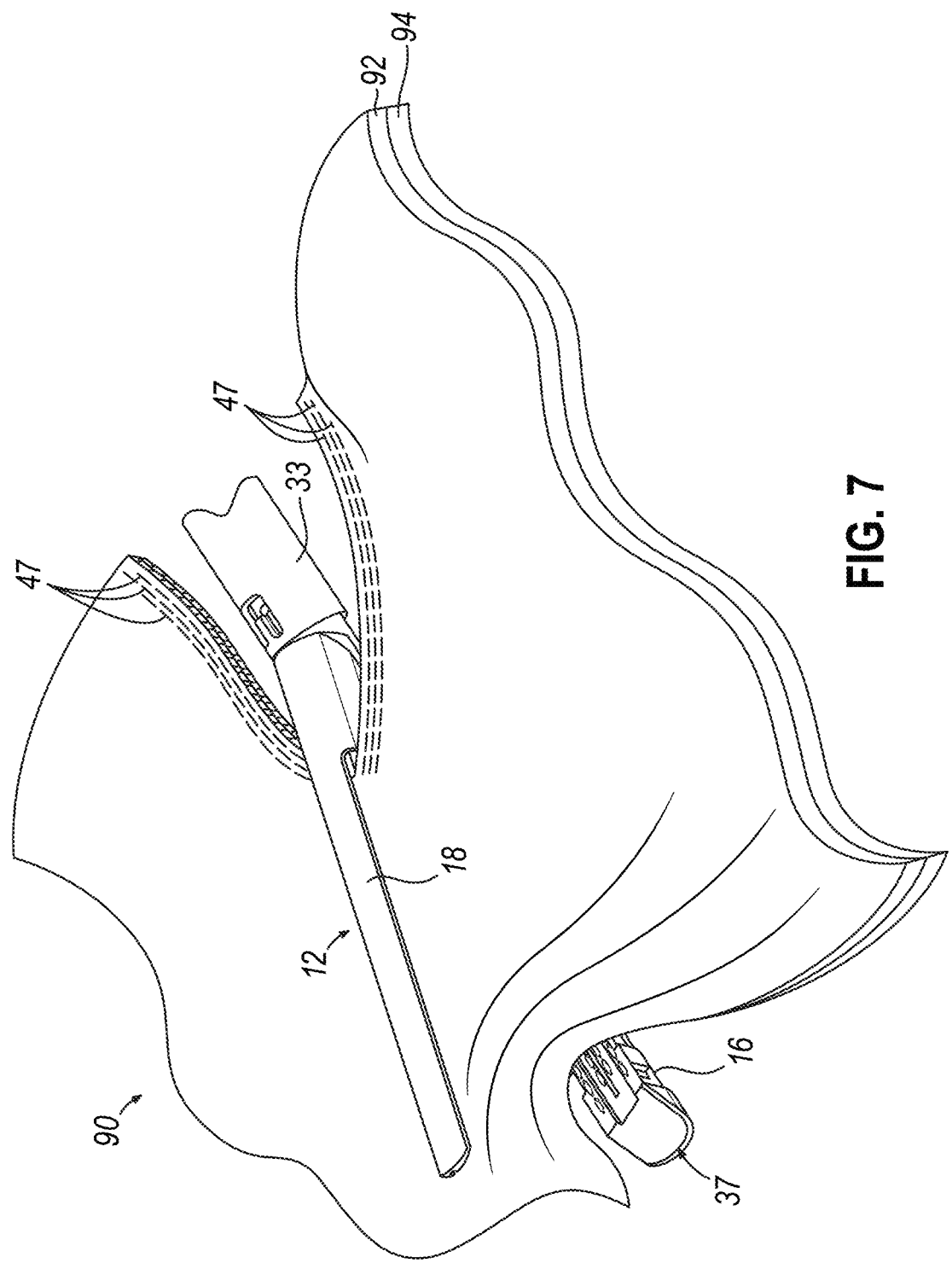
FIG. 7 depicts a perspective view of the end effector of FIG. 3, positioned at tissue and having been actuated once in the tissue.

FIG. 7 shows end effector 12 having been actuated through a single firing stroke through tissue 90. Cutting edge 48 (obscured in FIG. 7) has cut through tissue 90, while staple drivers 43 have driven three alternating rows of staples 47 through tissue 90 on each side of the cut line produced by cutting edge 48. After the first firing stroke is complete, end effector 12 is withdrawn from the patient, spent staple cartridge 37 is replaced with a new staple cartridge 37, and end effector 12 is then again inserted into the patient to reach the stapling site for further cutting and stapling. This process may be repeated until the desired quantity and pattern of firing strokes across the tissue 90 has been completed.

Instrument 10 may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. End Effector with Visualization, Lead-In, and Gathering Feature

In some instances, it may be desirable to provide the user with better visualization of end effector 12. In particular, as end effector 12 is inserted into a surgical site, the user may rotate shaft 22 of instrument 10 during the procedure. As a result, end effector 12 also rotates. As end effector 12 rotates, it may be desirable for the user to have visual access to the surgical site. For instance, the user may wish to see the interface or contact between tissue 90 and end effector 12. Since end effector 12 may be rotated about the longitudinal axis (LA) relative to handle portion 20, the user may view the surgical site such that lower jaw 16 of end effector is visible rather than anvil jaw 18. Alternatively, end effector 12 could be rotated such that when the user views end effector 12, anvil jaw 18 is visible by the user. It may be desirable to provide visibility of the surgical site for the user beyond what is possible in instrument 10 of FIG. 1.

For instance, in the case of some surgical procedures where fluid carrying vessels are transected and stapled, it may be desirable to have visual confirmation that anvil jaw 18 and lower jaw 16 completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector 12 has been positioned properly within the surgical site for upper jaw 18 and lower jaw 16 to fully clamp the vessel. One potential way of monitoring the surgical site may include improving visualization of the area adjacent to the distal tip of lower jaw 16 and upper jaw 18. Furthermore, not only visualization of the distal end of end effector 12 may be desirable, but also it may be desirable to construct end effector 12 such that the distal end of upper jaw 18 is configured to urge tissue (e.g., a large vessel) proximally into the space between upper jaw 18 and lower jaw 16 as upper jaw 18 closes toward lower jaw 16.

Figure 8:
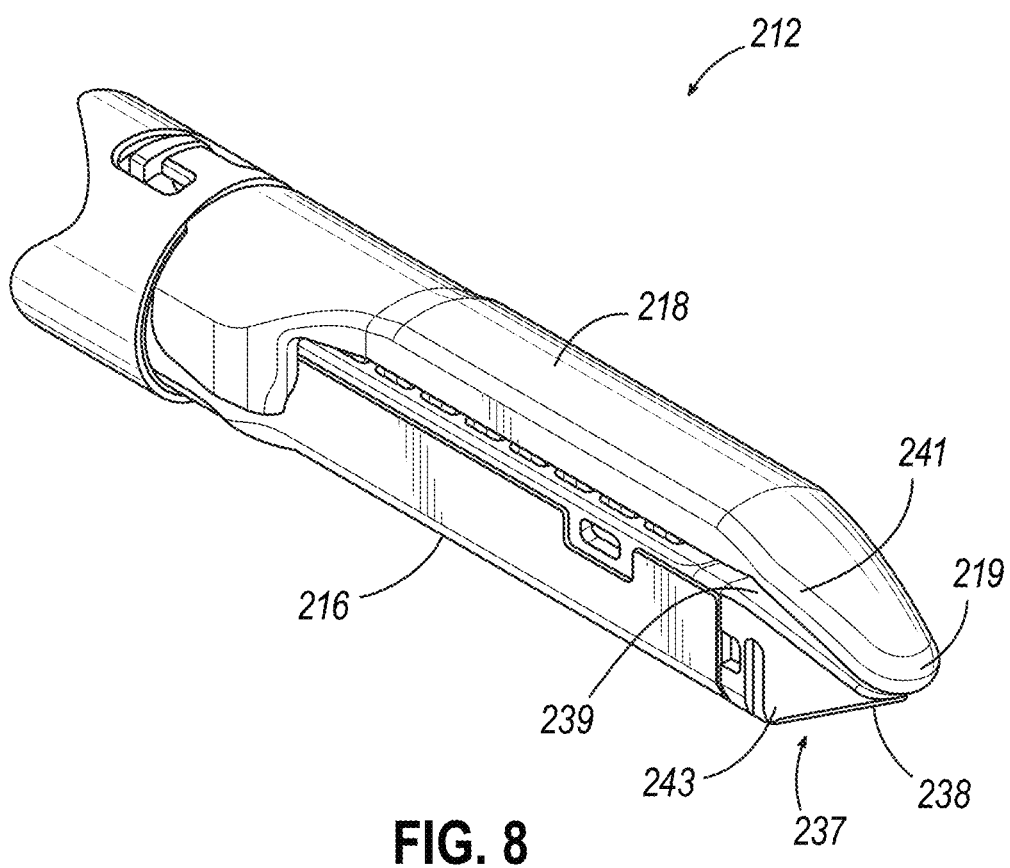
FIG. 8 depicts a perspective view of an alternative version of an end effector with an angled upper jaw and an angled cartridge.

FIG. 8 depicts an example of an end effector 212 comprising an anvil jaw 218 and a lower jaw 216. It will be appreciated that end effector 212 may be used in place of end effector 12 of instrument 10. End effector 212 may be integrally formed with instrument 10 or in the alternative may be interchangeable with end effector 12 of instrument 10.

Anvil jaw 218 is operable to pivot relative to lower jaw 216. Anvil jaw 218 and lower jaw 216 may clamp tissue 90 similarly to clamping performed by anvil jaw 18 and lower jaw 16 shown in FIG. 1. End effector 212 further includes a cartridge 237 operable to be placed in lower jaw 216 similarly to cartridge 37 shown in FIG. 3.

Figure 9:
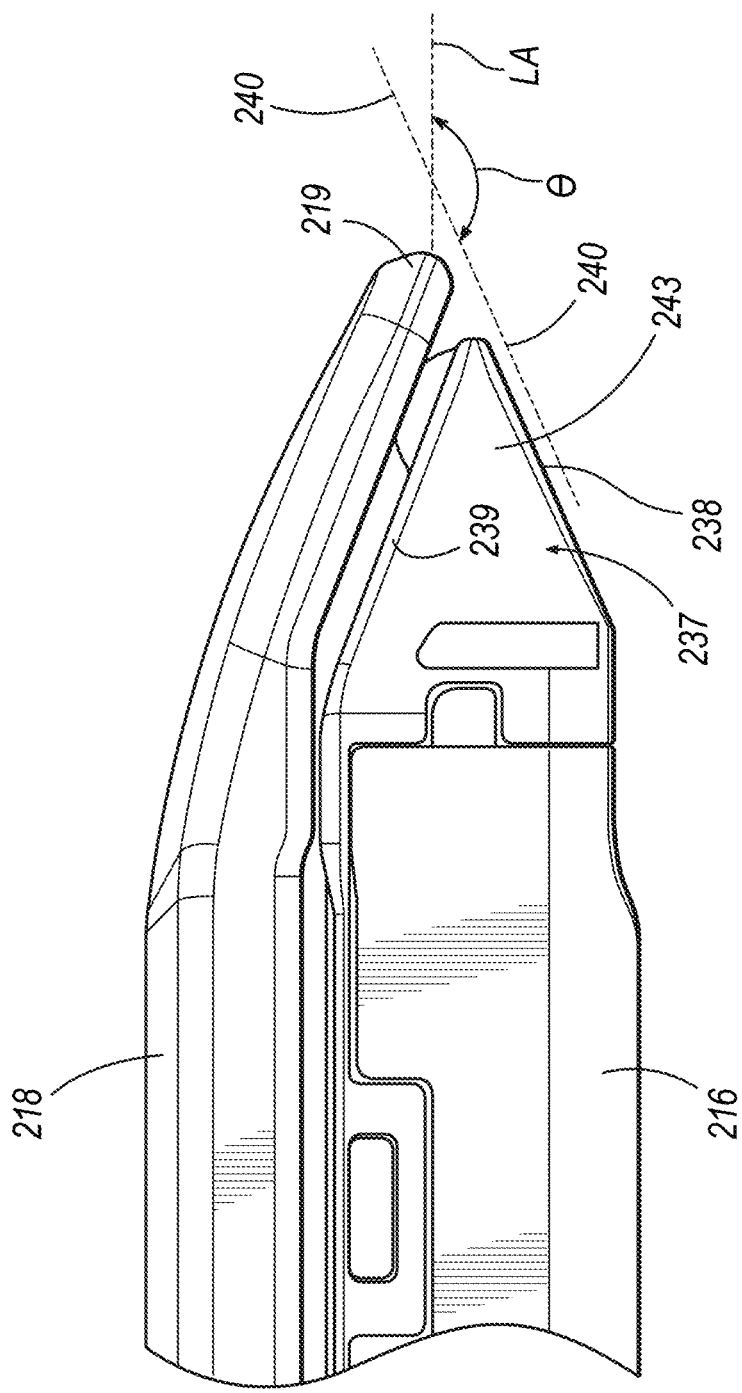
FIG. 9 depicts an enlarged, side view of the end effector of FIG. 8.
Figure 10:
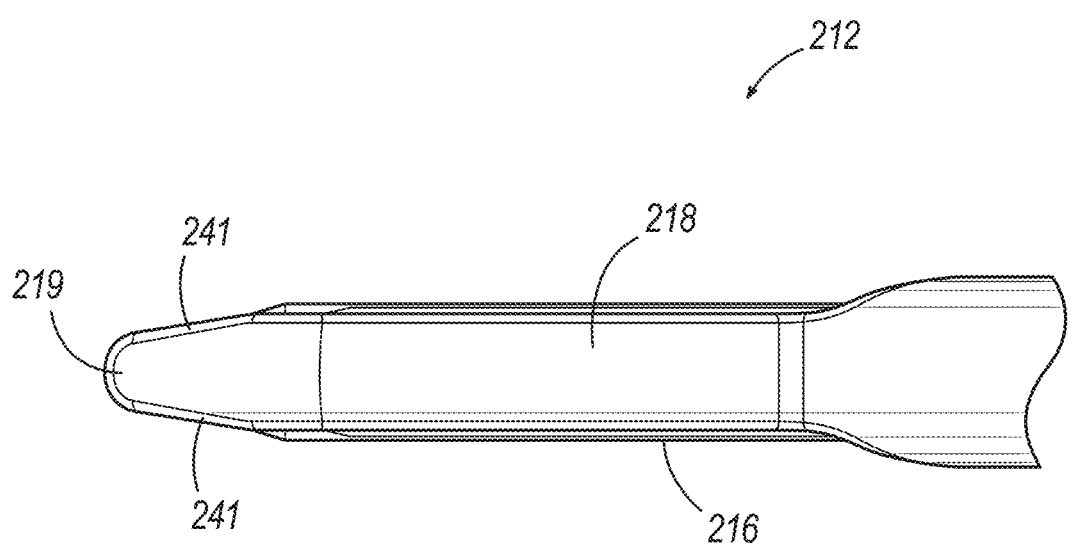
FIG. 10 depicts an enlarged top view of the end effector of FIG. 8.

Anvil jaw 218 as can be seen in FIGS. 8-10 has an elongated shape where the distal portion of anvil jaw 218 angles toward cartridge 237. The distal portion of anvil jaw 218 angles toward cartridge 237 such that the distal most distal tip 219 of anvil jaw 218 extends distally longitudinally further than cartridge 237. Though in some versions, distal tip 219 may extend to a distance longitudinally equal to cartridge 237 or proximal relative to the distal most point on cartridge 237. Furthermore, anvil jaw 218 angles toward cartridge 237 through a gentle slope. As seen best in FIG. 10, anvil jaw 218 includes sides 241 that taper as they approach the distal most distal tip 219 of anvil jaw 218. By way of example, anvil jaw 218 is shaped in FIG. 8 similarly to an inverted ski tip. The angled shape of anvil jaw 218 may provide easier insertion of end effector 212 into a surgical site. For instance, the gentle slope or inverted ski tip shape of anvil jaw 218 may provide an atraumatic tissue deflection surface as anvil jaw 218 contacts or moves through tissue. Such atraumatic tissue deflection may include urging tissue (e.g., a large vessel) proximally into the space between anvil jaw 218 and lower jaw 216 as anvil jaw 218 closes toward lower jaw 216. Once placed into a surgical site, the angled shape of anvil jaw 218 may also provide better maneuverability of end effector 212 and better visibility of the distal end of end effector 212 in relation to anatomical structures at the surgical site. Other suitable variations of anvil jaw 218 will be apparent to one of ordinary skill in the art in view of the teachings herein.

Cartridge 237 is operable to hold staples similar to staples 47 shown in FIG. 4A for driving into tissue. As shown in FIG. 9, the distal end of cartridge 237 has a triangular profile. In particular, the distal end of cartridge 237 includes an upper tapered surface 239 and a lower tapered surface 238. Additionally, the distal end of cartridge 237 includes a tapered side surface 243 on each side. In the present example, each tapered side surface 243 of cartridge 237 generally aligns with the taper presented by sides 241 of anvil jaw 218. Thus, as shown in FIG. 10, side surfaces 243 of cartridge 237 do not extend outwardly from longitudinal axis (LA) of end effector 212 past sides 241 of anvil jaw 218. Upper tapered surface 239 and lower tapered surface 238 lead to the distal most end of cartridge 237. Lower tapered surface 238 defines a sight line 240 such that once end effector 212 is inserted into a surgical site, the user can see along sight line 240. Sight line 240 extends along the edge of lower tapered surface 238. It will be appreciated that the planar shape of lower tapered surface 238 may be operable to allow the user to visualize and/or nearly visualize the distal tip 219 of anvil jaw 218. In particular, sight line 240 intersects longitudinal axis (LA), which extends longitudinally through end effector 212, to form a viewing angle (θ).

Viewing angle (θ) may establish the relative visibility that a user has regarding distal tip 219. In particular, the user can see in front of distal tip 219 along any line of sight that passes through the intersection of sight line 240 and longitudinal axis (LA) within viewing angle (θ). For instance, as viewing angle (θ) increases, the user would have greater visibility of the area immediately in front of distal tip 219 from proximal vantage points; whereas as viewing angle (θ) decreases, the user has less visibility of the area in front of distal tip 219 from proximal vantage points. In some versions, viewing angle (θ) defines an angle greater than 90 degrees. Additionally, in some versions, viewing angle (θ) defines an angle greater than 135 degrees. Other suitable angles for viewing angle (θ) will be apparent to one of ordinary skill in the art in view of the teachings herein. In the illustrated version, the user generally looks along sight line 240 or along some other line of sight within viewing angle (θ), thus, the user has visibility along sight line as well as any area within viewing angle (θ). The underside of distal tip 219 is further slightly rounded to aid in the visibility of the intersection of longitudinal axis (LA) and sight line 240.

When tissue 90 is clamped between a closed cartridge 237 and anvil jaw 218, the user can look along sight line 240 or elsewhere within viewing angle (θ) to see, for instance, precisely where anvil jaw 218 has clamped tissue 90. Furthermore, the user would be able to determine whether the tissue is completely clamped between anvil jaw 218 and cartridge 237 such that tissue does not spill over the end of end effector 212. The user may be able to also visualize the quality of the clamp between anvil jaw 218 and cartridge 237 against tissue 90. It will be appreciated that in some instances, end effector 212 may be rotated before, during, or after clamping tissue 90. As a result, the tapered shape of anvil jaw 218 may also provide more accessible viewing of distal tip 219 or substantially adjacent distal tip 219. The taper of anvil jaw 218 along with lower tapered surface 238 of cartridge 237 may further promote easy insertion of end effector 212 into tissue in an atraumatic manner. Furthermore, it may be easier to fit end effector 212 through a trocar or other devices operable to introduce end effector 212 into a surgical site due to the tapered end of end effector 212. For instance, once distal tip 219 is fit into a trocar, lower tapered surface 238 and the tapered shape of anvil jaw 218 may provide a lead-in, guiding the rest of end effector 212 into the trocar. In view of the teachings herein, those of ordinary skill in the art will further appreciate that visibility and maneuverability can be enhanced by the tapered design for both sides 241 of anvil jaw 218 and each side 243 of cartridge 237.

In addition to the foregoing, end effector 212 and versions of instrument 10 incorporating end effector 212 may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," issued Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pat. No. 10,092,292, entitled "Staple Forming Features for Surgical Stapling Instrument," Oct. 9, 2018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," issued Nov. 7, 2017, the disclosure of which is incorporated by reference herein. Further modifications that may be incorporated into end effector 212 will be described in greater detail below.

III. End Effector with Modular Configuration Feature

Figure 11:
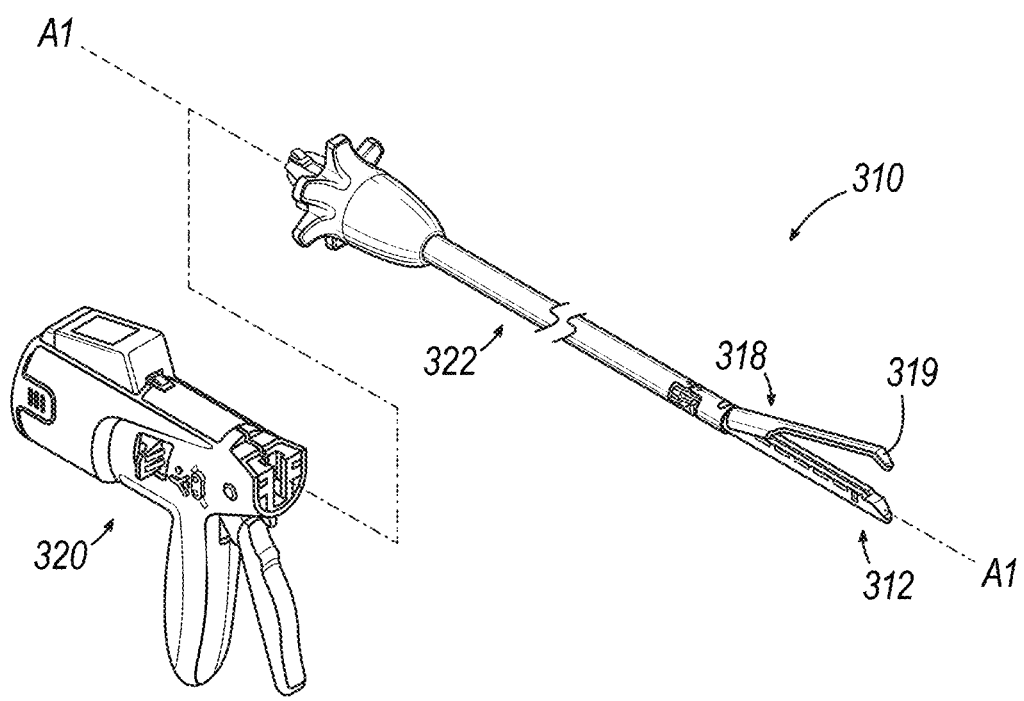
FIG. 11 depicts a perspective view of an example of a surgical stapling instrument having an end effector with a curved elastically deformable tip section.

FIG. 11 shows another example of an instrument 310 configured as a surgical stapler. Instrument 310 includes a handle portion 320 and a shaft 322. Instrument 310 has a modular configuration such that shaft 322 is selectively removable from, and attachable to, handle portion 320. Instrument 310 is configured similarly to instrument 10 such that the operability and use of instrument 310 is the same as described above for instrument 10 with the added feature of instrument 310 being a modular configuration. With its modular configuration, instrument 310 provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument 310 may be configured in accordance with at least some of the teachings of U.S. Pat. No. 10,182,813, entitled "Surgical Stapling Instrument with Shaft Release, Powered Firing, and Powered Articulation," issued Jan. 22, 2019, the disclosure of which is incorporated by reference herein. Other suitable components, features, and configurations for providing instrument 310 with a modular configuration will be apparent to those of ordinary skill in the art in view of the teachings herein. Moreover, it will be understood by those of ordinary skill in the art in view of the teachings herein, that instrument 10 may be modified to incorporate a modular configuration as shown and described with respect to instrument 310 or other instruments incorporated by reference herein.

In the illustrated example of FIG. 11, instrument 310 includes an end effector 312 having an anvil jaw 318 that has an angled distal tip 319.

It will be appreciated that end effector 312 may be used in place of end effector 12 shown in FIG. 1. In some versions, end effector 312 may be integrally formed with shaft 22 or alternatively may be separately formed and then combined. In some versions, end effector 312 may be provided for use in robotic systems. In such robotic systems, modular shaft 322 having end effector 312 may be attachable to a portion of the robotic system for use such that handle portion 320 is replaced by components of the robotic system. Still in other examples, end effector 312 may be adapted for use with a robotic system in a manner where end effector 312 connects with the robotic system without necessarily connecting the entire modular shaft 322. In view of the teachings herein, other ways to incorporate an end effector having an angled elastically deformable anvil tip into a user operated or robotic operated instrument will be apparent to those of ordinary skill in the art.

IV. End Effector with Continuous Track of Tissue Gap Feature

Augmented sensing, feedback, and connectivity are desired for both robotic and handheld instruments used in laparoscopic surgeries. The surgical stapling features of the present disclosure seek to enhance preoperative planning, surgical performance, therapeutic support, and training to improve patient outcomes and reduce harm. In particular, the surgical stapling features of the present disclosure augment and enhance a user's, e.g., a surgeon or a robotic system, perception of a tissue by providing feedback regarding characteristics of the surgical instrument and tissue to help inform intraoperative decisions based on data sensed, obtained, and transmitted by a sensor assembly installed in the end effector of a surgical instrument.

Figure 12:
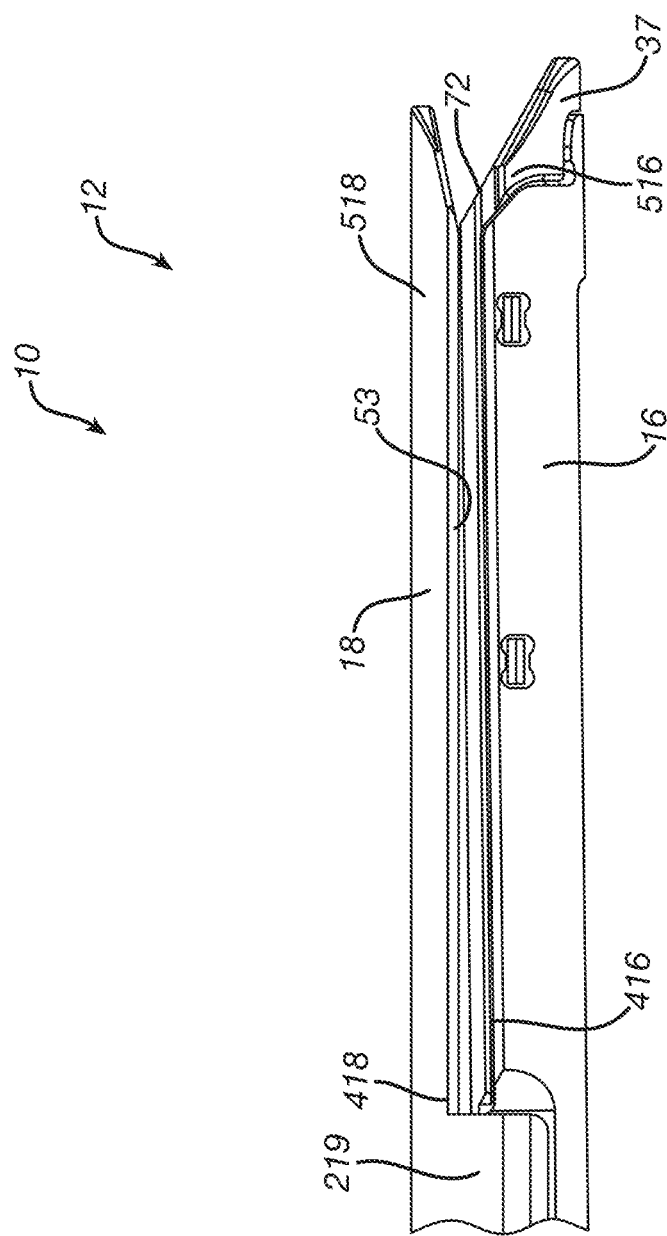
FIG. 12 depicts a side view of a surgical stapling instrument according to one embodiment.

As shown in FIG. 12, in various embodiments, an end effector 12 of a surgical stapling instrument 10 comprises an anvil jaw 18 and a cartridge jaw 16. The anvil jaw 18 comprises a proximal end 418 and a distal end 518 where the proximal end 418 is rotatably mounted to the cartridge jaw 16 and is rotatable relative to the cartridge jaw 16 between an open, or unclamped, position and a closed, or clamped, position. The surgical stapling instrument 10 may further comprise an anvil tissue stop 218 to prevent patient tissue from moving proximally into the end effector 12 where the tissue may accidentally contact the cutting edge 48 in its proximal unactuated position. The anvil jaw 18 of the surgical stapling instrument 10 is a long slender jaw member that tends to deflect upwardly when clamped onto thick tissues. On thick tissue, this upward deflection of the free (distal) end 518 of the anvil jaw 18 can cause differences in height of the formed staples as the distal gap or distance between the anvil jaw 18 and the cartridge jaw 16 is larger than the proximal gap.

Figure 13:
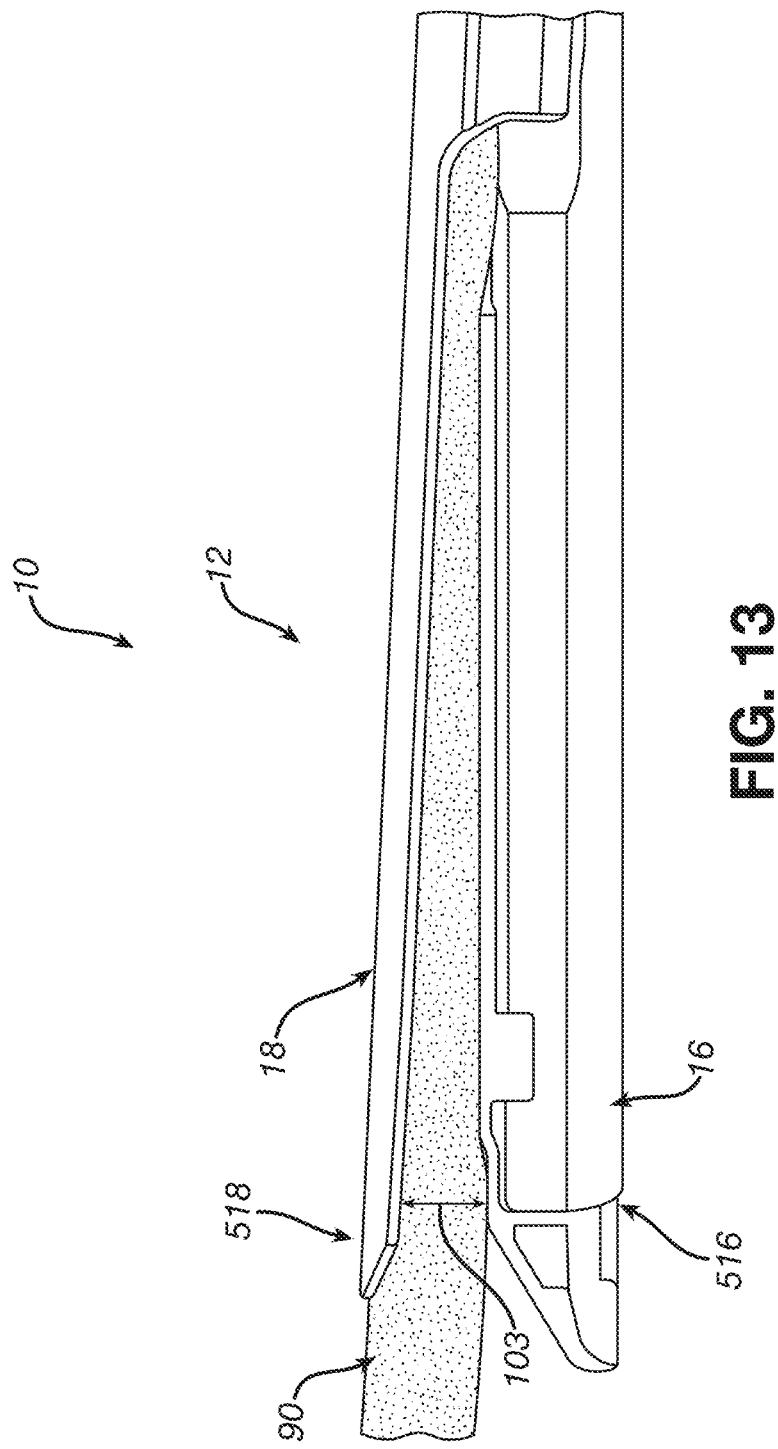
FIG. 13 depicts a side view of a surgical stapling instrument according to one embodiment.
Figure 14:
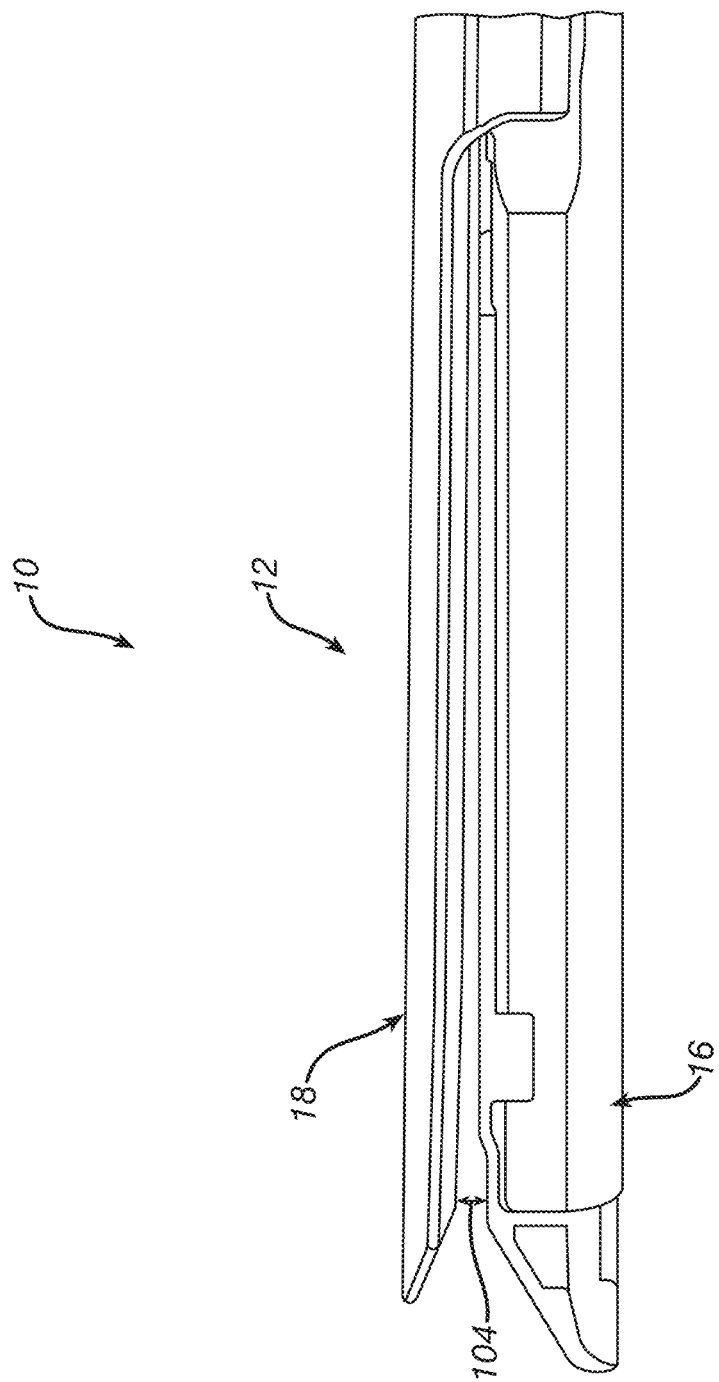
FIG. 14 depicts a side view of a surgical stapling instrument according to one embodiment.

In particular, as shown in FIGS. 12-14, as the anvil jaw 18 is being used, the anvil 18 may deform, i.e., bend/arch upwards, instead of maintaining a straight line, due to the substantial forces applied to clamp and fire the surgical stapling instrument 10 and the thickness/resistance of the tissue being transected. After each use, some amount of deformation of the anvil 18 may remain and this deformation may accumulate over repeated uses of the instrument.

Specifically, to account for at least a portion of the deformation, during manufacturing, as shown in FIGS. 12-14, a downward (positive) camber, i.e., a convexity, arching, or curvature, may be applied to the anvil jaw 18 to counter for at least some the upward bending of the distal tip of the anvil jaw 18 during the use of the surgical stapling instrument 10. In other words, the distal tip of the anvil jaw 18 may be positively cambered or bent inwardly (downward) toward the staple cartridge 37. In some cases, the camber applied to the anvil jaw 18 prevents, or at least inhibits, the tissue 90 captured between the anvil jaw 18 and the staple cartridge 37 from flowing out of the distal end 518 of the end effector 12.

Instead of using several sensors disposed along the jaws 18, 16, the disclosed embodiments enable using one location, e.g., using sensors disposed in one location (distal ends 518 and 516) of the end effector 12, to measure characteristics of the tissue 90 such as thickness. In particular, the disclosed embodiments use sensors located at the distal ends 518 and 516 of the anvil and cartridge jaws, 18, 16 to measure the amount of tissue 90 grasped therein by measuring a distance 103, i.e., a gap between the distal ends 518 and 516 when the jaws 18, 16 are closed with tissue 90 grasped therebetween. As shown in FIG. 14, the disclosed embodiments may further use the sensors and the anvil and cartridge jaws 18, 16 to measure a baseline distance 104, i.e., a gap between the distal ends 516 and 518 of the anvil and cartridge jaws 18, 16 for an empty surgical stapling instrument 10, e.g., for when the jaws 18, 16 are closed with no tissue grasped therebetween. The thickness of the tissue 90 may be derived from the measurement of the distance 103 and adjusted for the baseline distance 104.

However, the measurements of characteristics of the tissue may be affected by the camber of the anvil jaw 18 particularly when such measurements are made at the distal ends of the jaws 18, 16 as will be described. There may also be camber variations between each manufactured end effector 12. Further, the camber of the anvil jaw 18 may continuously change due to the load or force applied to the anvil jaw 18 when clamping or firing along tissue 90. In particular, the anvil 18 may experience de-camber, i.e., the tip of the anvil jaw 18 may bend upwardly (negative camber), after each firing along the clamped tissue 90, and this de-camber may accumulate over repeated uses. The change in camber or de-camber of the anvil jaw 18 may affect the accuracy of the measurement of the thickness of the tissue 90 after each firing.

For example, as shown in FIG. 13, due to the proximal pivot location, even if the end effector 12 is clamped on a uniform piece of tissue 90, the anvil jaw 18 may be angled relative to the lower jaw. The camber and de-camber of the anvil jaw 18 may cause a change in the distance 103 between distal ends of the anvil jaw 18 and the cartridge jaw 16 after each firing, therefore affecting the accuracy of the measurement of the amount of tissue grasped therein.

Therefore, it may be desirable to provide the user with an accurate measurement of the amount of tissue 90 grasped indicative of the thickness of the tissue therein to control the firing (e.g., the timing, cutting edge force, and cutting edge speed). The disclosed embodiments provide adjustment and compensation for the current camber of the jaws 18, 16, while measuring the amount of grasped tissue 90 to control the firing, e.g., firing timing, cutting edge speed and/or force, both before and during firing.

The disclosed embodiments provide a surgical stapling instrument 10 comprising first and second jaws 18, 16, a sensor assembly, and a controller. The controller detects that the jaws 18, 16 have been actuated from closed position to open position and back to closed position, and derives, from a first signal from the sensor assembly, a current distance between the distal ends of the jaws. Upon determining firing immediately preceding actuation of the jaws, the controller adjusts a camber adjustment value based on the current distance and determines a de-camber value. Upon determining no firing immediately preceding actuation of the jaws and closing of the jaws with tissue grasped, the controller adjusts the tissue thickness measurement based on the camber adjustment value and controls the next firing based thereon. Upon determining no firing immediately preceding actuation of the jaws and that closing of the jaws with no tissue grasped therein, the controller adjusts the camber adjustment value based on the current measurement of the distance.

In particular, the disclosed embodiments determine whether the jaws 18, 16 are closed with grasped tissue therein, track the anvil camber and de-camber information, measure the amount of grasped tissue 90 (indicative of thickness of the tissue 90), adjust the measured amount of tissue 90 grasped using the anvil camber information, and provide feedback to control a firing of the surgical stapling instrument 10. Further, with fine-tuned calibration, the disclosed embodiments may also estimate the location of the grasped tissue 90 within the jaws, i.e., where, between the proximal and distal ends of the jaws, tissue is present or not.

Further, the disclosed embodiments use a one location measurement of a distance 103 of the first and second jaws 18, 16 and determine and track current and previous statuses of the surgical stapling instrument 10 including "Dry Clamp" (jaws 18, 16 are closed with no tissue grasped therein), "Clamp on Tissue" (jaws 18, 16 are closed with tissue grasped therein), and "Firing" (transecting of tissue 90) to determine anvil camber, de-camber, and an adjusted measurement of the amount of grasped tissue 90 to control the firings. Further status of the surgical stapling instrument 10 may include "Open" (jaws 18, 16 are open), and "Reload" (loading a staple cartridge 37).

In particular, the disclosed embodiments determine a camber adjustment value by determining the distance 104, i.e., a distance or gap, of the distal end 518 of the anvil jaw 18 to a distal end 516 of the cartridge jaw 16, when the jaws 18, 16 are repeatedly opened and closed or clamped together when there is no tissue grasped therein. In other words, the distance 104 may be indicative of the camber of the anvil jaw 18 when the first and second jaws 18, 16 are closed when there is no tissue grasped therebetween.

Further, the disclosed embodiments measure an amount of tissue 90 grasped by detecting the distance 103 between the distal ends 518, 516 of the jaws 18, 16 when the jaws 18, 16 are closed or clamped together with tissue 90 grasped therebetween (Status="Clamp on Tissue") and adjusts the measurement of the amount of tissue 90 grasped based on the camber adjustment value. In particular, the disclosed embodiments may subtract the camber adjustment value from the measurement of the amount of tissue 90 grasped.

In various embodiments, when the first and second jaws 18, 16 are in the closed position with tissue grasped therein, the distance 103 may be indicative of a characteristic of the tissue 90, such as tissue 90 thickness. The disclosed embodiments adjust the tissue 90 thickness based on the camber adjustment value.

Figure 15:
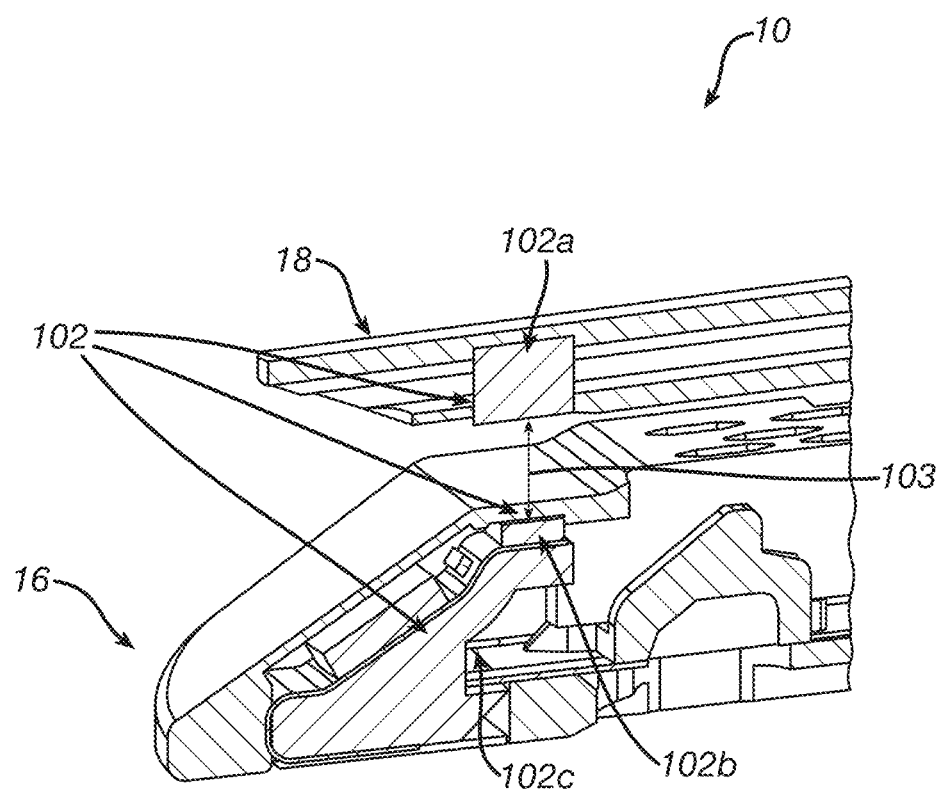
FIG. 15 depicts a side cross-sectional view of a surgical stapling instrument according to one embodiment.
Figure 16:
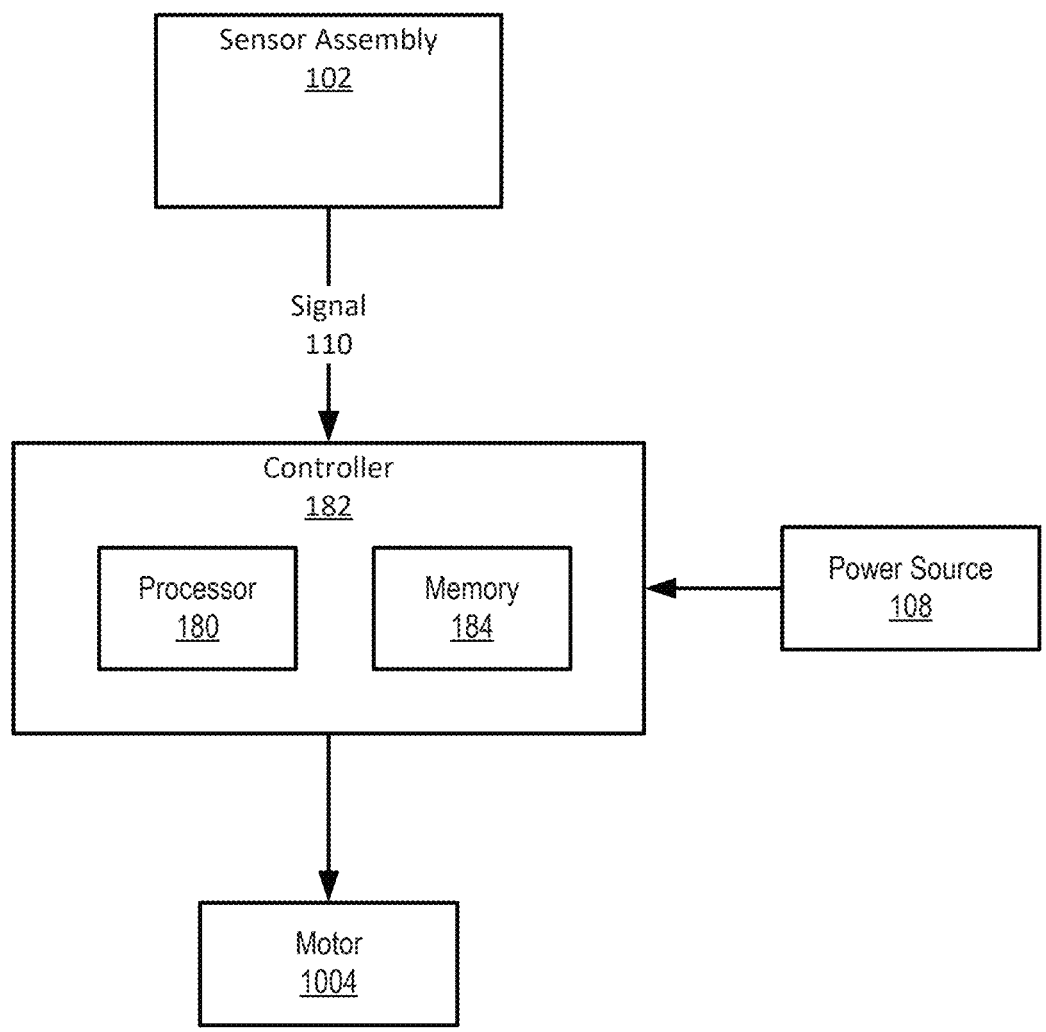
FIG. 16 depicts a diagram of a controller according to one embodiment.

In various embodiments, as shown in FIGS. 12, 15 and 16, an end effector 12 for use with a surgical stapling and severing instrument 10, i.e., a surgical stapler 10, is disclosed. The end effector 12 comprises a first jaw 18, (i.e., an upper jaw, an anvil jaw 18) and a second jaw 16 (i.e., a lower jaw, a cartridge jaw 16). The first jaw 18 is coupled at a proximal end 418 thereof with the second jaw 16 so as to be pivotable between an open position and a closed position for grasping tissue 90 therebetween.

Figure 30:
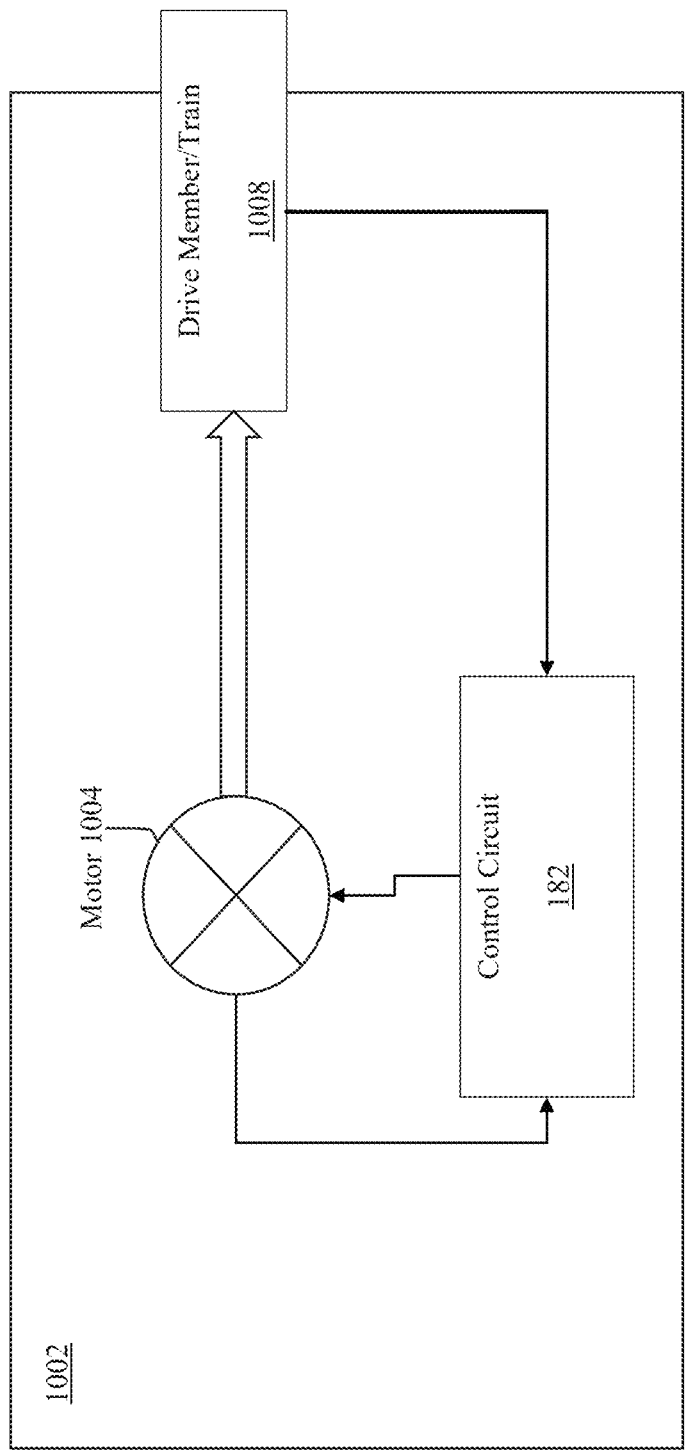
FIG. 30 depicts a block diagram for operating a surgical stapling instrument according to one embodiment.

As shown in FIGS. 16 and 30, as further described below, the surgical stapling instrument 10 may include a motor 1004 located external to the end effector 12. The motor 1004 may be any suitable motor, electrically powered or otherwise by a power source (not shown) and which may provide for a rotational or linear actuation to displace/advance a driver/drive train 1008 of the instrument 10. The drive train 1008 may comprise multiple linked driving and/or driven components, including the drive member which longitudinally extends through the shaft 22 as was described above, which translate the displacement and force applied by the motor 1004 to the cutting edge 48.

The surgical stapling instrument 10 may further include the driver/drive train 1008 operably coupled between the motor 1004 and the cutting edge 48, and thereby the sled 41, wherein the motor 1004 is configured to controllably displace, e.g., advance, move or push, either rotationally or linearly, a position of a proximal end of the drive train 1008, to which the motor 1004 may be mechanically/electro-mechanically coupled, a controllable distance to thereby displace the cutting edge 48 and thereby, directly or indirectly, the sled 41, so as to substantially simultaneously transect the tissue grasped by the end effector 12 and deploy the staples 47 therein along, and on either side of, the transection. In certain instances, a surgical stapling instrument 10 may include dedicated motor drivers and/or motors for firing, closure, and/or articulation.

The surgical stapling instrument 10 may further comprise a staple cartridge 37 and a shaft 22 extending proximally from an articulation joint as shown in FIGS. 1-7. The staple cartridge 37 comprises staples deployable into the tissue 90. The articulation joint is configured to facilitate articulation of the end effector 12 relative to the shaft 22.

The surgical stapling instrument 10 may further include a sensor assembly 102 disposed at a distal end of the end effector 12 and a controller 182 which is shown in more detail in FIG. 16.

The sensor assembly 102 is configured to sense a proximity of a distal end of the first jaw 18 to a distal end of the second jaw 16, in response to closing or clamping the first and second jaws 18, 16 together and generate a first signal indicative thereof. The sensor assembly 102 may include a magnet 107 disposed at a distal end of the first jaw 18 or the second jaw 16, and a magnetic sensor 106 disposed at the distal end of an opposite first jaw 18 or second jaw 16. In other words, in various embodiments, as shown in FIG. 15, the magnet 102a may be disposed at the distal end of the first jaw 18 and the magnetic sensor 102b, e.g., a hall sensor, may be disposed at the distal end of the second jaw 16. In various embodiments (not shown), the magnet 102a may be disposed at the distal end of the second jaw 16 and the magnetic sensor 102b may be disposed at the distal end of the first jaw 18. In particular, the magnetic sensor 106 may be configured to be aligned with the magnet 102a so as to sense a magnetic field emitted by the magnet 102a indicative of a proximity which is indicative of the actual sensed distance between the distal end 518 of the first jaw 18 and the distal end 516 of the second jaw 16. In various embodiments, the sensor assembly 102 may further include supporting electronics 102c to convert the sensed proximity to the signal 110 indicative thereof and transmit that signal to a control circuit or controller 182. Alternatively, the supporting electronics 102c may be located remotely from the magnet 102a and the magnetic sensor 102b. In some embodiments, the sensor assembly 102 may integrated with the controller 182.

In some embodiments, not shown, the controller 182 may be located at the handle portion 20 which would be connected to the second jaw 16 by a conductive trace along or through the shaft 22. In other embodiments, as shown in FIG. 15, the controller 182 may be located at the distal end 516 of the end effector 12. In other embodiments, not shown, the controller may be located at the proximal end of the end effector 12 or the shaft 22.

In the illustrated example in FIG. 16, the controller 182 is a control circuit and comprises one or more processors 180 (e.g., microprocessor, microcontroller) coupled to at least one non-transitory memory 184. The memory 184 stores machine-executable instructions that, when executed by the processor 180, cause the processor 180 to implement various processes or algorithms described herein. The processor 180 may be any one of a number of single-core or multicore processors known in the art. The memory 184 may comprise volatile and non-volatile storage media. The processor 180 may include an instruction processing unit and an arithmetic unit. The controller 182 may be configured to receive instructions from the memory 184 of this disclosure. The controller 182 may comprise analog or digital circuits such as, for example, programmable logic devices (PLD), field programmable gate arrays (FPGA), discrete logic, or other hardware circuits, software, and/or firmware, or other machine executable instructions to perform the functions explained in the present description. The processor 180 may operate according to a duty cycle which may be based on a clock rate of the processor, the duty cycle defining a frequency with which the processor may sample data or otherwise perform and/or repeat computations, e.g., with updated data.

Further to the above, the sensor assembly 102 is in signal communication with the controller 182 and communicates the first signal 110 to the controller 182. The controller 182 may derive, from the first signal 110, a current measurement of a distance between the distal end 518 of the first jaw 18 and the distal end 516 of the second jaw; and store, in the non-transitory memory 184, the current measurement of the distance.

Further, the controller 182 may be in signal communication with the motor 114 located external to the end effector 12, e.g., with a motor driver (not shown), a feedback system (not shown), and a power source 108 (e.g. a battery, a super capacitor, or any other suitable energy source), and other force sensors (not shown) which, as described below, may sense the force/torque applied to the clamped tissue 90. In certain instances, the controller 182 may control the motor 114 to control the firing, e.g., the force and speed of the cutting edge 48, based on the adjusted measurement of the thickness of the tissue 90 and the de-camber information.

Figure 17:
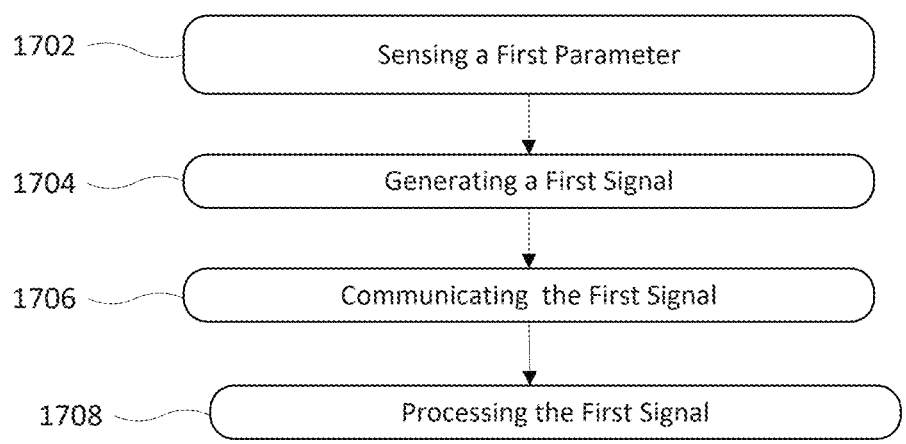
FIG. 17 depicts a flowchart of operating a surgical stapling instrument according to one embodiment.

FIG. 17 depicts a flowchart of the operation 1700 of the sensor assembly 102 and the controller 182 shown in FIG. 16 in response to the operations shown in flowcharts 1800, 1900, and 2000 shown in FIGS. 18-20, which are further described below, according to various embodiments.

As shown in FIG. 17, the operation 1700 of the sensor assembly 102 and the controller 182 may include: sensing, by the sensor assembly 102, a distance 103, 104 of a distal end of the first jaw 18 to a distal end of the second jaw 16, in response to closing of the jaws 18, 16 together (Block 1702); generating, by the sensor assembly 102, a first signal 110 indicative thereof (Block 1704); and communicating, by the sensor assembly 102, the first signal 110 to the controller 182 (Block 1706). The operation 1700 may further include: processing, by the controller 182, the first signal 110 to derive a current measurement of the distance 103, 104 (Block 1708).

Figure 18:
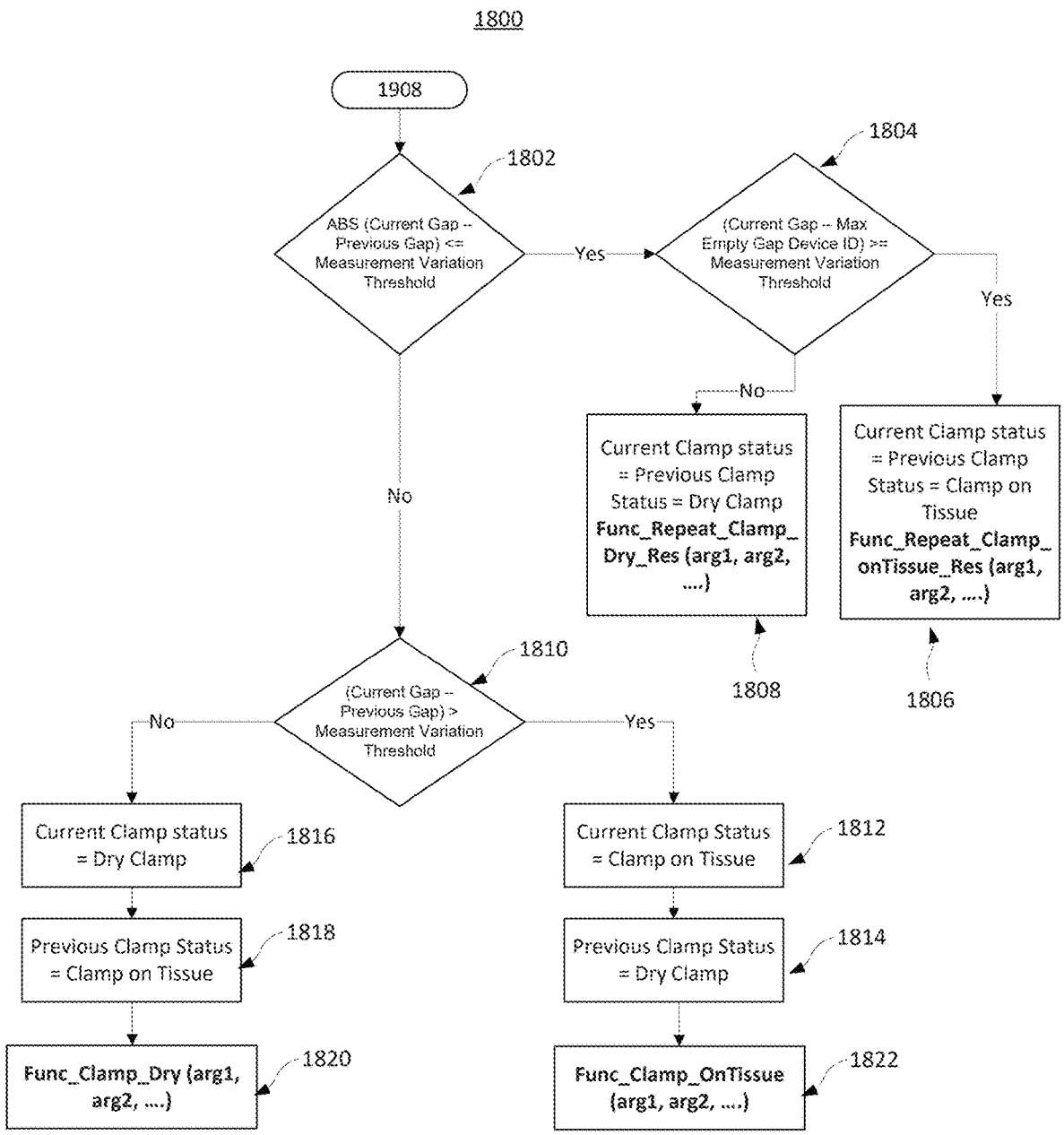
FIG. 18 depicts a flowchart of operating a surgical stapling instrument according to one embodiment.

FIG. 18 depicts a flowchart of the operation 1800 of the controller 182 performed upon detecting, by the controller, that the first and second jaws 18, 16 have been actuated from the closed position to the open position and back to the closed position and detecting, by the controller 182, that the surgical stapling instrument 10 was not fired immediately preceding the actuation. The operation 1800 detects whether the first and second jaws 18, 16 are closed with tissue 90 or with no tissue grasped therein. Depending on whether the first and second jaws 18, 16 were closed with tissue 90 or with no tissue 90 grasped therein, the distance 103, 104 between the distal end 518 of the first 18 and the distal end 516 of the second 16 jaw is indicative of either the camber adjustment value ("Dry Clamp") (Distance 103 as shown in FIG. 13) or the measurement of the thickness ("Clamp on Tissue") (Distance 104 as shown in FIG. 14).

In some embodiments, as further explained below, the controller 182 is configured to determine whether the current and previous measurement of the distance are approximately the same.

In particular, the operation 1800 includes one of: (1) determining that a difference between the current measurement of the distance and the previous measurement of the distance does not exceed a measurement variation threshold, which in some embodiments refers to a threshold representing an amount of a difference that may be tolerated by the surgical stapling instrument 10, (Block 1802) and that the current measurement of the distance exceeds a predefined distance value ("Max Empty Gap Device ID" which refers to a predefined measurement of the maximum expected gap for a particular device type when clamped dry, i.e., when the first and second jaws 18, 16 have been actuated from the closed position to the open position with no tissue therebetween. In some embodiments, the measurement variation threshold may vary between about 0.010 inch and 0.020 inch. In other words, in some embodiments, any change of camber greater than the measurement variation threshold, e.g., about 0.010 inch, would be something to be concerned about. This predefined measurement may vary depending on the type end effector 12 or surgical stapling instrument 10 (Block 1804) and based thereon, determining that the first and second jaws are closed with tissue grasped therebetween (Block 1806) (Current Clamp status=Previous Clamp Status="Clamp on Tissue"); (2) determining that the difference between the current measurement of distance and the previous measurement of the distance does not exceed a measurement variation threshold (Block 1802) and that the current measurement of the distance does not exceed the predefined distance value, and based thereon (Block 1804), determining that the first and second jaws are closed with no tissue grasped therebetween (Block 1808) (Current Clamp status=Previous Clamp Status="Dry Clamp"); (3) determining that the difference between the current measurement of the distance and the previous measurement of the distance exceeds the measurement variation threshold (Block 1802) and that the current measurement of the distance exceeds the previous measurement of the distance (Block 1810), and based thereon, determining that the first and second jaws are closed with tissue grasped therebetween (Blocks 1812, 1814, 1822)) (Current Clamp Status="Clamp on Tissue", Previous Clamp Status="Dry Clamp"); or (4) determining that the difference between a current measurement of the distance and the previous measurement of the distance exceeds a measurement variation threshold (Block 1802) and that the current measurement of the distance does not exceed the previous measurement of the distance (Block 1810), and based thereon, determining that the first and second jaws are closed with no tissue grasped therebetween (Blocks 1818, 1818, and 1820).

In particular, the operation 1800 includes, upon determining, by the controller 182, that the difference in the distance 103 is less than or equal to a measurement variation threshold, determining, by the controller 182, whether the current measurement of the distance 103 minus the "Max Empty Gap Device ID" is greater than or equal to the measurement variation threshold ((Current Gap−"Max Empty Gap Device ID")>=Measurement Variation Threshold)) (Block 1804).

Upon determining, by the controller 182, that the current measurement of the distance 103 minus the "Max Empty Gap Device ID" is greater than or equal to the measurement variation threshold, the controller 182 determines that the first and second jaws 18, 16 are in the closed position with tissue 90 grasped therein (Block 1806).

Upon determining, by the controller 182, that the current measurement of the distance 103 minus the "Max Empty Gap Device ID" is less than the measurement variation threshold, the controller 182 determines that the first and second jaws 18, 16 are in the closed position with no tissue 90 grasped therein (Block 1808).

In some embodiments, as further explained below with respect to Blocks 1810-1818, the controller 182 is configured to determine that the current and previous measurement of the distance 103 are not approximately the same, i.e., either the current measurement of the distance 103 is bigger than the previous measurement of the distance 103 and the first and second jaws 18, 16 are closed with tissue 90 grasped (Current Status="Clamp on Tissue", Previous Status="Dry Clamp") (Blocks 1812 and 1814), or the current measurement of the distance 103 is less than the previous measurement of the distance 103 and the first and second jaws 18, 16 are closed with no tissue 90 grasped (Current Status="Dry Clamp", Previous Status="Clamp on Tissue") (Blocks 1816 and 1818).

In particular, the operation 1800 further includes, upon determining, by the controller 182, that the change in the distance 103 is not less than or equal to, i.e., greater than, a measurement variation threshold, determining, by the controller 182, whether the change in the distance 103 is greater than the measurement variation threshold (Block 1810).

Upon determining, by the controller 182, that the change in the distance 103 is greater than the measurement variation threshold, the controller 182 determines that the first and second jaws 18, 16 are in the closed position with tissue grasped therein (Block 1812).

Upon determining, by the controller 182, that the change in the distance 103 is less than the measurement variation threshold, the controller 182 determines that the first and second jaws 18, 16 are in the closed position with no tissue grasped therein (Block 1816).

Figure 19:
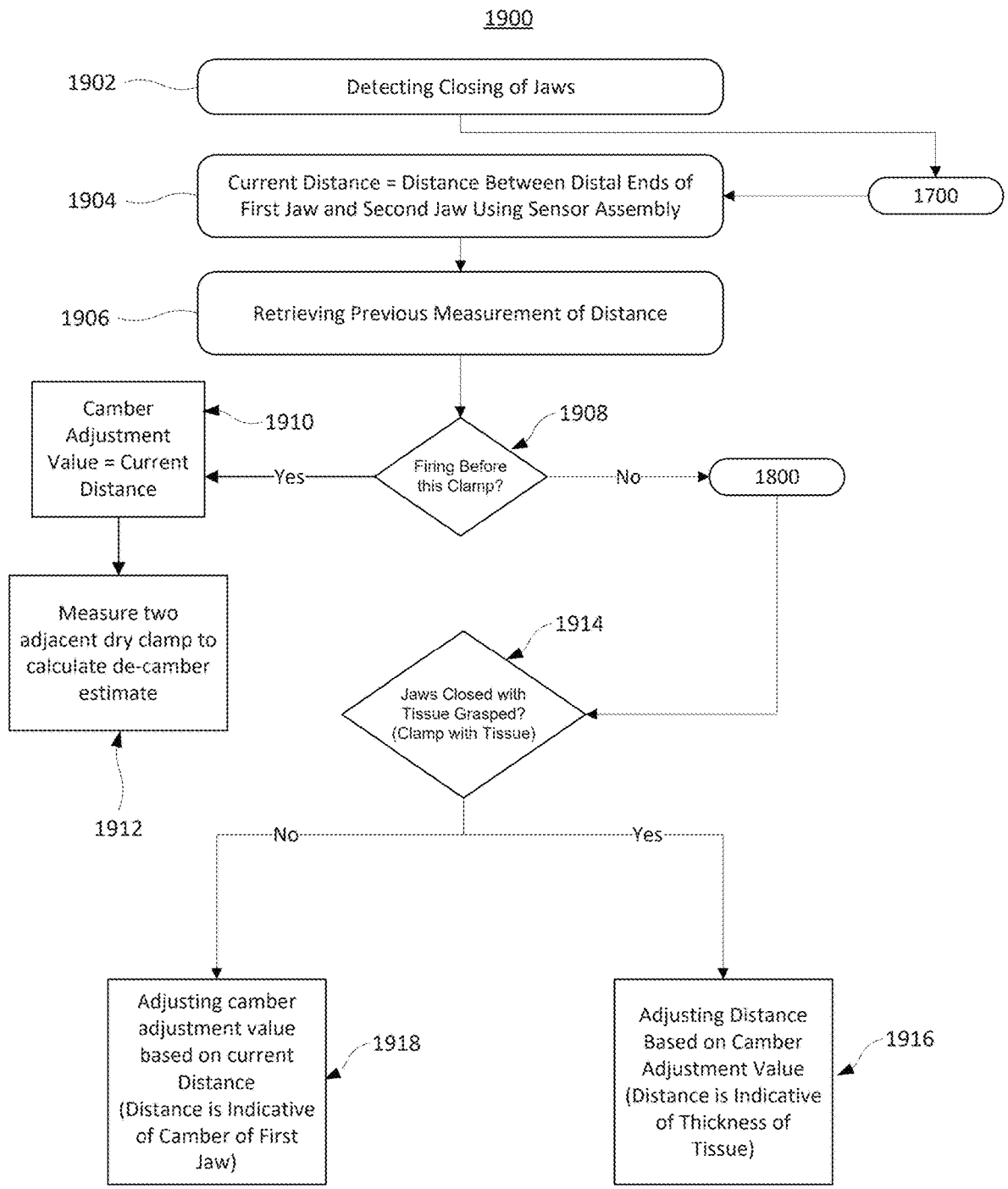
FIG. 19 depicts a flowchart of operating a surgical stapling instrument according to one embodiment.
Figure 20:
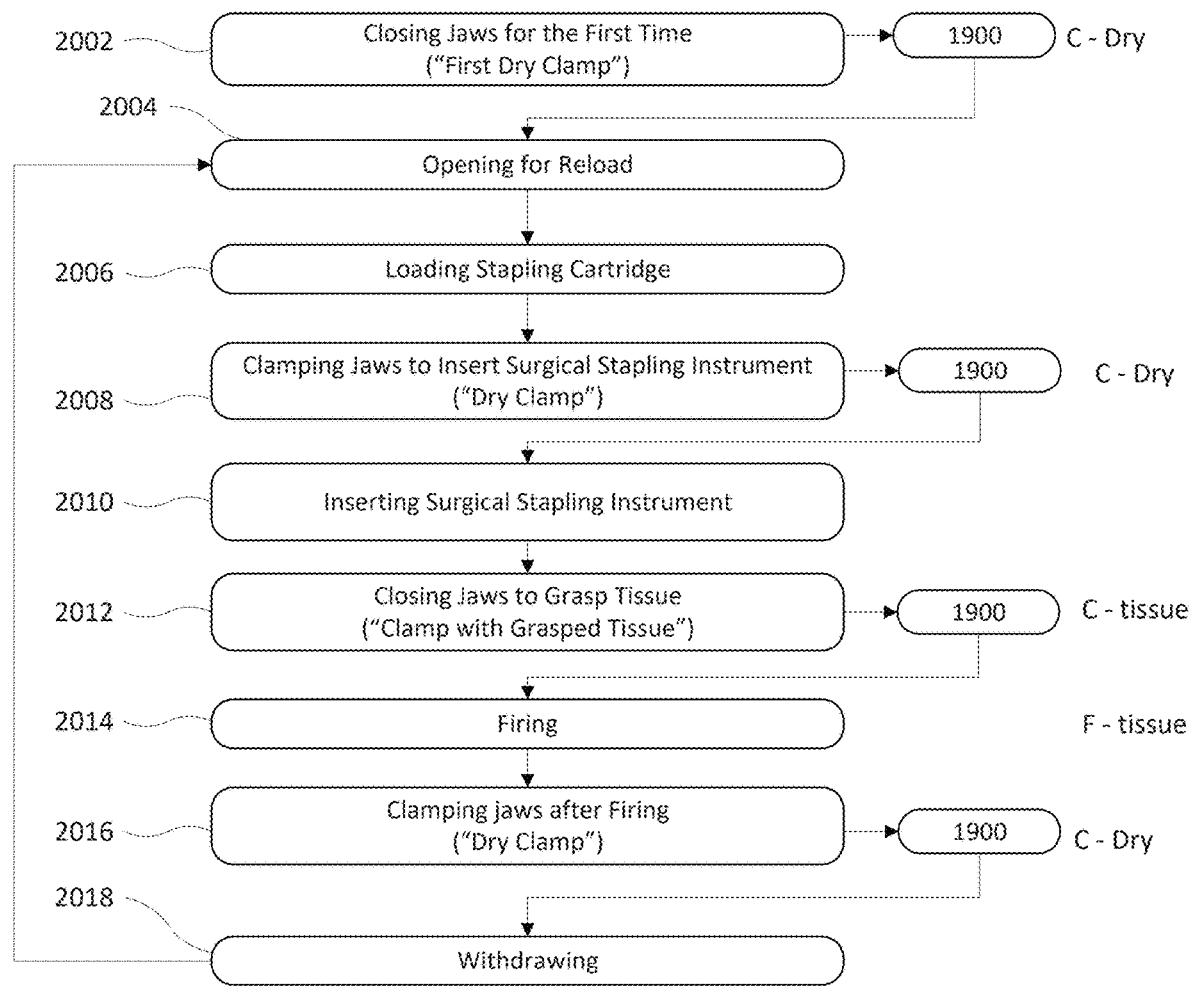
FIG. 20 depicts a flowchart of operating a surgical stapling instrument according to one embodiment.

FIG. 19 depicts a flowchart 1900 of the operation of the controller 182 shown in FIG. 16 in response to the operation 2000, which is shown in FIG. 20 and further explained below. Operation 2000 describes the operation of the surgical stapling instrument 10 after manufacturing, according to various embodiments.

Operation 1900 is performed in response to the detecting, by the controller 182, that the jaws 18, 16 have been actuated from the closed position to the open position and back to the closed position during operation 2000. The operation 1900 may further include performing operation 1700 to derive a current measurement of the distance 103, 104 of the first and second jaws 18, 16.

The operation 1900 may further include: storing, by the controller 182, the measurement of the current measurement of the distance 103 in the non-transitory memory 184 (Block 1904) and retrieving, by the controller 182, a previous measurement of the distance 103 from the non-transitory memory 184 (1906).

The operation 1900 may further include: determining, by the controller 182, whether the surgical stapling instrument 10 was fired immediately preceding the jaws 18, 16 being in the closed position (Block 1908).

The operation 1900 may further include: upon the controller 182 determining that the surgical stapling instrument 10 was fired immediately preceding the jaws 18, 16 being in the closed position, adjusting, by the controller 182, in the non-transitory memory, a camber adjustment value based on the current measurement of the distance 103 (Block 1910); retrieving, by the controller 182, from the non-transitory memory, a previous measurement of the distance 103, when the first and second jaws 18, 16 were closed with no tissue 90 grasped, adjacent to the current measurement of the distance 103 (Previous Adjacent Dry Clamp); deriving, by the controller 182, a de-camber estimate from a change or a difference between the current measurement of the distance 103 and the previous measurement of the distance 103, when the first and second jaws 18, 16 were closed with no tissue 90 grasped (de-camber estimate=Current Measurement of First Parameter "Dry Clamp"−Previous Measurement of First Parameter Adjacent "Dry Clamp"); and storing, by the controller 182, in the memory 184, the de-camber estimate, the current measurement of the first parameter, and characteristics of the firing (1912). In various embodiments, the operation 1900 may further include, providing, by the controller 182, an indication of the de-camber estimate and characteristics of the firing to the user of the surgical stapling instrument 10.

Upon the controller 182 determining that the surgical stapling instrument 10 was not fired immediately preceding the jaws 18, 16 being in the closed position, the operation 1900 may further include performing operation 1900 to determine whether the first and second jaws 18, 16 are in the closed position with tissue 90 grasped therein.

The operation 1900 may further include: upon the controller 182 determining that the surgical stapling instrument 10 was not fired immediately preceding the jaws 18, 16 being in the closed position, determining whether the first and second jaws 18, 16 are in the closed position with tissue 90 grasped therein (Is Current Clamp Status="Clamp on Tissue?") (Block 1914 and operation 1800 shown in FIG. 18).

The operation 1900 may further include: upon determining that the first and second jaws 18, 16 are in the closed position with tissue 90 grasped therein (FIG. 18, operation 1800), adjusting, by the controller, the current measurement of the distance 103 based on the previous measurement of the distance 103 when the first and second jaws 18, 16 were in the closed position with no tissue grasped, wherein the distance 103 is indicative of an amount of tissue 90 grasped therein (Block 1916).

The operation 1900 may further include: upon determining that the first and second jaws 18, 16 are in the closed position with no tissue 90 grasped therein (FIG. 18, operation 1800), adjusting, by the controller 182, the camber adjustment value based on the current measurement of the distance 103, wherein the distance 103 is indicative of the camber of the first jaw 18 (Block 1918).

FIG. 20 depicts a flowchart of the operation 2000 of the surgical stapling instrument 10 shown in FIG. 15 according to various embodiments.

In one embodiment, after a new surgical stapling instrument 10 is manufactured, the operation of the surgical stapling instrument 10 and the end effector 12 may include: actuating, by a user, the end effector 12 to close or clamp the jaws 18, 16 for the first time with no tissue grasped therein ("First Dry Clamp") (Block 2002). In response to the closing of the jaws 18, 16, operation 1900 is performed. During operation 1900, the controller 182 derives the current measurement of the distance 103 (Block 1904), retrieves the previous measurement of distance (Block 1906), determines that this is the first closing of the jaws 18, 16, and stores the current measurement of distance 103 as the previous measurement of distance 103, as the camber adjustment value, and as the baseline adjustment value in the non-transitory memory. In some embodiments, the controller 182 may determine a first closing by determining that the previous measurement of the distance 103 was not previously stored. The controller 182 determines that the surgical stapling instrument 10 was not fired immediately preceding the closing of the jaws 18, 16 (Block 1908), and performs operation 1800. During operation 1800, the controller 182 determines that the current and previous measurement of the distance 103 are the same (Block 1804), and that the jaws 18, 16 are closed with no tissue 90 grasped (Blocks 1808 and 1914). The controller 182 adjusts the camber adjustment value with the current measurement of the distance 103 (Block 1918). The new surgical stapling instrument 10 is then packaged for future use.

In Block 2004, the user opens the package of the new surgical stapling instrument 10 to be used for the first time. The user opens the jaws 18, 16 to load the staples. In Block 2006, the user inserts a staple cartridge 37. The staple cartridge 37 may be selected based on a previous criteria.

In Block 2008, the end effector 12 may be actuated to close or clamp the jaws 18,16 (Current Status="Dry Clamp", Previous Status="Dry Clamp") in order to place the surgical stapling instrument 10 into a patient.

In response to the closing of the jaws 18, 16, operation 1900 is again performed. During operation 1900, the controller 182 derives the current measurement of the distance 103 (Block 1904) and retrieves the previous measurement of distance (Block 1906). The controller 182 determines that the surgical stapling instrument 10 was not fired immediately preceding the closing of the jaws 18, 16 (Block 1908), and performs operation 1800. During operation 1800, the controller 182 determines that the current and previous measurement of the distance 103 are about the same (Blocks 1802 and 1804), and that the jaws 18, 16 are closed with no tissue 90 grasped therein (Blocks 1808 and 1914). The controller 182 adjusts the camber adjustment value with the current measurement of the distance 103 (Block 1918).

In Block 2010, the user inserts the surgical stapling instrument 10 into the patient. The jaws 18, 16 are opened and positioned around the tissue 90 to be fired upon. In Block 2012, the jaws 18,16 are closed with grasped tissue therein (Current Status="Clamp on Tissue", Previous Status="Dry Clamp").

In response to the closing of the jaws 18, 16, operation 1900 is again performed. During operation 1900, the controller 182 derives the current measurement of the distance 103 (Block 1904) and retrieves the previous measurement of distance (Block 1906). The controller 182 determines that the surgical stapling instrument 10 was not fired immediately preceding the closing of the jaws 18, 16 (Block 1908) and performs operation 1800. During operation 1800, the controller 182 determines that the previous and the current measurement of the distance 103 differ by more than the measurement of variation threshold (Block 1802), that the current measurement of the distance 103 is bigger than the previous measurement of distance 103 (Block 1810), and that the jaws 18, 16 are closed with tissue 90 grasped therein (Blocks 1812 and 1914). The controller 182 adjusts the current measurement of the distance 103 with the camber adjustment value (Block 1916).

Regarding Block 2014, as shown in FIGS. 3-6, the end effector 12 may further include a knife/cutting edge 48 configured to be displaced from a proximal end to a distal end of the first and second jaws 18, 16 such that at least a portion of the cutting edge 48 is configured to perform a plurality of firings.

The cutting edge 48 bar runs down tracks/slots in both the jaws 18,16. As the cutting edge 48 gets close to the distal end of the jaws 18, 16, the cutting edge 48, may "pull" the jaws 18,16 together as much as it can depending on the tissue 90.

In some embodiments, the user may wait for the thickness of the grasped tissue (camber compensated measurement) to stabilize for a certain amount of time, e.g., 15 seconds as fluid flows out of the tissue in response to being compressed by the jaws 18, 16. In some embodiments, the amount of time to wait may be fixed. In some embodiments, the amount of time to wait may be dynamic, e.g., until thickness stabilizes. Based on the stabilized tissue thickness, the speed/force of the cutting edge 48 may be adjusted. In other words, in one implementation, the disclosed embodiments may only control speed/force of the cutting edge 48. In another implementation the disclosed embodiments may control or direct when to fire.

In other words, the measurement of thickness may be used to determine how long to wait for the tissue 90 to stabilize before firing, i.e., how long to wait until most of the fluid has been squeezed out. In some embodiments, the controller 182 may be configured to pause the firing after the user pulls out the firing trigger 28, or by displaying an indication that informs the user to wait before pulling the firing trigger 28.

During the firing, the thickness of the tissue may continue to be measured and used to control the speed/force of the cutting edge 48 as the cutting edge 48 travels.

As the cutting edge 48 travels, the firing bar/beam 14 will pull the jaws 18, 16 together and may exert more force on the grasped tissue 90. The more the first jaw 18 is de-cambered, the more force the motor may need to apply to drive the cutting edge 48 forward as it will be harder for the firing beam 14 to pull the jaws 18, 16 together.

In particular, in Block 2014, the controller 182 adjusts the firing, e.g., the speed and force of the cutting edge 48, based on the current measurement of the distance 103 which is indicative of the amount of tissue 90 grasped therein (thickness). The controller 182 may further adjust the firing based on the de-camber value. After the adjustments are made, the cutting edge 48 transects the tissue 90.

In Block 2016, the jaws 18,16 are closed after firing (Previous Status="Firing", Current Status="Dry Clamp").

In response to the closing of the jaws 18, 16, operation 1900 is again performed. During operation 1900, the controller 182 derives the current measurement of the distance 103 (Block 1904) and retrieves the previous measurement of distance (Block 1906). The controller 182 determines that the surgical stapling instrument 10 was fired immediately preceding the closing of the jaws 18, 16 (Block 1908). The controller 182 adjusts the camber adjustment value stored in the non-transitory memory 184, based on the current measurement of the distance 103. In particular, the distance 103 is indicative of the camber of the first jaw 18 (Block 1910). The controller 182 retrieves, from the non-transitory memory, a previous measurement of the distance 103, when the first and second jaws 18, 16 were closed with no tissue 90 grasped, adjacent to the current measurement of the distance 103; derives the de-camber estimate from a change between the current measurement of the distance 103 and the adjacent previous measurement of the distance 103 during closing of the first and second jaws 18, 16 with no tissue grasped ("Two Adjacent Dry Clamps"); and stores, in the memory 184, the de-camber estimate, the current measurement of the distance 103, and characteristics of the firing (Block 1912).

In some embodiments, if the camber adjustment value is lower than a threshold, the controller 182 may provide an indication to the user so that during the next firing, the speed at which the transection is performed is adjusted or the tissue 90 is clamped for a longer time period.

In Block 2018, the jaws 18,16 are withdrawn from the patient.

In various embodiments, if multiple firings are required, Blocks 2004 and 2006 are repeated.

In Block 2008, the end effector 12 may be actuated to close or clamp the jaws 18,16 after loading the stapling cartridge 37 (Current Status="Dry Clamp", Previous Status="Dry Clamp").

In response to the closing of the jaws 18, 16, operation 1900 is again performed. During operation 1900, the controller 182 derives the current measurement of the distance 103 (Block 1904) and retrieves the previous measurement of the distance 103 (Block 1906). The controller 182 determines that the surgical stapling instrument 10 was not fired immediately preceding the closing of the jaws 18, 16 (Block 1908), and performs operation 1800. During operation 1800, the controller 182 determines that the current and previous measurement of the distance 103 are about the same (Blocks 1802 and 1804) and that the jaws 18, 16 are closed with no tissue 90 grasped therein (Blocks 1808, and 1914), and adjusts the camber adjustment value with the current measurement of the distance 103 (1918).

Blocks 2010-2018 are performed again. If another firing is needed, Blocks 2004-2018 are repeated.

In some embodiments, the closing of jaws 18, 16 with grasped tissue (Block 2012) may be repeated several times to perform several measurements of the amount of grasped tissue 90. In this embodiment, the jaws 18, 16 are opened and positioned around the tissue 90 and the jaws 18,16 are closed (Current Status="Clamp on Tissue", Previous Status="Clamp on Tissue") (Block 1806).

In response to the closing of the jaws 18, 16, operation 1900 is again performed. During operation 1900, the controller 182 derives the current measurement of the distance 103 (Block 1904) and retrieves the previous measurement of distance (Block 1906). The controller 182 determines that the surgical stapling instrument 10 was not fired immediately preceding the closing of the jaws 18, 16 (Block 1908) and performs operation 1800. During operation 1800, the controller 182 determines that the previous and the current measurement are about the same (1802), that the current measurement of the distance 103 minus the "Max Empty Gap Device ID" is greater than or equal to a measurement variation threshold (Block 1804), and that the jaws 18, 16 are closed with tissue 90 grasped therein (Blocks 1808 and 1914). The controller 182 adjusts the current measurement of the distance 103 with the camber adjustment value (Block 1916).

Figure 21:
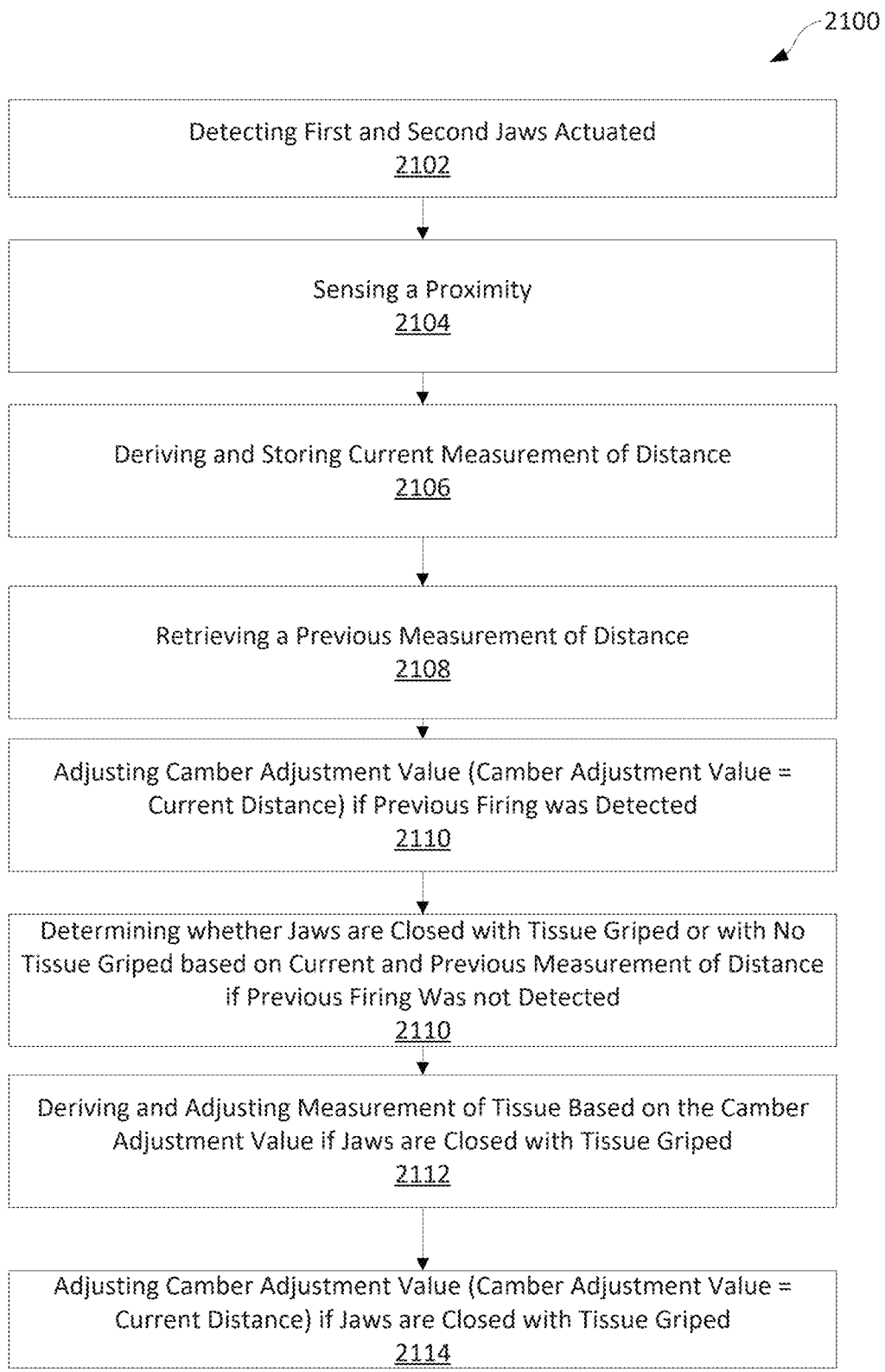
FIG. 21 depicts a flowchart of operating a surgical stapling instrument according to one embodiment.

FIG. 21 depicts a flowchart of the operation 2100 of the surgical stapling instrument 10 shown in FIG. 15 according to one embodiment.

In one embodiment, the operation 2100 may include: detecting, by the controller, that the first and second jaws have been actuated from the closed position to the open position and back to the closed position (Block 2102); sensing, subsequent to the actuation, by a sensor assembly disposed at a distal end of the end effector, a proximity of a distal end of the first jaw and a distal end of the second jaw, in response to the first and second jaws being actuated, generating a first signal indicative thereof, and communicating the first signal to the controller, wherein the sensor assembly is in signal communication with the controller (Block 2104); deriving, by the controller, a current measurement of a distance between the distal end of the first jaw and the distal end of the second jaw based on the first signal and storing, by the controller, in a non-transitory memory coupled with the controller, the current measurement of the distance (Block 2106); retrieving, by the controller, from the non-transitory memory, data indicative of a previous measurement of the distance (Block 2108); determining, by the controller, whether the surgical stapling instrument was fired immediately preceding the actuation, and based thereon, the method further comprising one of: determining that the surgical stapling instrument was fired immediately preceding the actuation, the method further comprising: adjusting, by the controller, a camber adjustment value stored in the non-transitory memory, based on the current measurement of the distance, wherein the distance is indicative of the camber of the first jaw; retrieving, by the controller, from the non-transitory memory, a previous measurement of the distance, when the first and second jaws were closed with no tissue grasped, adjacent to the current measurement of the distance; deriving, by the controller, a de-camber estimate from a difference between the current measurement of the distance and the previous measurement of the distance, when the first and second jaws were closed with no tissue grasped, adjacent to the current measurement of the distance; and storing, by the controller, in the non-transitory memory, the de-camber estimate and the current measurement of the distance (Block 2110); or determining that the surgical stapling instrument was not fired immediately preceding the actuation, the method further comprising: determining, by the controller, whether the first and second jaws are in the closed position with tissue grasped therebetween, the method comprising one of: upon determining that the first and second jaws are in the closed position with tissue grasped therein, the method further comprising: deriving, by the controller, a measurement of thickness of the tissue based on the distance; and adjusting, by the controller, the current measurement of the thickness of the tissue, wherein the distance is indicative of an amount of tissue grasped therein (Block 2112); or upon determining that the first and second jaws are in the closed position with no tissue grasped therein, adjusting, by the controller, the camber adjustment value based on the current measurement of the distance, wherein the distance is indicative of the camber of the first jaw (Block 2114).

In summary, when the device is built, the first clamp and tissue gap measurement or distance 103 is a clamp dry and the tissue gap measurement may be used to determine the anvil cambering estimate for the device. Every time when the device is clamped, the tissue gap may be measured. For any two adjacent clamps without a firing in between the two clamps, the two tissue gap measurements may be used for tissue thickness estimate. The combination of the two adjacent clamps are: Current_clamp is clamp dry, previous_clamp is clamp dry; Current_clamp is clamp on tissue, previous_clamp is clamp dry (the delta is the tissue thickness); Current_clamp is clamp on tissue, previous_clamp is clamp on tissue; and Current_clamp is clamp dry, previous_clamp is clamp on tissue.

If there is a firing between the two clamps, the clamp dry tissue gap before the firing (from the stored data of the device) is also retrieved. The next first clamp dry tissue gap is compared to the clamp dry tissue gap before the firing, the delta between these two is the anvil de-cambering from this firing. The anvil clamp dry tissue gap for the device is updated, and the de-camber amount is added to the anvil overall camber. The de-camber amount is also used for the tissue thickness calibration. In other words, the disclosed embodiments estimate the tissue thickness at clamp, and the device may have a de-cambering amount from firing as calibration to the tissue thickness estimate) and gives the devices a self learning input. The overall anvil cambering amount may be used for the next clamp on tissue decision. The current decision is based on the estimated tissue thickness and reload selection, however, the anvil cambering status is also important in the decision. The overall cambering information may also be used for the next firing control. The overall cambering information can also be used to determine the life cycle of the device (more important than the number of firings).

Figure 22:
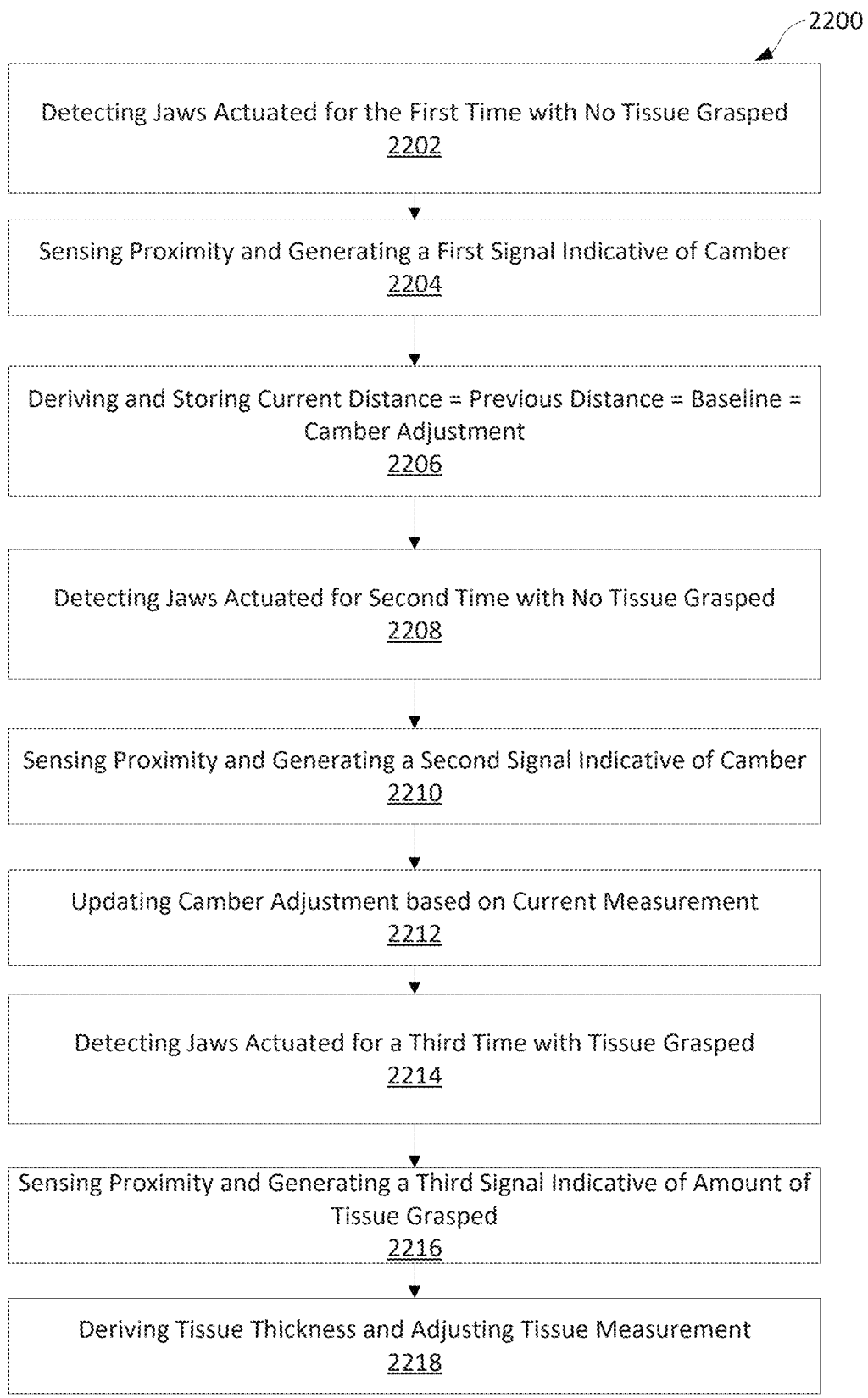
FIG. 22 depicts a flowchart of operating a surgical stapling instrument according to one embodiment.

FIG. 22 depicts a flowchart of the operation 2200 of the surgical stapling instrument 10 shown in FIG. 15 according to one embodiment. The operation 2200 may include: detecting, by the controller, that the first and second jaws have been actuated from the closed position to the open position and back to the closed position for a first time (2202); sensing, by a sensor assembly disposed at a distal end of the end effector and in signal communication with the controller, a proximity of a distal end of the first jaw to a distal end of the second jaw, in response to the first and second jaws having been actuated for the first time, generating a first signal indicative thereof, and communicating the first signal to the controller, wherein the first signal includes data indicative of a camber of the first jaw; deriving, by the controller, from the first signal, a current measurement of a distance between the distal end of the first jaw and the distal end of the second jaw; detecting, by the controller, data indicative that a previous measurement of the distance has not been previously stored; storing, by the controller in a non-transitory memory coupled with the controller, the current measurement of the distance as the previous measurement of the distance, as a camber adjustment value, and as a baseline camber adjustment value (Block 2206); detecting, by the controller, that the first and second jaws have been actuated from the closed position to the open position and back to the closed position for a second time with no tissue grasped therein (Block 2208); sensing, by the sensor assembly, the proximity, in response to the first and second jaws being actuated for the second time, generating a second signal indicative thereof, and communicating the second signal to the controller, wherein the second signal includes data indicative of an amount of the tissue grasped (Block 2210); deriving, by the controller, based on the second signal, the current measurement of the distance; updating, by the controller, the adjusted camber value with the current measurement of the distance (Block 2212); detecting, by the controller, that the first and second jaws have been actuated from the closed position to the open position and back to the closed position for a third time with tissue grasped therein (Block 2214); sensing, by the sensor assembly, the proximity, in response to the first and second jaws having been actuated for the third time, generating a third signal indicative thereof, and communicating the third signal to the controller, wherein the third signal includes data indicative of an amount of the tissue being grasped (Block 2216); deriving, by the controller, based on the third signal, the current measurement of the distance; deriving, from the current measurement of the distance, a measurement of thickness of the tissue; and adjusting, by the controller, the current measurement of the thickness of the tissue based on the camber adjustment value (Block 2218).

Figure 23:
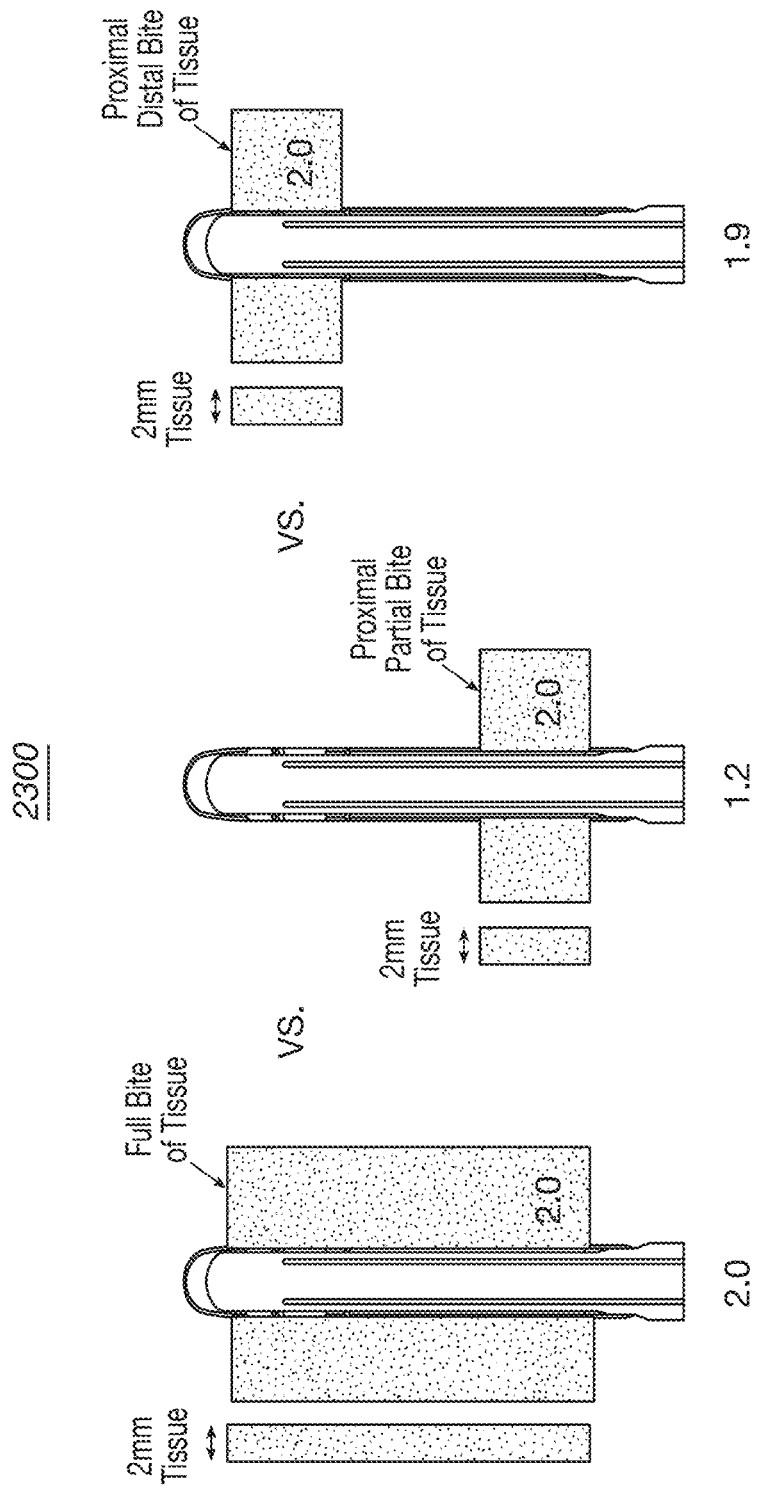
FIG. 23 depicts a diagram of different tissue loading conditions according to one embodiment.

FIG. 23 depicts a diagram 2300 of different tissue loading conditions according to one embodiment.

In some embodiments, there are challenges to sense thickness of the tissue 90. For example, on different biting of the tissue, the loading condition of the tissue 90 may change the measurement of the thickness of the grasped tissue 90 (assuming measurements are taken in one location at the most distal end).

In some embodiments, as described above, the surgical stapling instrument is able to track the tissue gap measurement (distance 103 between the distal ends of the first and second jaws 18, 16) and build compensation for the anvil camber and de-camber.

When the jaws 18, 16 are closed with tissue grasped therein, the distance 103 is measured again so only the delta from a previous dry clamp and a current clamp on tissue may be used for tissue thickness calculation.

With the anvil camber information and continuous measurement of tissue gaps during clamp and waiting period, the disclosed embodiments may construct the anvil-cartridge jaw curves shown below for firing preparation.

In some embodiments, the tissue 90 may be either easily compressed or hard to compress. Therefore, different waiting periods and tissue gap measurements may be used for accurate estimation of the tissue 90 thickness.

The disclosed embodiments further provide logic to determine if the device is "Dry Clamp" or "Clamp on Tissue". Overall anvil camber information (including de-camber) may also be tracked. As shown below, the disclosed embodiments enable plotting of a bridged jaw curve when the jaws 18, 16 are closed with tissue 90 grasped. A decision may be made and shared with the user if the reload selection is appropriate. During firing, the tissue thickness may be further accurately estimated. Information regarding whether the tissue 90 may be easily compressed may be available and updated at every control loop cycle. The updated data including tissue 90 information may be used for the next control loop firing control.

In particular, the disclosed embodiments, as mentioned previously, measure the tissue gap or distance 103 at one location (distal end).

The disclosed embodiments further use continuous measurement of the distance 103 to estimate the tissue thickness accurately and further adjusts for tissue thickness correction and for firing. The disclosed embodiments enable plotting a jaw curve (using different software) to enable accurate tissue thickness estimation. The disclosed embodiments may also estimate if the tissue is easily compressed or not. In every loop cycle, the tissue gap change may be calculated together with the knife E-beam location and the movement amount to accurately estimate the tissue thickness. In particular, the tissue thickness under jaw compression thickness is the information needed for ultimate control and reload selection.

The disclosed embodiments provide sensing with simplified measurement. The disclosed embodiments measure compression force at one location applied to the tissue 90 and use the measurement to estimate the tissue compression pressure along the whole jaw length. The disclosed embodiments use one spot measurement to estimate the tissue thickness. The thickness estimate may be calculated at closure, during waiting, and at any time during the firing and become a more and more accurate estimate of the tissue thickness. The tissue thickness estimation may be used for the device self-learning for implementing control in future occasions. The adjustment process and errors found in early stages enable more accurate estimation at later stages. Later stage estimated outcomes may be used to correct an algorithm used in the early estimation. Gradually, early estimations may become more accurate enabling the surgical stapling instrument to provide the user with more accurate information earlier.

Figure 24:
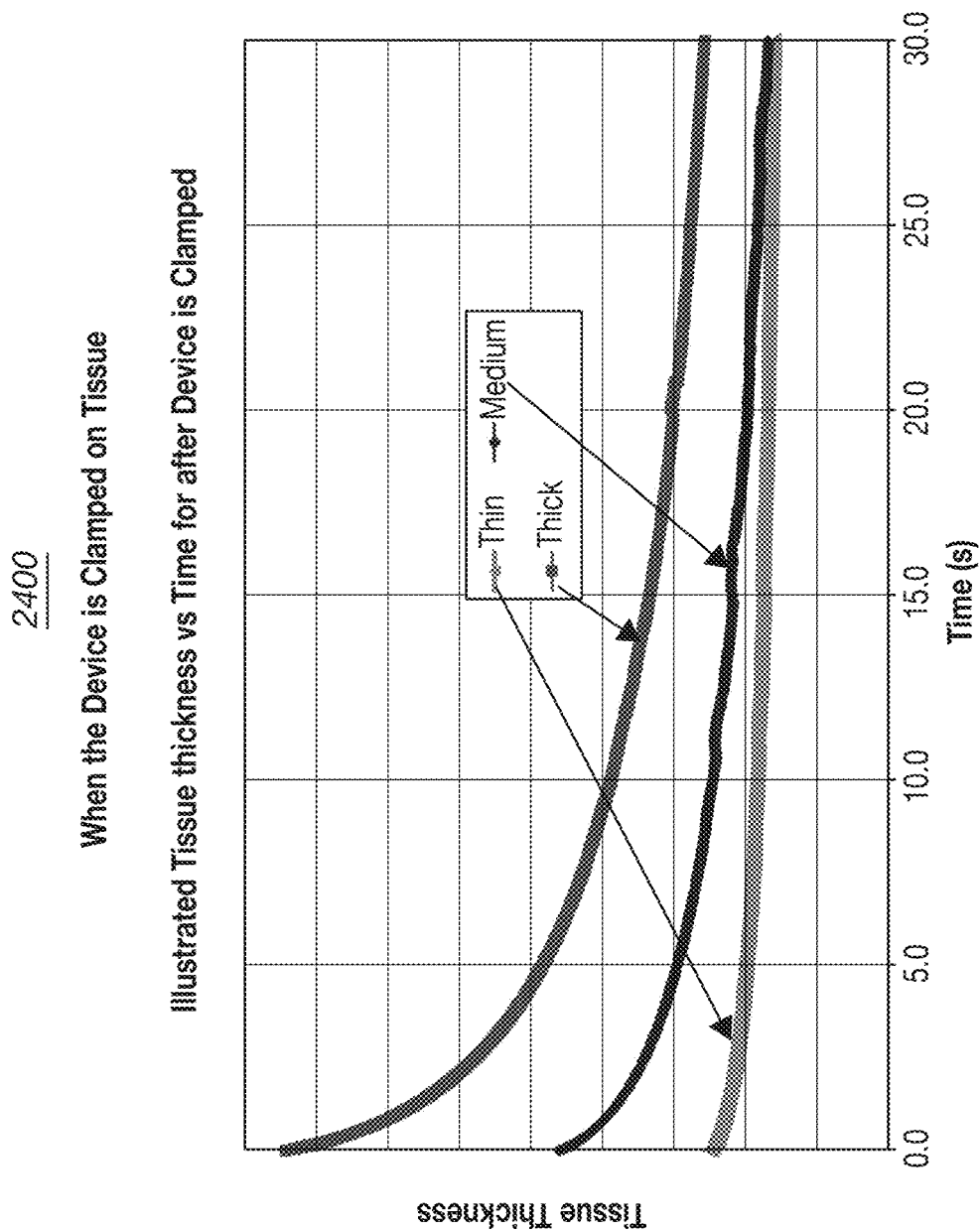
FIG. 24 depicts a graph describing tissue thickness in relation to time according to one embodiment.

FIG. 24 depicts a graph 2400 describing tissue thickness in relation to time when the jaws 18, 16 are closed with tissue grasped therein, at a given location (e.g., distal) according to one embodiment.

Different staple cartridges 37 (or "reloads") have different size staples to account for differing tissue 90 thickness. As soon as the thickness of the grasped tissue 90 is within the range of the tissue 90 thickness that the staple cartridge loaded in the instrument is rated for, the surgical stapling instrument 10 may be ready to fire, since the staples would be sized appropriately. If the surgical stapling instrument 10 has small staples and there is no sufficient wait time for the fluid to escape, the tissue 90 may be too thick and the staples may not form correctly.

Based on the delta and absolute values from 0 seconds to 15 seconds, the tissue 90 thickness may be estimated. For example, the surgical stapling instrument 10 may indicate that a thin tissue 90 is ready at 5 seconds, a medium tissue is ready at 10 seconds, and a thick tissue is ready at 15 seconds.

The disclosed embodiments may generate the distance 103 or tissue gap from the proximal to distal ends of the jaws 18, 16 based on the stiffness of the first jaw 18 and the camber adjustment.

Figure 25:
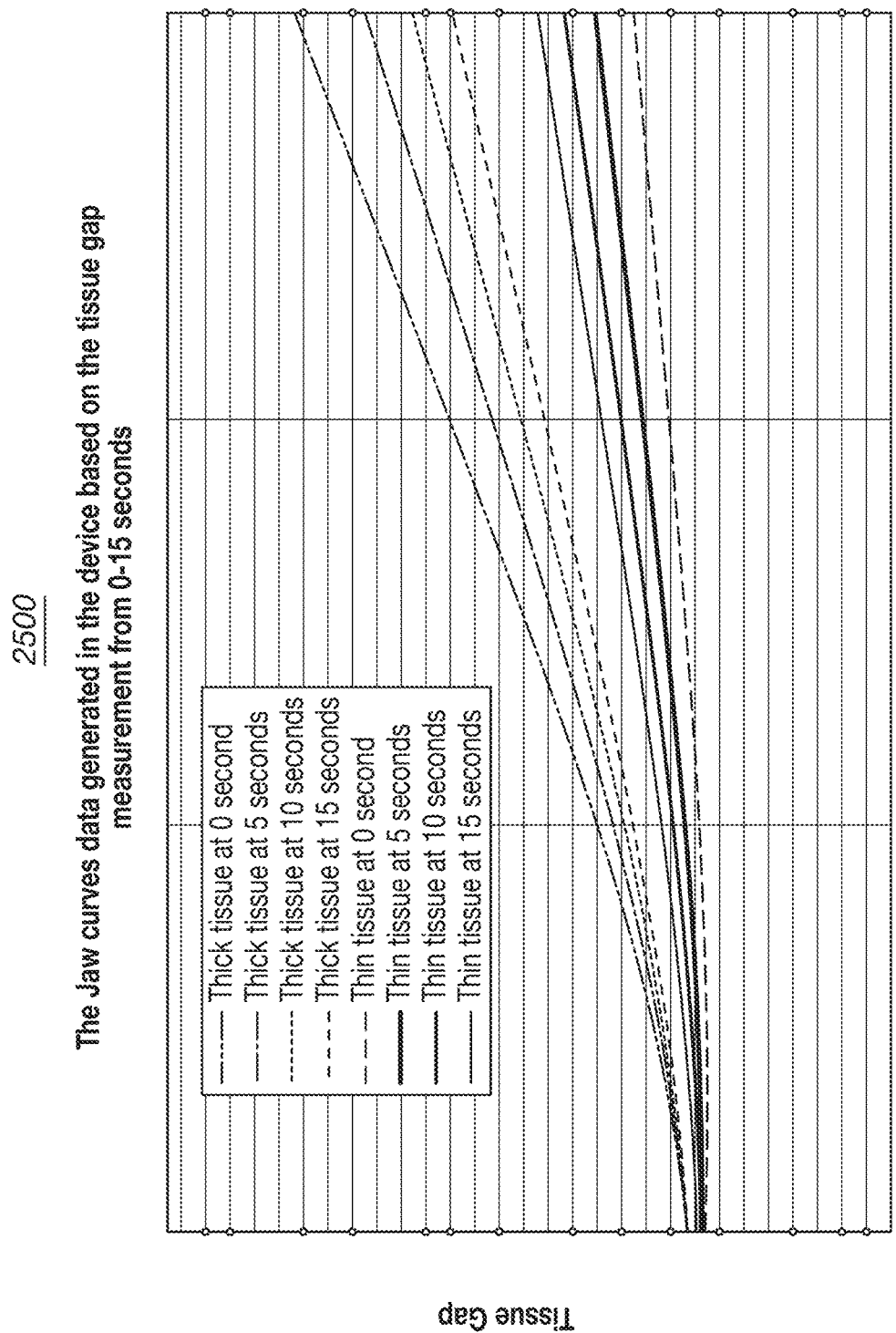
FIG. 25 depicts a graph describing jaw curves in relation to time according to one embodiment.

FIG. 25 depicts a graph 2500 describing jaw curves in relation to time according to one embodiment. In particular, graph 2500 depicts jaw 18, 16 curves data generated in the surgical stapling instrument 10 based on the distance 103 measured from 0-15 seconds.

The distance 103 or tissue gap from the proximal end to the distal end of the jaws 18, 16 may be generated based on the tissue gap measurement from graph 2400 based on pre-calibrated jaw stiffness and camber status adjustment.

Figure 26:
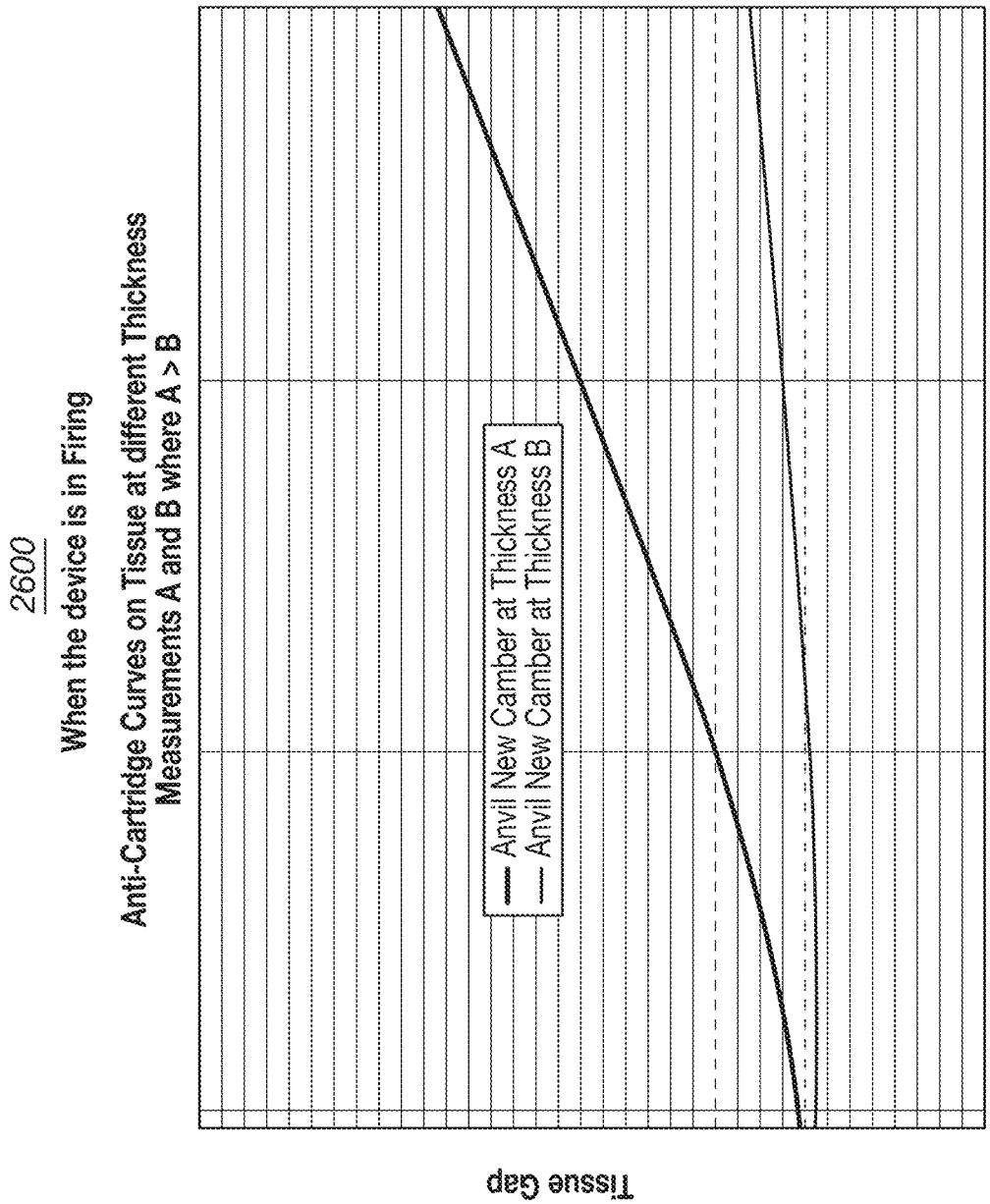
FIG. 26 depicts a graph describing anvil-cartridge curves according to one embodiment.

FIG. 26 depicts a graph 2600 describing anvil-cartridge curves when the surgical stapling instrument 10 is firing according to one embodiment.

When the cutting edge 48 or E-beam moves a delta distance in one control loop cycle, the tissue gap change/change in distance 103 (Current Gap–Previous Gap) at the most distal may be calculated based on the jaw curve. The tissue gap change at the distal end may also measured during the one control loop cycle: If the Tissue_Gap_Delta_Measured is bigger than Tissue_Gap_Delta_Calculated_From_Jaw_Curve: the tissue 90 is easier to be compressed than a standard tissue 90 (which is used to construct the jaw curve). Based on how much easier it is to be compressed, the tissue adjustment is applied to the control in the next firing loop.

Figure 27:
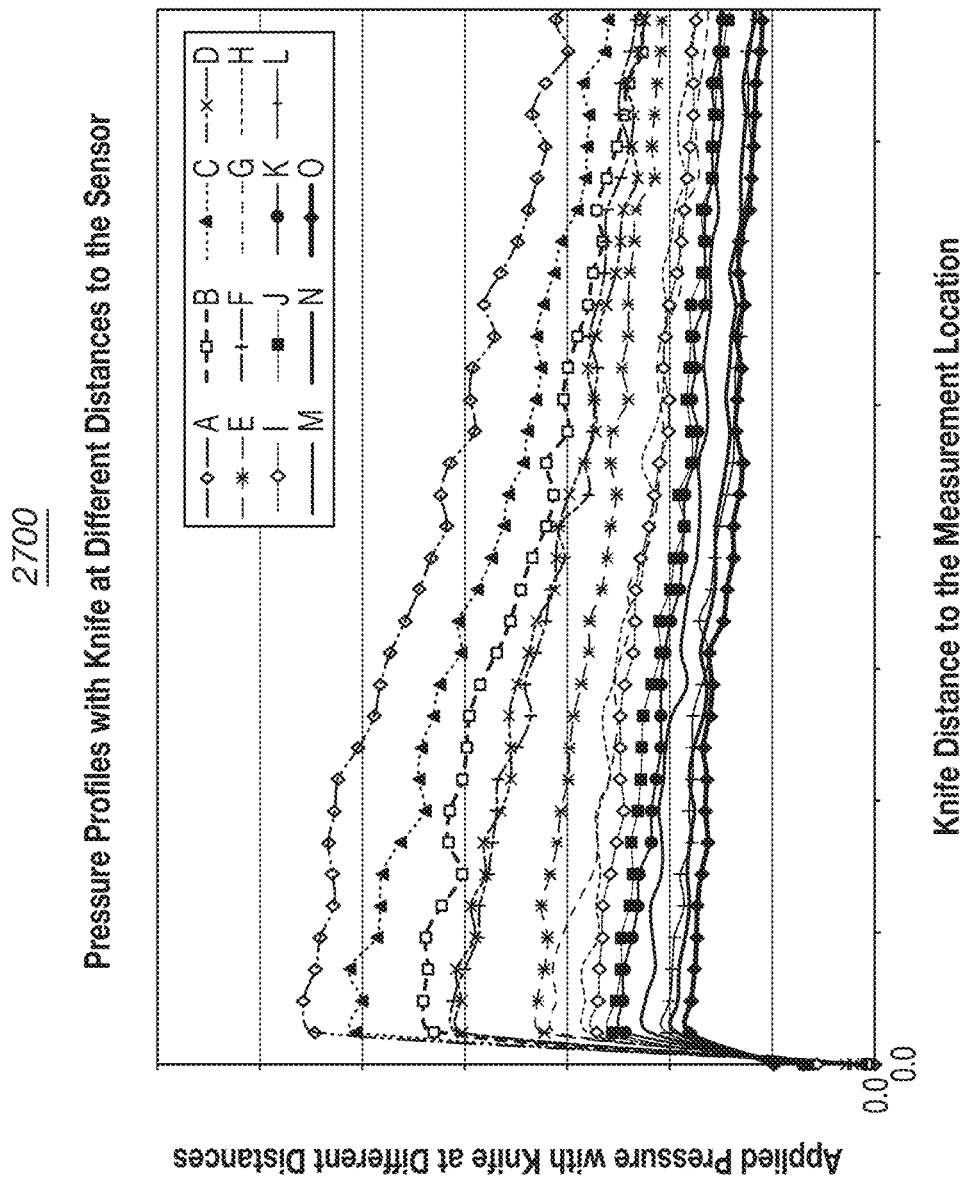
FIG. 27 depicts a graph describing pressure profiles at different locations according to one embodiment.

FIG. 27 depicts a graph 2700 describing pressure profiles at different locations from the sensor assembly 102 according to one embodiment.

The graph 2700 represents the tissue pressure (sum of pressure along the lateral direction) along longitudinal direction with the cutting edge 48/knife at different distances to the measured location (can be assumed at any position after 0.0 mm, e.g., 5.0 mm). The overall tissue pressure along the jaw can be plotted if the pressure (force) at the green spot (e.g., 5.0 mm) is measured. For example, a point from the red curve can plot the whole red line (since lines are not crossed).

Figure 28:
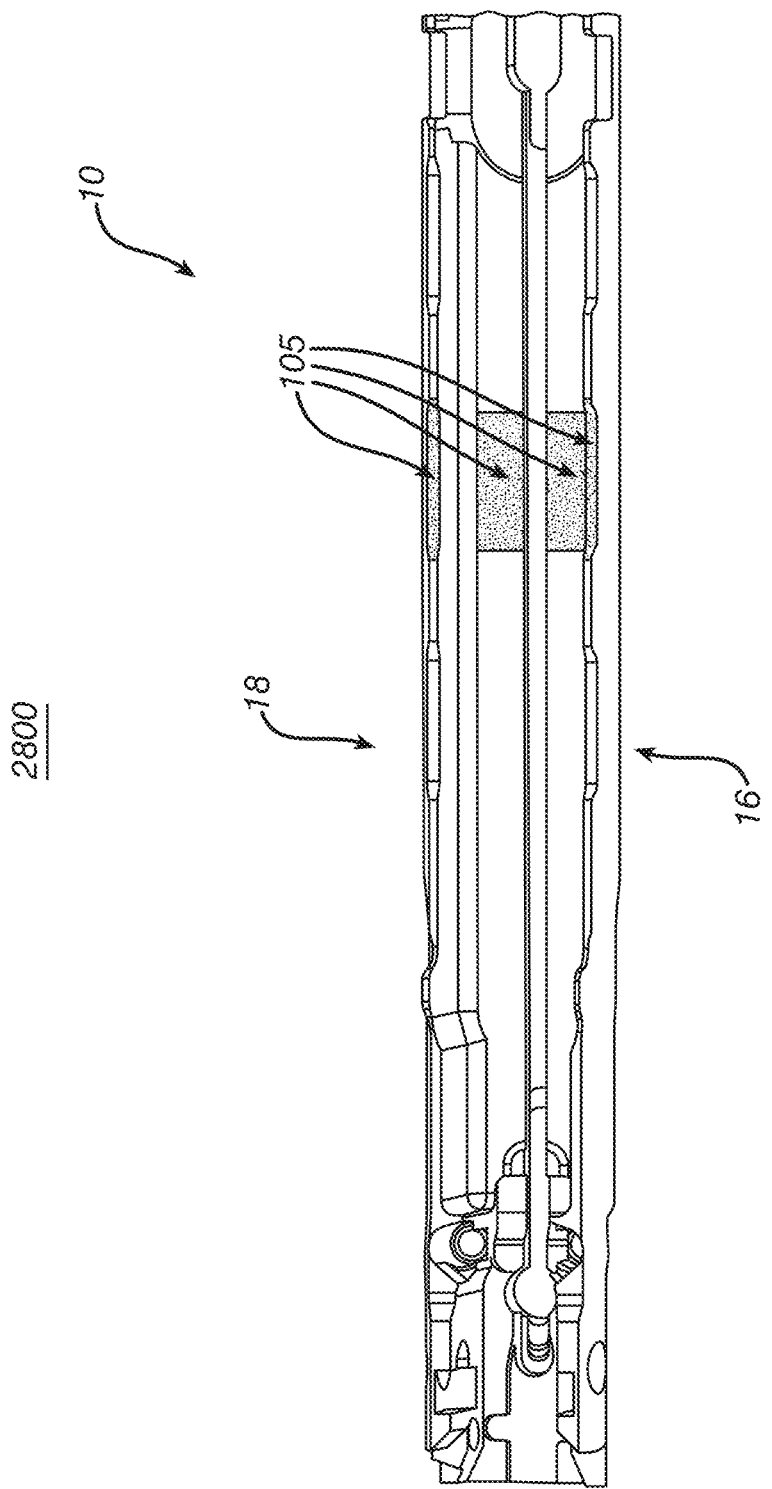
FIG. 28 depicts a top view of a lower jaw according to one embodiment.

FIG. 28 depicts a top view 2800 of a lower jaw 16 according to one embodiment. It is challenging to measure the tissue 90 compression force along the whole length of the jaw 16. The disclosed embodiments estimate the tissue compression force or the tissue compression pressure along the whole length. The disclosed embodiments measure the tissue compression pressure (force) at just one location (across the channel) and use one spot measurement together with the location of the knife to estimate the tissue compression pressure (force) along the lower jaw 16 length.

Measuring tissue compression force at all locations in the jaws 18, 16 is challenging and expensive. Further, wiring of sensors in the jaws 18,16 is not easy or possible in some occasions. The disclosed embodiments perform measurements at one channel location and use the measurements to estimate the tissue pressure along the jaws 18,16 and use the measurement to estimate the tissue thickness.

In some embodiments, the disclosed embodiments measure the tissue 90 compression forces at 4 possible force locations across the channel (e.g., left rail, bottom of channel left, bottom of channel right, and right rail). The disclosed embodiments combined the forces measured with knife E-beam location (the distance of the knife 48).

E-beam to the measurement location anvil-channel E-beam entrance engagement location to the measurement location). As shown FIG. 29, the tissue linear compression pressure along the jaw may be estimated and plotted. Based on the above information, the tissue thickness may be accurately estimated.

In particular, in some embodiments, the end effector further comprises a cutting edge 48 configured to be displaced from a proximal end to a distal end of the first and second jaws 18, 16 such that at least a portion of the cutting edge 48 is configured to transect the grasped tissue 90 over a number of firings.

The controller 182 is further configured to detect that the surgical stapling instrument 10 is about to fire; retrieve, from the non-transitory memory 184, the de-camber estimate; determine that the de-camber estimate is less than a minimum de-camber threshold; and adjust a mode of operation of the firing based on the de-camber estimate including a force and speed of the cutting edge 48.

In some embodiments, as shown in FIG. 28, the sensor assembly 102 may comprise force sensors 105 disposed at four locations along a channel of the lower jaw 16 to sense a compression force indicative of thickness of the grasped tissue 90, the force of the cutting edge 48 when the grasped tissue 90 is transected, and to track the location of the cutting edge 48.

In some embodiments, the controller 182 is configured to: upon determining that the surgical stapling instrument 10 was fired immediately preceding the closing of the first and second jaws 18, 16, provide an indication of the de-camber estimate and characteristics of the firing to a user of the surgical stapling instrument 10, wherein the characteristics of the firing includes number of firings, and measurements of force and speed of the cutting edge 48 at each corresponding location of the cutting edge 48.

In some embodiments, the force sensors 105 may be used to estimate the tissue thickness and force of the cutting edge.

The force sensors 105 may be disposed at four different locations of the channel (across the lateral direction). The force sensors 105 sense the force at both rails and bottom floor in the channel at one section or location instead of the whole length. The force sensors 105 may be used to estimate the tissue 90 thickness and force to fire together with cutting edge 48 location. The closure force measured from four locations may be used for tissue thickness estimation. The force measured when the cutting edge 48 is at a different location may be used to predict the force at the knife location thus accurately predict the force at the cutting edge 48 location during firing even if the force is only measured at one section.

Figure 29:
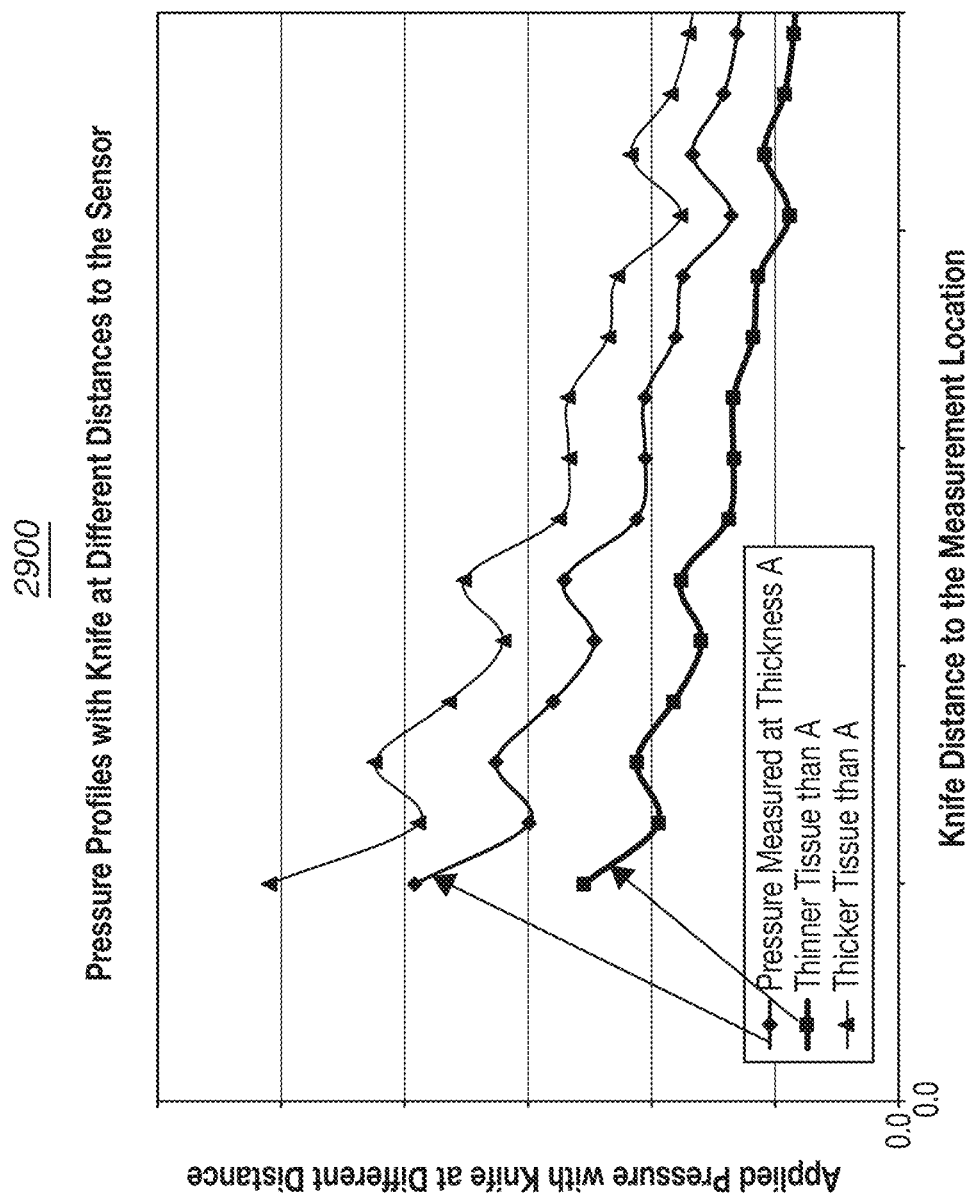
FIG. 29 depicts a graph describing pressure profiles at different locations from the sensor assembly 102 according to one embodiment.

FIG. 29 depicts a graph 2900 describing pressure profiles at different locations from the sensor assembly 102 according to one embodiment.

Graph 2900 shows the tissue compression force (pressure) at 5.0 mm when the knife is located at different distances to the location of the sensor assembly 102 to be used to calibrate tissue thickness.

Referring to FIG. 30, there is shown a block diagram of system 1002 for operating a surgical stapling instrument 10 according to some embodiments.

Based on the measured force (pressure at one location, combined with knife position) the tissue thickness may be estimated. In some embodiments, the measurement of thickness may be used by the controller 182 to determine how fast to advance the knife/cutting edge 48 and how much torque to apply to push the cutting edge 48 forward.

In some embodiments, the measurement of thickness may be continually measured by the controller 182 during the firing to adjust or vary the speed/force of the knife/cutting edge 48 as the cutting edge 48 advances to deal with tissue that may have different thickness variations.

In some embodiments, as shown in FIGS. 12-16 and 30, the surgical stapling instrument includes an end effector 12 configured to grasp tissue 90. The end effector 12 may include a first jaw 18 pivotably coupled at a proximal end thereof with a second jaw 16 so as to be pivotable between an open position and a closed position for grasping tissue therebetween. The end effector 12 may further include the knife 48 configured to be displaced from a proximal end of the end effector 12 to a distal end thereof, so as to transect tissue 90 grasped between the first and second jaws 18, 16, one of the first or second jaws 18, 16 further configured to receive a staple cartridge 37 seatable therein and including a sled 41 and staples 47. The sled 41 may be configured to be displaced by the knife 48 from a proximal end to a distal end of the staple cartridge 37 to deploy the staples 47 into the tissue 90 grasped between the first and second jaws 18, 16, along the transection.

The end effector 12 may further include a sensor 102, i.e., a sensor assembly 102, deployed at the distal end of the end effector 12 and configured to sense a parameter indicative of a distance between the first and second jaws 18, 16 and generate a signal 110 indicative thereof.

The surgical stapling instrument 10 may further include a motor 1004 located external to the end effector 12 and a drive train 1008 operably coupled between the motor 1004 and the knife 48, wherein the motor 1004 is configured to controllably displace the drive train 1008 so as to displace the knife 48, and thereby the sled 41, so as to substantially simultaneously transect the tissue 90 grasped by the end effector 12 and deploy the staples 47 therein along, and on either side of, the transection, and thereafter retract the drive train 1008 so as to retract the knife 48 back to the proximal end of the end effector 12.

The surgical stapling instrument 10 may further include a control circuit 182 coupled with the sensor 102 and the motor 1004 and which controls a rate at which the motor 1004 is attempting to displace the drive train 1008. The control circuit 182 is further configured to: determine, based on the signal 110 when the first and second jaws 18, 16 have been actuated from the closed position to the open position, without the motor 1004 having displaced the drive train 1008, and back to the closed position, the current distance between the first and second jaws 18, 16 and further determine an adjusted current distance based on an adjusted baseline distance determined, based on the signal 110 when the first and second jaws 18, 16 have been actuated from the closed position to the open position, after the motor 1004 has displaced and retracted the knife 48, and back to the closed position, based on the then current distance between first and second jaws 18, 16 and a previously determined adjusted baseline distance.

In some embodiments, the control circuit 182 may be further configured, while the first and second jaws 18, 16 remain in the closed position, to periodically determine the adjusted current distance between the first and second jaws 18, 16 and based on a comparison between at least a subset of the determined adjusted current distances, determine when to initiate displacement of the drive train 1008.

In some embodiments, the control circuit 182 may be further configured to determine, based on the adjusted current distance between the first and second jaws 18, 16, a rate of displacement at which the motor 1004 should attempt to maintain during a next displacement of the drive train 1008.

In some embodiments, the control circuit 182 may be further configured to periodically repeat the determination of the adjusted current distance and rate of displacement as the drive train 1008 is displaced.

V. Examples of Combinations

The following examples/clauses relate to various non-exhaustive ways in which the teachings herein may be combined or applied. It should be understood that the following examples/clauses are not intended to restrict the coverage of any claims that may be presented at any time in this application or in subsequent filings of this application. No disclaimer is intended. The following examples/clauses are being provided for nothing more than merely illustrative purposes. It is contemplated that the various teachings herein may be arranged and applied in numerous other ways. It is also contemplated that some variations may omit certain features referred to in the below examples/clauses. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

The following examples/clauses also relate to various non-exhaustive ways in which the teachings herein may be combined or applied.

Example/Clause Set No. 1

1. A method for operating a surgical stapling instrument, the surgical stapling instrument comprising a controller and an end effector including a first jaw pivotably coupled at a proximal end thereof with a second jaw so as to be pivotable between an open position and a closed position for grasping tissue therebetween, the method comprising:
    detecting, by the controller, that the first and second jaws have been actuated from the closed position to the open position and back to the closed position;
    sensing, subsequent to the actuation, by a sensor assembly disposed at a distal end of the end effector, a proximity of a distal end of the first jaw and a distal end of the second jaw, in response to the first and second jaws being actuated, generating a first signal indicative thereof, and communicating the first signal to the controller, wherein the sensor assembly is in signal communication with the controller;
    deriving, by the controller, a current measurement of a distance between the distal end of the first jaw and the distal end of the second jaw based on the first signal;
    storing, by the controller, in a non-transitory memory coupled with the controller, the current measurement of the distance;
    retrieving, by the controller, from the non-transitory memory, data indicative of a previous measurement of the distance, the method further comprising one of:
        determining, by the controller, that the surgical stapling instrument was fired immediately preceding the actuation, and based thereon, adjusting, by the controller, a camber adjustment value stored in the non-transitory memory based on the current measurement of the distance, wherein the distance is indicative of the camber of the first jaw; or
        determining, by the controller, that the surgical stapling instrument was not fired immediately preceding the actuation, and based thereon, determining, by the controller, whether the first and second jaws are in the closed position with tissue grasped therebetween, the method comprising one of:
            determining that the first and second jaws are in the closed position with tissue grasped therebetween, deriving, by the controller, a measurement of thickness of the tissue based on the distance and adjusting, by the controller, the current measurement of the thickness of the tissue, wherein the distance is indicative of an amount of tissue grasped therein; or
            determining that the first and second jaws are in the closed position with no tissue grasped therebetween and adjusting, by the controller, the camber adjustment value based on the current measurement of the distance, wherein the distance is indicative of the camber of the first jaw.

2. The method of claim 1, further comprising:
    determining, by the controller, that the previous measurement of the distance is not stored in the non-transitory memory; and
    storing, by the controller in the non-transitory memory, the current measurement of the distance as the previous measurement of the distance, as the camber adjustment value, and as a baseline camber adjustment value.

3. The method of claim 1, wherein the distance is indicative of a thickness of the tissue when the first and second jaws are in the closed position with tissue grasped therein.

4. The method of claim 1, wherein the distance is indicative of the camber of the first jaw when the first and second jaws are in the closed position with no tissue grasped therein.

5. The method of claim 1, wherein determining, by the controller, whether the first and second jaws are in the closed position with tissue grasped therebetween comprises one of:
    determining that a difference between the current measurement of the distance and the previous measurement of the distance does not exceed a measurement variation threshold and that the current measurement of the distance exceeds a predefined distance value, and based thereon, determining that the first and second jaws are closed with tissue grasped therebetween;
    determining that the difference between the current measurement of distance and the previous measurement of the distance does not exceed a measurement variation threshold and that the current measurement of the distance does not exceed the predefined distance value, and based thereon, determining that the first and second jaws are closed with no tissue grasped therebetween;
    determining that the difference between the current measurement of the distance and the previous measurement of the distance exceeds the measurement variation threshold and that the current measurement of the distance exceeds the previous measurement of the distance, and based thereon, determining that the first and second jaws are closed with tissue grasped therebetween; or determining that the difference between a current measurement of the distance and the previous measurement of the distance exceeds a measurement variation threshold and that the current measurement of the distance does not exceed the previous measurement of the distance, and based thereon, determining that the first and second jaws are closed with no tissue grasped therebetween.

6. The method of claim 1, wherein the sensor assembly includes:
   a magnet disposed at a distal end of the first jaw or the second jaw, and
   a magnetic sensor disposed at the distal end of an opposite first jaw or second jaw, the method further comprising:
   sensing, by the magnetic sensor, a magnetic field indicative of a proximity of the distal end of the first jaw to the distal end of the second jaw.

7. The method of claim 6, wherein the magnetic sensor includes a hall sensor.

8. The method of claim 1, further comprising, determining, by the controller that the surgical stapling instrument was fired immediately preceding the actuation, and based thereon,
   retrieving, by the controller, from the non-transitory memory, a previous measurement of the distance, when the first and second jaws were closed with no tissue grasped, adjacent to the current measurement of the distance;
   deriving, by the controller, a de-camber estimate from a difference between the current measurement of the distance and the previous measurement of the distance, when the first and second jaws were closed with no tissue grasped, adjacent to the current measurement of the distance; and
   storing, by the controller, in the non-transitory memory, the de-camber estimate and the current measurement of the distance.

9. The method of claim 8, wherein the end effector further comprises a cutting edge configured to be displaced from a proximal end to a distal end of the first and second jaws such that at least a portion of the cutting edge is configured to transect the grasped tissue over a number of firings, the method further comprising:
   determining, by the controller, that a firing has been initiated;
   retrieving, by the controller, from the non-transitory memory, the de-camber estimate;
   determining, by the controller, that the de-camber estimate is more than a de-camber threshold; and
   adjusting, by the controller, a mode of operation of the firing based on the de-camber estimate.

10. The method of claim 9, further comprising:
    adjusting, by the controller, a force and speed of the cutting edge based on the de-camber estimate.

11. The method of claim 9,
    wherein the sensor assembly further comprises force sensors disposed at four locations along a channel of the lower jaw to sense a compression force indicative of thickness of the grasped tissue, the force of the cutting edge when the grasped tissue is transected, and to track the location of the cutting edge.

12. The method of claim 11, further comprising:
    upon determining that the surgical stapling instrument was fired immediately preceding the closing of the first and second jaws, providing, by the controller, an indication of the de-camber estimate and characteristics of the firing to a user of the surgical stapling instrument,
    wherein the characteristics of the firing includes number of firings, and measurements of force and speed of the cutting edge at each corresponding location of the cutting edge.

13. The method of claim 11, wherein the force sensors may be used to estimate the tissue thickness and force of the cutting edge.

14. A method for operating a surgical stapling instrument, the surgical stapling instrument comprising a controller and an end effector including a first jaw pivotably coupled at a proximal end thereof with a second jaw so as to be pivotable between an open position and a closed position for grasping tissue therebetween, the method comprising:
    detecting, by the controller, that the first and second jaws have been actuated from the closed position to the open position and back to the closed position for a first time;
    sensing, by a sensor assembly disposed at a distal end of the end effector and in signal communication with the controller, a proximity of a distal end of the first jaw to a distal end of the second jaw, in response to the first and second jaws having been actuated for the first time, generating a first signal indicative thereof, and communicating the first signal to the controller, wherein the first signal includes data indicative of a camber of the first jaw;
    deriving, by the controller, from the first signal, a current measurement of a distance between the distal end of the first jaw and the distal end of the second jaw;
    detecting, by the controller, data indicative that a previous measurement of the distance has not been previously stored;
    storing, by the controller in a non-transitory memory coupled with the controller, the current measurement of the distance as the previous measurement of the distance, as a camber adjustment value, and as a baseline camber adjustment value;
    detecting, by the controller, that the first and second jaws have been actuated from the closed position to the open position and back to the closed position for a second time with no tissue grasped therein;
    sensing, by the sensor assembly, the proximity, in response to the first and second jaws being actuated for the second time, generating a second signal indicative thereof, and communicating the second signal to the controller, wherein the second signal includes data indicative of an amount of the tissue grasped;
    deriving, by the controller, based on the second signal, the current measurement of the distance;
    updating, by the controller, the adjusted camber value with the current measurement of the distance;
    detecting, by the controller, that the first and second jaws have been actuated from the closed position to the open position and back to the closed position for a third time with tissue grasped therein;
    sensing, by the sensor assembly, the proximity, in response to the first and second jaws having been actuated for the third time, generating a third signal indicative thereof, and communicating the third signal to the controller, wherein the third signal includes data indicative of an amount of the tissue being grasped;
deriving, by the controller, based on the third signal, the current measurement of the distance;
deriving, from the current measurement of the distance, a measurement of thickness of the tissue; and
adjusting, by the controller, the current measurement of the thickness of the tissue based on the camber adjustment value.

15. A surgical stapling instrument comprising:
an end effector including a first jaw pivotably coupled at a proximal end thereof with a second jaw so as to be pivotable between an open position and a closed position for grasping tissue therebetween;
a sensor assembly disposed at a distal end of the end effector, the sensor assembly in signal communication with a controller, the sensor assembly configured to sense a proximity of a distal end of the first jaw to a distal end of the second jaw, in response to the first and second jaws being actuated by the end effector from the closed position to the open position and back to the closed position, generate a first signal indicative thereof, and communicate the first signal to a controller, wherein the sensor assembly is in signal communication with the controller;
the controller coupled with a non-transitory memory, the controller configured to:
derive, from the first signal, a current measurement of a distance between the distal end of the first jaw and the distal end of the second jaw;
store, in the non-transitory memory, the current measurement of the distance;
retrieve, from the non-transitory memory, data indicative of a previous measurement of the distance, the controller further configured to perform one of:
determine that the surgical stapling instrument was fired immediately preceding the first and second jaws being actuated and adjust a camber adjustment value stored in the non-transitory memory based on the current measurement of the distance, wherein the distance is indicative of the camber of the first jaw;
determine that the surgical stapling instrument was not fired immediately preceding the first and second jaws being actuated and determine whether the first and second jaws are in the closed position with tissue grasped therebetween, and based thereon, the controller further configured to perform one of:
determine that the first and second jaws are in the closed position with tissue grasped therebetween, derive a current measurement of a thickness of the tissue based on the current measurement of the distance, and adjust the current measurement of the thickness of the tissue based on the previous measurement of the distance when the first and second jaws were in the closed position with no tissue grasped; or
determine that the first and second jaws are in the closed position with no tissue grasped therebetween and adjust the camber adjustment value based on the current measurement of the distance, wherein the current measurement of the distance is indicative of the camber of the first jaw.

16. The surgical stapling instrument of claim 15, wherein the controller is further configured to:
determine that the previous measurement of the distance is not stored in the non-transitory memory; and
store, in the non-transitory memory, the current measurement of the distance as the previous measurement of the distance, as the camber adjustment value, and as a baseline camber adjustment value.

17. The surgical stapling instrument of claim 15, wherein the current measurement of the distance is indicative of a measurement of the thickness of the tissue when the first and second jaws are in the closed position with tissue grasped therein.

18. The surgical stapling instrument of claim 15, wherein the current measurement of the distance is indicative of the camber of the first jaw when the first and second jaws are in the closed position with no tissue grasped therein.

19. The surgical stapling instrument of claim 15, wherein the sensor assembly includes:
a magnet disposed at a distal end of the first jaw or the second jaw, and
a magnetic sensor disposed at the distal end of an opposite first jaw or second jaw, wherein the magnetic sensor is configured to sense a magnetic field indicative of the proximity of the distal end of the first jaw to the distal end of the second jaw.

20. The surgical stapling instrument of claim 19, wherein the magnetic sensor includes a hall sensor.

21. The surgical stapling instrument of claim 15, wherein the controller is further configured to determine that the surgical stapling instrument was fired immediately preceding the closing of the first and second jaws and based there on,
retrieve, from the non-transitory memory, a previous measurement of the distance, when the first and second jaws were closed with no tissue grasped, adjacent to the current measurement of the distance;
derive a de-camber estimate from a change between the current measurement of the distance and the previous measurement of the distance, when the first and second jaws were closed with no tissue grasped, adjacent to the current measurement of the distance; and
store, in the non-transitory memory, the de-camber estimate.

22. The surgical stapling instrument of claim 21,
wherein the end effector further comprises a cutting edge configured to be displaced from a proximal end to a distal end of the first and second jaws such that at least a portion of the cutting edge is configured to transect the grasped tissue over a number of firings, and
wherein the controller is further configured to:
detect that the surgical stapling instrument is about to fire;
retrieve, from the non-transitory memory, the de-camber estimate;
determine that the de-camber estimate is less than a minimum de-camber threshold; and
adjust a mode of operation of the firing based on the de-camber estimate.

23. The surgical stapling instrument of claim 22, wherein adjusting the operation of the firing further comprises:
adjusting a force and speed of the cutting edge.

24. The surgical stapling instrument of claim 22,
wherein the sensor assembly further comprises force sensors disposed at four locations along a channel of the lower jaw to sense a compression force indicative of thickness of the grasped tissue, the force of the cutting edge when the grasped tissue is transected, and to track the location of the cutting edge.

25. The surgical stapling instrument of claim 24, wherein the controller is further configured to:
upon determining that the surgical stapling instrument was fired immediately preceding the closing of the first and second jaws, provide an indication of the de-camber estimate and characteristics of the firing to a user of the surgical stapling instrument,
wherein the characteristics of the firing includes number of firings, and measurements of force and speed of the cutting edge at each corresponding location of the cutting edge.

26. The surgical stapling instrument of claim 24, wherein the force sensors may be used to estimate the tissue thickness and force of the cutting edge.

Example/Clause Set No. 2

1. A method for operating a surgical stapling instrument, the surgical stapling instrument comprising a controller and an end effector including a first jaw pivotably coupled at a proximal end thereof with a second jaw so as to be pivotable between an open position and a closed position for grasping tissue therebetween, the method comprising:
    detecting, by the controller, that the first and second jaws have been actuated from the closed position to the open position and back to the closed position;
    sensing, subsequent to the actuation, by a sensor assembly disposed at a distal end of the end effector, a proximity of a distal end of the first jaw and a distal end of the second jaw, in response to the first and second jaws being actuated, generating a first signal indicative thereof, and communicating the first signal to the controller, wherein the sensor assembly is in signal communication with the controller;
    deriving, by the controller, a current measurement of a distance between the distal end of the first jaw and the distal end of the second jaw based on the first signal;
    storing, by the controller, in a non-transitory memory coupled with the controller, the current measurement of the distance;
    retrieving, by the controller, from the non-transitory memory, data indicative of a previous measurement of the distance;
    determining, by the controller, whether the surgical stapling instrument was fired immediately preceding the actuation, and based thereon, the method further comprising one of:
        determining that the surgical stapling instrument was fired immediately preceding the actuation, the method further comprising:
            adjusting, by the controller, a camber adjustment value stored in the non-transitory memory, based on the current measurement of the distance, wherein the distance is indicative of the camber of the first jaw;
            retrieving, by the controller, from the non-transitory memory, a previous measurement of the distance, when the first and second jaws were closed with no tissue grasped, adjacent to the current measurement of the distance;
            deriving, by the controller, a de-camber estimate from a difference between the current measurement of the distance and the previous measurement of the distance, when the first and second jaws were closed with no tissue grasped, adjacent to the current measurement of the distance; and
            storing, by the controller, in the non-transitory memory, the de-camber estimate and the current measurement of the distance; or
        determining that the surgical stapling instrument was not fired immediately preceding the actuation, the method further comprising:
            determining, by the controller, whether the first and second jaws are in the closed position with tissue grasped therebetween, the method comprising one of:
                upon determining that the first and second jaws are in the closed position with tissue grasped therein, the method further comprising:
                    deriving, by the controller, a measurement of thickness of the tissue based on the distance; and
                    adjusting, by the controller, the current measurement of the thickness of the tissue, wherein the distance is indicative of an amount of tissue grasped therein; or
                upon determining that the first and second jaws are in the closed position with no tissue grasped therein, adjusting, by the controller, the camber adjustment value based on the current measurement of the distance, wherein the distance is indicative of the camber of the first jaw.

2. The method of claim 1, further comprising:
    determining, by the controller, that the previous measurement of the distance is not stored in the non-transitory memory; and
    storing, by the controller in the non-transitory memory, the current measurement of the distance as the previous measurement of the distance, as the camber adjustment value, and as a baseline camber adjustment value.

3. The method of claim 1, wherein the distance is indicative of a thickness of the tissue when the first and second jaws are in the closed position with tissue grasped therein.

4. The method of claim 1, wherein the distance is indicative of the camber of the first jaw when the first and second jaws are in the closed position with no tissue grasped therein.

5. The method of claim 1, wherein determining, by the controller, whether the first and second jaws are in the closed position with tissue grasped therebetween comprises one of:
    determining that a difference between the current measurement of the distance and the previous measurement of the distance does not exceed a measurement variation threshold and that the current measurement of the distance exceeds a predefined distance value, and based thereon, determining that the first and second jaws are closed with tissue grasped therebetween;
    determining that the difference between the current measurement of distance and the previous measurement of the distance does not exceed a measurement variation threshold and that the current measurement of the distance does not exceed the predefined distance value, and based thereon, determining that the first and second jaws are closed with no tissue grasped therebetween;

determining that the difference between the current measurement of the distance and the previous measurement of the distance exceeds the measurement variation threshold and that the current measurement of the distance exceeds the previous measurement of the distance, and based thereon, determining that the first and second jaws are closed with tissue grasped therebetween; or determining that the difference between a current measurement of the distance and the previous measurement of the distance exceeds a measurement variation threshold and that the current measurement of the distance does not exceed the previous measurement of the distance, and based thereon, determining that the first and second jaws are closed with no tissue grasped therebetween.

6. The method of claim 1, wherein the sensor assembly includes:
   a magnet disposed at a distal end of the first jaw or the second jaw, and
   a magnetic sensor disposed at the distal end of an opposite first jaw or second jaw, the method further comprising:
   sensing, by the magnetic sensor, a magnetic field indicative of a proximity of the distal end of the first jaw to the distal end of the second jaw.

7. The method of claim 6, wherein the magnetic sensor includes a hall sensor.

8. The method of claim 1, wherein the end effector further comprises a cutting edge configured to be displaced from a proximal end to a distal end of the first and second jaws such that at least a portion of the cutting edge is configured to transect the grasped tissue over a number of firings, the method further comprising:
   determining, by the controller, that a firing has been initiated;
   retrieving, by the controller, from the non-transitory memory, the de-camber estimate;
   determining, by the controller, that the de-camber estimate is more than a de-camber threshold; and
   adjusting, by the controller, a mode of operation of the firing based on the de-camber estimate.

9. The method of claim 8, further comprising:
   adjusting, by the controller, a force and speed of the cutting edge based on the de-camber estimate.

10. The method of claim 8, wherein the sensor assembly further comprises force sensors disposed at four locations along a channel of the lower jaw to sense a compression force indicative of thickness of the grasped tissue, the force of the cutting edge when the grasped tissue is transected, and to track the location of the cutting edge.

11. The method of claim 10, further comprising:
    upon determining that the surgical stapling instrument was fired immediately preceding the closing of the first and second jaws, providing, by the controller, an indication of the de-camber estimate and characteristics of the firing to a user of the surgical stapling instrument,
    wherein the characteristics of the firing includes number of firings, and measurements of force and speed of the cutting edge at each corresponding location of the cutting edge.

12. The method of claim 10, wherein the force sensors may be used to estimate the tissue thickness and force of the cutting edge.

13. A method for operating a surgical stapling instrument, the surgical stapling instrument comprising a controller and an end effector including a first jaw pivotably coupled at a proximal end thereof with a second jaw so as to be pivotable between an open position and a closed position for grasping tissue therebetween, the method comprising:
    detecting, by the controller, that the first and second jaws have been actuated from the closed position to the open position and back to the closed position for a first time;
    sensing, by a sensor assembly disposed at a distal end of the end effector and in signal communication with the controller, a proximity of a distal end of the first jaw to a distal end of the second jaw, in response to the first and second jaws having been actuated for the first time, generating a first signal indicative thereof, and communicating the first signal to the controller, wherein the first signal includes data indicative of a camber of the first jaw;
    deriving, by the controller, from the first signal, a current measurement of a distance between the distal end of the first jaw and the distal end of the second jaw;
    detecting, by the controller, data indicative that a previous measurement of the distance has not been previously stored;
    storing, by the controller in a non-transitory memory coupled with the controller, the current measurement of the distance as the previous measurement of the distance, as a camber adjustment value, and as a baseline camber adjustment value;
    detecting, by the controller, that the first and second jaws have been actuated from the closed position to the open position and back to the closed position for a second time with no tissue grasped therein;
    sensing, by the sensor assembly, the proximity, in response to the first and second jaws being actuated for the second time, generating a second signal indicative thereof, and communicating the second signal to the controller, wherein the second signal includes data indicative of an amount of the tissue grasped;
    deriving, by the controller, based on the second signal, the current measurement of the distance;
    updating, by the controller, the adjusted camber value with the current measurement of the distance;
    detecting, by the controller, that the first and second jaws have been actuated from the closed position to the open position and back to the closed position for a third time with tissue grasped therein;
    sensing, by the sensor assembly, the proximity, in response to the first and second jaws having been actuated for the third time, generating a third signal indicative thereof, and communicating the third signal to the controller, wherein the third signal includes data indicative of an amount of the tissue being grasped;
    deriving, by the controller, based on the third signal, the current measurement of the distance;
    deriving, from the current measurement of the distance, a measurement of thickness of the tissue; and adjusting, by the controller, the current measurement of the thickness of the tissue based on the camber adjustment value.

14. A surgical stapling instrument comprising:
an end effector including a first jaw pivotably coupled at a proximal end thereof with a second jaw so as to be pivotable between an open position and a closed position for grasping tissue therebetween;
a sensor assembly disposed at a distal end of the end effector, the sensor assembly in signal communication with a controller, the sensor assembly configured to:
sense a proximity of a distal end of the first jaw to a distal end of the second jaw, in response to the first and second jaws being actuated by the end effector from the closed position to the open position and back to the closed position, generate a first signal indicative thereof, and communicate the first signal to a controller, wherein the sensor assembly is in signal communication with the controller;
the controller coupled with a non-transitory memory, the controller configured to:
derive, from the first signal, a current measurement of a distance between the distal end of the first jaw and the distal end of the second jaw;
store, in the non-transitory memory, the current measurement of the distance;
retrieve, from the non-transitory memory, data indicative of a previous measurement of the distance;
determine whether the surgical stapling instrument was fired immediately preceding the first and second jaws being in the closed position;
upon determining that the surgical stapling instrument was fired immediately preceding the closing of the first and second jaws, the controller further configured to:
adjust a camber adjustment value stored in the non-transitory memory, based on the current measurement of the distance, wherein the distance is indicative of the camber of the first jaw;
retrieve, from the non-transitory memory, a previous measurement of the distance, when the first and second jaws were closed with no tissue grasped, adjacent to the current measurement of the distance;
derive a de-camber estimate from a change between the current measurement of the distance and the previous measurement of the distance, when the first and second jaws were closed with no tissue grasped, adjacent to the current measurement of the distance; and
store, in the non-transitory memory, the de-camber estimate and the current measurement of the distance;
upon determining that the surgical stapling instrument was not fired immediately prior to the first and second jaws being in the closed position, the controller further configured to:
determine whether the first and second jaws are in the closed position with tissue grasped therein;
upon determining that the first and second jaws are in the closed position with tissue grasped therein, the controller further configured to:
derive a current measurement of a thickness of the tissue based on the current measurement of the distance;
adjust the current measurement of the thickness of the tissue based on the previous measurement of the distance when the first and second jaws were in the closed position with no tissue grasped; and
upon determining that the first and second jaws are in the closed position with no tissue grasped therein, the controller further configured to adjust the camber adjustment value based on the current measurement of the distance, wherein the current measurement of the distance is indicative of the camber of the first jaw.

15. The surgical stapling instrument of claim 14, wherein the controller is further configured to:
determine that the previous measurement of the distance is not stored in the non-transitory memory; and
store, in the non-transitory memory, the current measurement of the distance as the previous measurement of the distance, as the camber adjustment value, and as a baseline camber adjustment value.

16. The surgical stapling instrument of claim 14, wherein the current measurement of the distance is indicative of a measurement of the thickness of the tissue when the first and second jaws are in the closed position with tissue grasped therein.

17. The surgical stapling instrument of claim 14, wherein the current measurement of the distance is indicative of the camber of the first jaw when the first and second jaws are in the closed position with no tissue grasped therein.

18. The surgical stapling instrument of claim 14, wherein the sensor assembly includes:
a magnet disposed at a distal end of the first jaw or the second jaw, and
a magnetic sensor disposed at the distal end of an opposite first jaw or second jaw, wherein the magnetic sensor is configured to sense a magnetic field indicative of the proximity of the distal end of the first jaw to the distal end of the second jaw.

19. The surgical stapling instrument of claim 18, wherein the magnetic sensor includes a hall sensor.

20. The surgical stapling instrument of claim 14,
wherein the end effector further comprises a cutting edge configured to be displaced from a proximal end to a distal end of the first and second jaws such that at least a portion of the cutting edge is configured to transect the grasped tissue over a number of firings, and
wherein the controller is further configured to:
detect that the surgical stapling instrument is about to fire;
retrieve, from the non-transitory memory, the de-camber estimate;
determine that the de-camber estimate is less than a minimum de-camber threshold; and
adjust a mode of operation of the firing based on the de-camber estimate.

21. The surgical stapling instrument of claim 20, wherein adjusting the operation of the firing further comprises:
adjusting a force and speed of the cutting edge.

22. The surgical stapling instrument of claim 20,
wherein the sensor assembly further comprises force sensors disposed at four locations along a channel of the lower jaw to sense a compression force indicative of thickness of the grasped tissue, the force of the cutting edge when the grasped tissue is transected, and to track the location of the cutting edge.

23. The surgical stapling instrument of claim 22, wherein the controller is further configured to:
upon determining that the surgical stapling instrument was fired immediately preceding the closing of the first and second jaws, provide an indication of the de-camber estimate and characteristics of the firing to a user of the surgical stapling instrument,
wherein the characteristics of the firing includes number of firings, and measurements of force and speed of the cutting edge at each corresponding location of the cutting edge.
24. The surgical stapling instrument of claim 22, wherein the force sensors may be used to estimate the tissue thickness and force of the cutting edge.

Example/Clause Set No. 3

1. A surgical stapling instrument comprising:
an end effector configured to grasp tissue, the end effector comprising:
a first jaw pivotably coupled at a proximal end thereof with a second jaw so as to be pivotable between an open position and a closed position for grasping tissue therebetween;
a knife configured to be displaced from a proximal end of the end effector to a distal end thereof, so as to transect tissue grasped between the first and second jaws, one of the first or second jaws further configured to receive a staple cartridge seatable therein and including a sled and staples, the sled configured to be displaced by the knife from a proximal end to a distal end of the staple cartridge to deploy the staples into the tissue grasped between the first and second jaws along the transection; and
a sensor deployed at the distal end of the end effector and configured to sense a parameter indicative of a distance between the first and second jaws and generate a signal indicative thereof;
a motor located external to the end effector;
a drive train operably coupled between the motor and the knife, wherein the motor is configured to controllably displace the drive train so as to displace the knife, and thereby the sled, so as to substantially simultaneously transect the tissue grasped by the end effector and deploy the staples therein along, and on either side of, the transection, and thereafter retract the drive train so as to retract the knife back to the proximal end of the end effector;
a control circuit coupled with the sensor and the motor and which controls a rate at which the motor is attempting to displace the drive train, where in the control circuit is further configured to:
determine, based on the signal when the first and second jaws have been actuated from the closed position to the open position, without the motor having displaced the drive train, and back to the closed position, the current distance between the first and second jaws and further determine an adjusted current distance based on an adjusted baseline distance determined, based on the signal when the first and second jaws have been actuated from the closed position to the open position, after the motor has displaced and retracted the knife, and back to the closed position, based on the then current distance between first and second jaws and a previously determined adjusted baseline distance.

2. The surgical stapling instrument of claim 1, wherein the control circuit is further configured, while the first and second jaws remain in the closed position, to periodically determine the adjusted current distance between the first and second jaws and based on a comparison between at least a subset of the determined adjusted current distances, determine when to initiate displacement of the drive train.

3. The surgical stapling instrument of claim 1, wherein the control circuit is further configured to determine, based on the adjusted current distance between the first and second jaws, a rate of displacement at which the motor should attempt to maintain during a next displacement of the drive train.

4. The surgical stapling instrument of claim 3, wherein the control circuit is further configured to periodically repeat the determination of the adjusted current distance and rate of displacement as the drive train is displaced.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Pat. App. No. 63/467,622, entitled "Surgical Stapler Cartridge Having Intermediate Raised Tissue Engagement Protrusions," filed on May 19, 2023; U.S. Pat. App. No. 63/467,623, entitled "Surgical Stapler Cartridge Having Tissue Engagement Protrusions with Enlarged Engagement Surface," filed on May 19, 2023; U.S. Pat. App. No. 63/467,648, entitled "Surgical Stapler Cartridge Having Raised Surface to Promote Buttress Adhesion," filed on May 19, 2023; U.S. Pat. App. No. 63/467,469, entitled "Surgical Stapler Cartridge Having Cartridge Retention Features," filed on May 19, 2023; U.S. Pat. App. No. 63/459,739, entitled "Surgical Stapler Anvil Having Staple Forming Pockets with Laterally Varying Orientations," filed on May 19, 2023; U.S. Pat. App. No. 63/467,656, entitled "Surgical Stapler With Discretely Positionable Distal Tip," filed on May 19, 2023; and/or U.S. Pat. App. No. 63/467,615, entitled "Incompatible Staple Cartridge Use Prevention Features for Surgical Stapler," filed on May 19, 2023.

Additionally, any one or more of the teachings herein may be combined with any one or more of the teachings disclosed in U.S. Pat. App. No. 63/459,739, entitled "Surgical Stapler Anvil Having Staple Forming Pockets with Laterally Varying Orientations," filed on Apr. 17, 2023. The disclosure of each of these U.S. patent applications is incorporated by reference herein in its entirety.

Additionally, any one or more of the teachings herein may be combined with any one or more of the teachings disclosed in U.S. Pat. No. 11,304,697, entitled "Surgical Stapler with Deflectable Distal Tip," issued Apr. 19, 2022, the disclosure of which is incorporated by reference herein, in its entirety; U.S. Pat. No. 11,317,912, entitled "Surgical Stapler with Rotatable Distal Tip," issued May 3, 2022, the disclosure of which is incorporated by reference herein, in its entirety;

and/or U.S. Pat. No. 11,439,391, entitled "Surgical Stapler with Toggling Distal Tip," issued Sep. 13, 2022, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A method for operating a surgical stapling instrument, the surgical stapling instrument comprising a controller and an end effector including a first jaw pivotably coupled at a proximal end thereof with a second jaw so as to be pivotable between an open position and a closed position for grasping tissue therebetween, the method comprising:
    detecting, by the controller, that the first and second jaws have been actuated from the closed position to the open position and back to the closed position;
    sensing, subsequent to the actuation, by a sensor assembly disposed at a distal end of the end effector, a proximity of a distal end of the first jaw and a distal end of the second jaw, in response to the first and second jaws being actuated, generating a first signal indicative thereof, and communicating the first signal to the controller, wherein the sensor assembly is in signal communication with the controller;
    deriving, by the controller, a current measurement of a distance between the distal end of the first jaw and the distal end of the second jaw based on the first signal;
    storing, by the controller, in a non-transitory memory coupled with the controller, the current measurement of the distance;
    retrieving, by the controller, from the non-transitory memory, data indicative of a previous measurement of the distance, the method further comprising one of:
    determining, by the controller, that the surgical stapling instrument was fired immediately preceding the actuation, and based thereon, adjusting, by the controller, a camber adjustment value stored in the non-transitory memory based on the current measurement of the distance, wherein the distance is indicative of the camber of the first jaw; or
    determining, by the controller, that the surgical stapling instrument was not fired immediately preceding the actuation, and based thereon, determining, by the controller, whether the first and second jaws are in the closed position with tissue grasped therebetween, the method comprising one of:
        determining that the first and second jaws are in the closed position with tissue grasped therebetween, deriving, by the controller, a measurement of thickness of the tissue based on the distance and adjusting, by the controller, the current measurement of the thickness of the tissue, wherein the distance is indicative of an amount of tissue grasped therein; or
        determining that the first and second jaws are in the closed position with no tissue grasped therebetween and adjusting, by the controller, the camber adjustment value based on the current measurement of the distance, wherein the distance is indicative of the camber of the first jaw.

2. The method of claim 1, further comprising:
    determining, by the controller, that the previous measurement of the distance is not stored in the non-transitory memory; and
    storing, by the controller in the non-transitory memory, the current measurement of the distance as the previous measurement of the distance, as the camber adjustment value, and as a baseline camber adjustment value.

3. The method of claim 1, wherein the distance is indicative of a thickness of the tissue when the first and second jaws are in the closed position with tissue grasped therein.

4. The method of claim 1, wherein the distance is indicative of the camber of the first jaw when the first and second jaws are in the closed position with no tissue grasped therein.

5. The method of claim 1, wherein determining, by the controller, whether the first and second jaws are in the closed position with tissue grasped therebetween comprises one of:
   determining that a difference between the current measurement of the distance and the previous measurement of the distance does not exceed a measurement variation threshold and that the current measurement of the distance exceeds a predefined distance value, and based thereon, determining that the first and second jaws are closed with tissue grasped therebetween;
   determining that the difference between the current measurement of distance and the previous measurement of the distance does not exceed a measurement variation threshold and that the current measurement of the distance does not exceed the predefined distance value, and based thereon, determining that the first and second jaws are closed with no tissue grasped therebetween;
   determining that the difference between the current measurement of the distance and the previous measurement of the distance exceeds the measurement variation threshold and that the current measurement of the distance exceeds the previous measurement of the distance, and based thereon, determining that the first and second jaws are closed with tissue grasped therebetween; or
   determining that the difference between a current measurement of the distance and the previous measurement of the distance exceeds a measurement variation threshold and that the current measurement of the distance does not exceed the previous measurement of the distance, and based thereon, determining that the first and second jaws are closed with no tissue grasped therebetween.

6. The method of claim 1, wherein the sensor assembly includes:
   a magnet disposed at a distal end of the first jaw or the second jaw, and
   a magnetic sensor disposed at the distal end of an opposite first jaw or second jaw, the method further comprising:
   sensing, by the magnetic sensor, a magnetic field indicative of a proximity of the distal end of the first jaw to the distal end of the second jaw.

7. The method of claim 6, wherein the magnetic sensor includes a hall sensor.

8. The method of claim 1, further comprising, determining, by the controller that the surgical stapling instrument was fired immediately preceding the actuation, and based thereon,
   retrieving, by the controller, from the non-transitory memory, a previous measurement of the distance, when the first and second jaws were closed with no tissue grasped, adjacent to the current measurement of the distance;
   deriving, by the controller, a de-camber estimate from a difference between the current measurement of the distance and the previous measurement of the distance, when the first and second jaws were closed with no tissue grasped, adjacent to the current measurement of the distance; and
   storing, by the controller, in the non-transitory memory, the de-camber estimate and the current measurement of the distance.

9. The method of claim 8, wherein the end effector further comprises a cutting edge configured to be displaced from a proximal end to a distal end of the first and second jaws such that at least a portion of the cutting edge is configured to transect the grasped tissue over a number of firings, the method further comprising:
   determining, by the controller, that a firing has been initiated;
   retrieving, by the controller, from the non-transitory memory, the de-camber estimate;
   determining, by the controller, that the de-camber estimate is more than a de-camber threshold; and
   adjusting, by the controller, a mode of operation of the firing based on the de-camber estimate.

10. The method of claim 9, further comprising:
    adjusting, by the controller, a force and speed of the cutting edge based on the de-camber estimate.

11. The method of claim 9,
    wherein the sensor assembly further comprises force sensors disposed at four locations along a channel of the lower jaw to sense a compression force indicative of thickness of the grasped tissue, the force of the cutting edge when the grasped tissue is transected, and to track the location of the cutting edge.

12. The method of claim 11, further comprising:
    upon determining that the surgical stapling instrument was fired immediately preceding the closing of the first and second jaws, providing, by the controller, an indication of the de-camber estimate and characteristics of the firing to a user of the surgical stapling instrument, wherein the characteristics of the firing includes number of firings, and measurements of force and speed of the cutting edge at each corresponding location of the cutting edge.

13. The method of claim 11, wherein the force sensors may be used to estimate the tissue thickness and force of the cutting edge.

14. A method for operating a surgical stapling instrument, the surgical stapling instrument comprising a controller and an end effector including a first jaw pivotably coupled at a proximal end thereof with a second jaw so as to be pivotable between an open position and a closed position for grasping tissue therebetween, the method comprising:
    detecting, by the controller, that the first and second jaws have been actuated from the closed position to the open position and back to the closed position for a first time;
    sensing, by a sensor assembly disposed at a distal end of the end effector and in signal communication with the controller, a proximity of a distal end of the first jaw to a distal end of the second jaw, in response to the first and second jaws having been actuated for the first time, generating a first signal indicative thereof, and communicating the first signal to the controller, wherein the first signal includes data indicative of a camber of the first jaw;
    deriving, by the controller, from the first signal, a current measurement of a distance between the distal end of the first jaw and the distal end of the second jaw;
    detecting, by the controller, data indicative that a previous measurement of the distance has not been previously stored;
    storing, by the controller in a non-transitory memory coupled with the controller, the current measurement of the distance as the previous measurement of the distance, as a camber adjustment value, and as a baseline camber adjustment value;
detecting, by the controller, that the first and second jaws have been actuated from the closed position to the open position and back to the closed position for a second time with no tissue grasped therein;
sensing, by the sensor assembly, the proximity, in response to the first and second jaws being actuated for the second time, generating a second signal indicative thereof, and communicating the second signal to the controller, wherein the second signal includes data indicative of an amount of the tissue grasped;
deriving, by the controller, based on the second signal, the current measurement of the distance;
updating, by the controller, the adjusted camber value with the current measurement of the distance;
detecting, by the controller, that the first and second jaws have been actuated from the closed position to the open position and back to the closed position for a third time with tissue grasped therein;
sensing, by the sensor assembly, the proximity, in response to the first and second jaws having been actuated for the third time, generating a third signal indicative thereof, and communicating the third signal to the controller, wherein the third signal includes data indicative of an amount of the tissue being grasped;
deriving, by the controller, based on the third signal, the current measurement of the distance;
deriving, from the current measurement of the distance, a measurement of thickness of the tissue; and
adjusting, by the controller, the current measurement of the thickness of the tissue based on the camber adjustment value.

15. A surgical stapling instrument comprising:
an end effector including a first jaw pivotably coupled at a proximal end thereof with a second jaw so as to be pivotable between an open position and a closed position for grasping tissue therebetween;
a sensor assembly disposed at a distal end of the end effector, the sensor assembly in signal communication with a controller, the sensor assembly configured to sense a proximity of a distal end of the first jaw to a distal end of the second jaw, in response to the first and second jaws being actuated by the end effector from the closed position to the open position and back to the closed position, generate a first signal indicative thereof, and communicate the first signal to a controller, wherein the sensor assembly is in signal communication with the controller;
the controller coupled with a non-transitory memory, the controller configured to:
derive, from the first signal, a current measurement of a distance between the distal end of the first jaw and the distal end of the second jaw;
store, in the non-transitory memory, the current measurement of the distance;
retrieve, from the non-transitory memory, data indicative of a previous measurement of the distance, the controller further configured to perform one of:
determine that the surgical stapling instrument was fired immediately preceding the first and second jaws being actuated and adjust a camber adjustment value stored in the non-transitory memory based on the current measurement of the distance, wherein the distance is indicative of the camber of the first jaw;
determine that the surgical stapling instrument was not fired immediately preceding the first and second jaws being actuated and determine whether the first and second jaws are in the closed position with tissue grasped therebetween, and based thereon, the controller further configured to perform one of:
determine that the first and second jaws are in the closed position with tissue grasped therebetween, derive a current measurement of a thickness of the tissue based on the current measurement of the distance, and adjust the current measurement of the thickness of the tissue based on the previous measurement of the distance when the first and second jaws were in the closed position with no tissue grasped; or
determine that the first and second jaws are in the closed position with no tissue grasped therebetween and adjust the camber adjustment value based on the current measurement of the distance, wherein the current measurement of the distance is indicative of the camber of the first jaw.

16. The surgical stapling instrument of claim 15, wherein the controller is further configured to:
determine that the previous measurement of the distance is not stored in the non-transitory memory; and
store, in the non-transitory memory, the current measurement of the distance as the previous measurement of the distance, as the camber adjustment value, and as a baseline camber adjustment value.

17. The surgical stapling instrument of claim 15, wherein the current measurement of the distance is indicative of a measurement of the thickness of the tissue when the first and second jaws are in the closed position with tissue grasped therein.

18. The surgical stapling instrument of claim 15, wherein the current measurement of the distance is indicative of the camber of the first jaw when the first and second jaws are in the closed position with no tissue grasped therein.

19. The surgical stapling instrument of claim 15, wherein the sensor assembly includes:
a magnet disposed at a distal end of the first jaw or the second jaw, and
a magnetic sensor disposed at the distal end of an opposite first jaw or second jaw, wherein the magnetic sensor is configured to sense a magnetic field indicative of the proximity of the distal end of the first jaw to the distal end of the second jaw.

20. The surgical stapling instrument of claim 19, wherein the magnetic sensor includes a hall sensor.

21. The surgical stapling instrument of claim 15, wherein the controller is further configured to determine that the surgical stapling instrument was fired immediately preceding the closing of the first and second jaws and based there on,
retrieve, from the non-transitory memory, a previous measurement of the distance, when the first and second jaws were closed with no tissue grasped, adjacent to the current measurement of the distance;
derive a de-camber estimate from a change between the current measurement of the distance and the previous measurement of the distance, when the first and second jaws were closed with no tissue grasped, adjacent to the current measurement of the distance; and
store, in the non-transitory memory, the de-camber estimate.

22. The surgical stapling instrument of claim 21,
wherein the end effector further comprises a cutting edge configured to be displaced from a proximal end to a distal end of the first and second jaws such that at least a portion of the cutting edge is configured to transect the grasped tissue over a number of firings, and
wherein the controller is further configured to:
- detect that the surgical stapling instrument is about to fire;
- retrieve, from the non-transitory memory, the de-camber estimate;
- determine that the de-camber estimate is less than a minimum de-camber threshold; and
- adjust a mode of operation of the firing based on the de-camber estimate.

23. The surgical stapling instrument of claim 22, wherein adjusting the operation of the firing further comprises: adjusting a force and speed of the cutting edge.

24. The surgical stapling instrument of claim 22,
wherein the sensor assembly further comprises force sensors disposed at four locations along a channel of the lower jaw to sense a compression force indicative of thickness of the grasped tissue, the force of the cutting edge when the grasped tissue is transected, and to track the location of the cutting edge.

25. The surgical stapling instrument of claim 24, wherein the controller is further configured to:
- upon determining that the surgical stapling instrument was fired immediately preceding the closing of the first and second jaws, provide an indication of the de-camber estimate and characteristics of the firing to a user of the surgical stapling instrument,
wherein the characteristics of the firing includes number of firings, and measurements of force and speed of the cutting edge at each corresponding location of the cutting edge.

26. The surgical stapling instrument of claim 24, wherein the force sensors may be used to estimate the tissue thickness and force of the cutting edge.

* * * * *